(12) United States Patent
Klein

(10) Patent No.: US 7,380,944 B1
(45) Date of Patent: Jun. 3, 2008

(54) OPTIC NERVE DOCUMENTATION VIA ELECTRONIC MEDICAL RECORDS

(76) Inventor: Scott E. Klein, 10606 Boca Pointe Dr., Orlando, FL (US) 32836

( * ) Notice: Subject to any disclaimer, the term of this patent is extended or adjusted under 35 U.S.C. 154(b) by 91 days.

(21) Appl. No.: 11/363,248

(22) Filed: Feb. 27, 2006

(51) Int. Cl.
*A61B 3/00* (2006.01)
(52) U.S. Cl. .................................... 351/246
(58) Field of Classification Search ........ 351/200–206, 351/239, 246
See application file for complete search history.

(56) References Cited

U.S. PATENT DOCUMENTS

2002/0005935 A1* 1/2002 Robin .................... 351/224
2005/0200808 A1* 9/2005 Wyatt .................... 351/246

\* cited by examiner

*Primary Examiner*—M. Hasan
(74) *Attorney, Agent, or Firm*—Allen D. Hertz

(57) ABSTRACT

A method of documenting a patient's optic nerve utilizing solid and dashed line arrows as well as other references to clearly describe the diagnosis of each visit. An electronic medical record software product that provides a method for entering, documenting, and recording the appearance and diagnosed status of a patient's optic nerve. The software can provide the user the ability to enter the information in a variety of ways, including selection of various features from images presented as examples, entry data via text or selection from a table, drawing the optic nerve, or from an image. The software can store and present an animated history to help provide prognosis.

20 Claims, 38 Drawing Sheets

Ocular Dexter

Ocular Sinister 1.00 CDR Total Rim Loss 0.10 CDR Full Rim

0.20 CDR Full Rim

0.25 CDR Full Rim

0.30 CDR Full Rim 0.35 CDR Full Rim
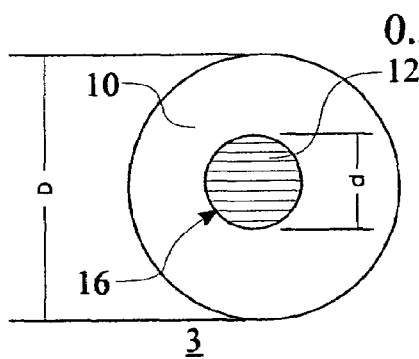
FIG. 8A
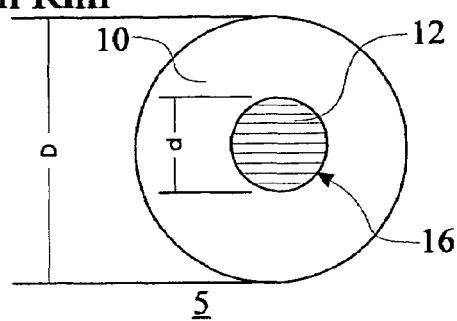
FIG. 8B
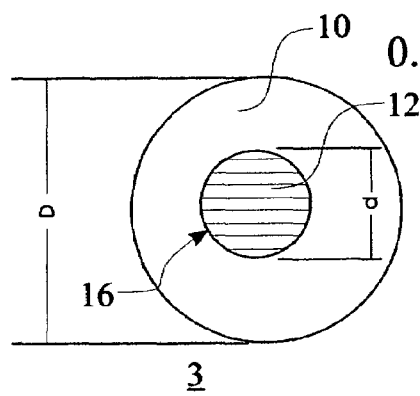
0.40 CDR Full Rim
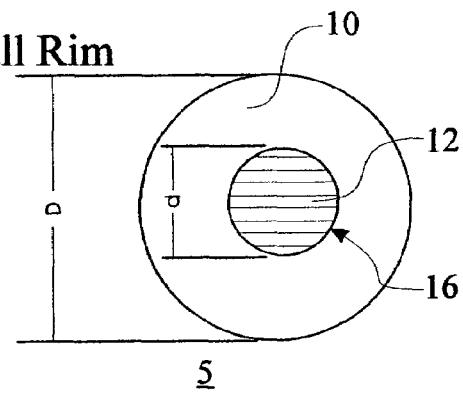
FIG. 9A
FIG. 9B
0.45 CDR Full Rim
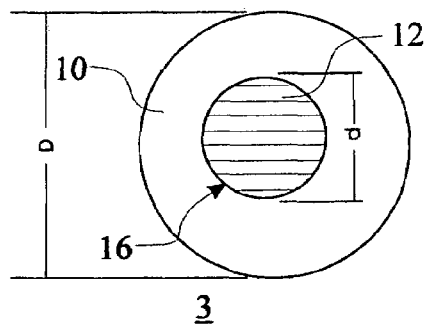
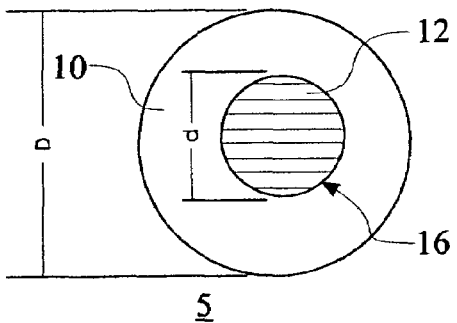
FIG. 10A
FIG. 10B

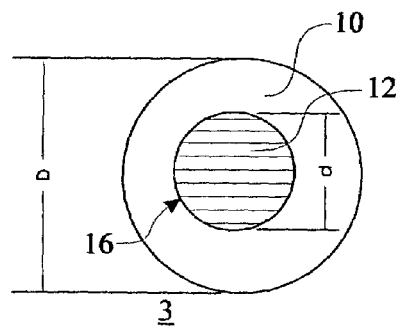
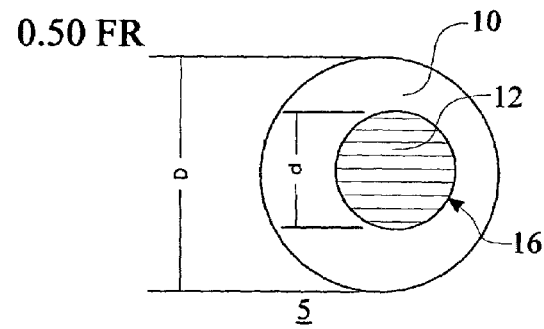
FIG. 11A  FIG. 11B
0.50 FR
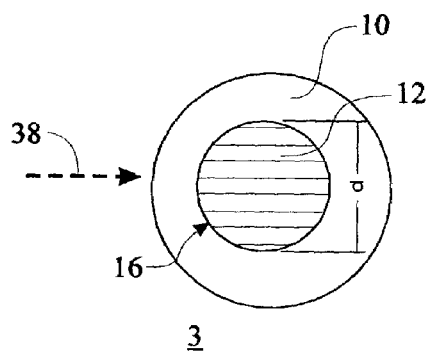
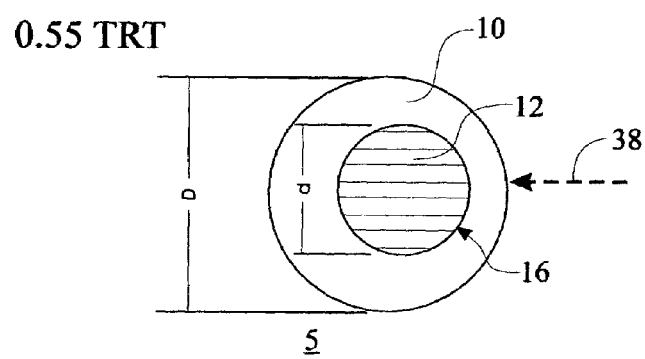
FIG. 12A  FIG. 12B
0.55 TRT
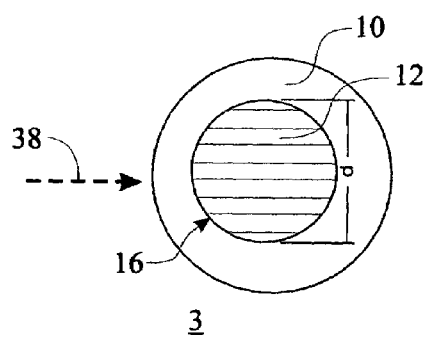
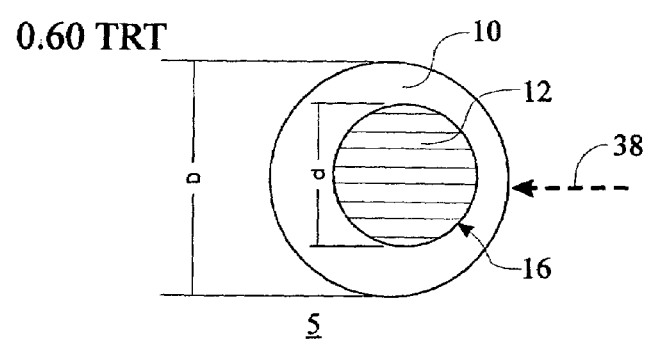
FIG. 13A  FIG. 13B
0.60 TRT 0.65 TRT 0.70 TRT 0.75 TRT 0.80 DRT 0.85 DRT 0.90 DRT

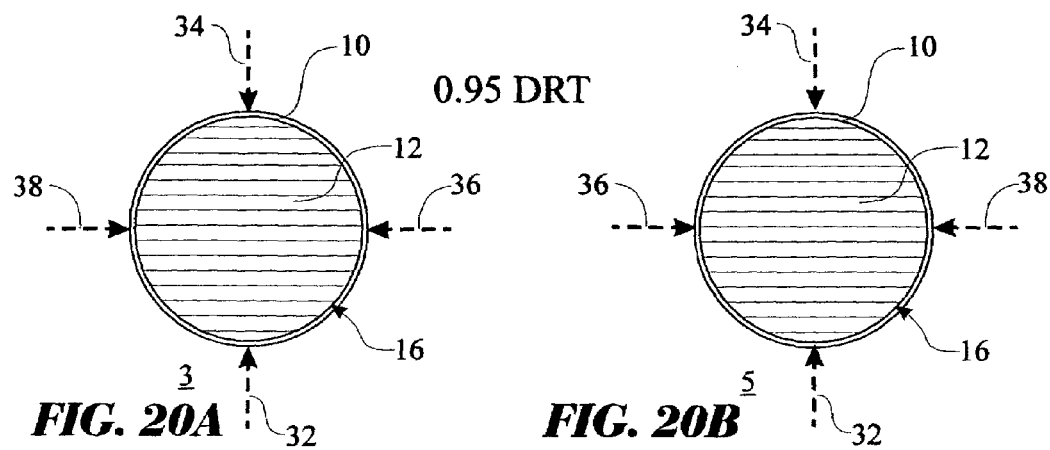
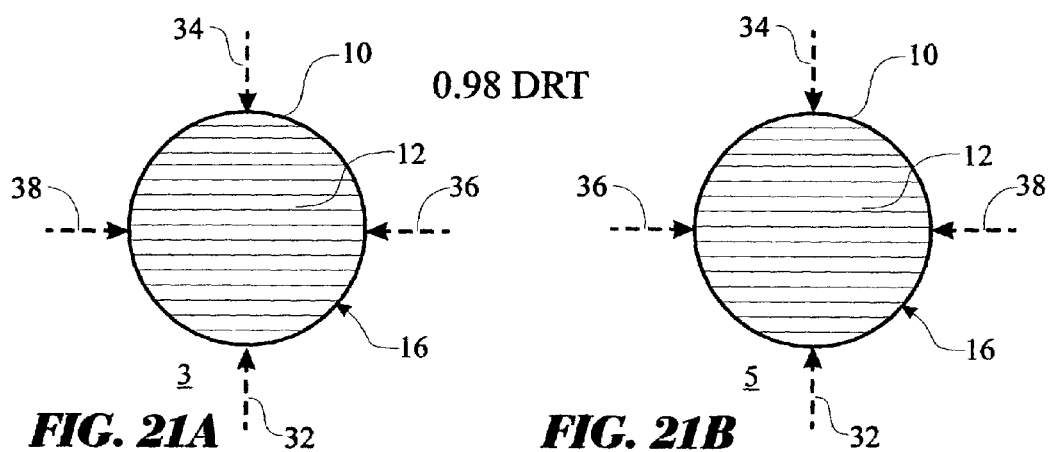
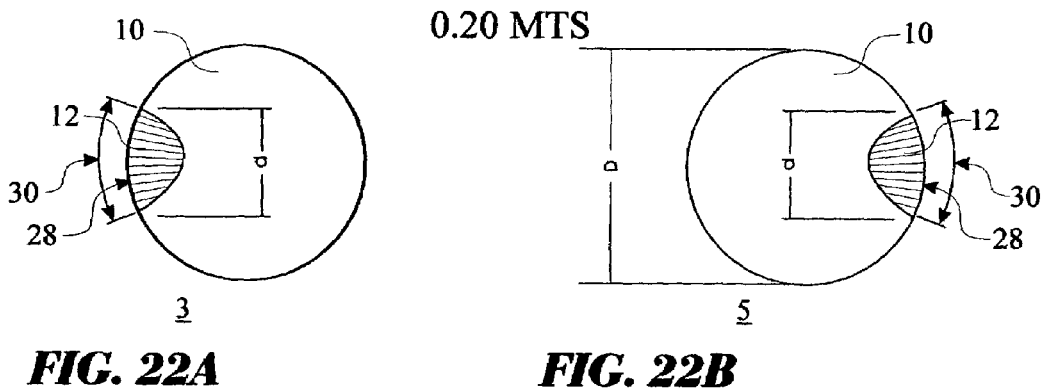

0.20 MNS
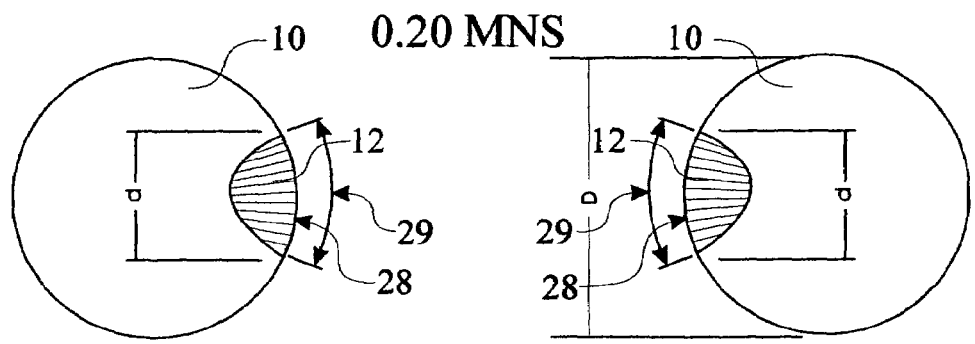
FIG. 23A  FIG. 23B
0.20 IN
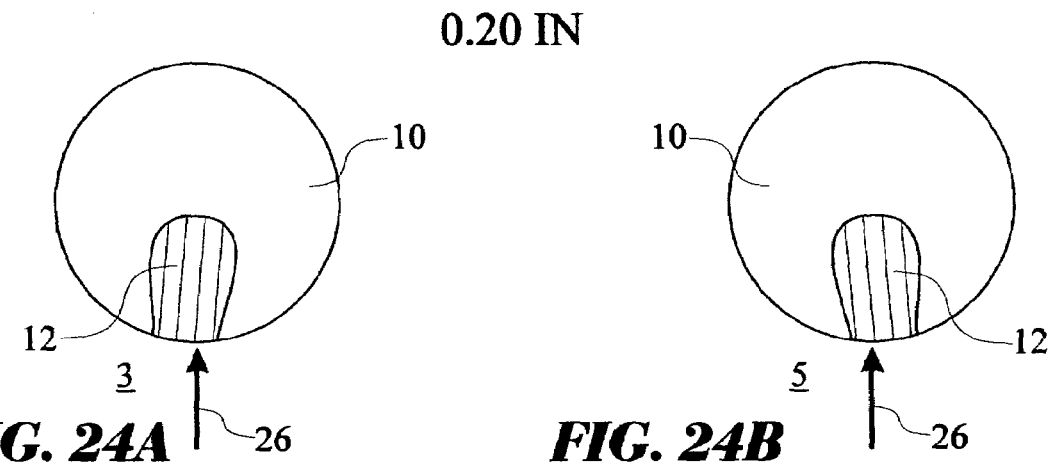
FIG. 24A  FIG. 24B
0.20 SN
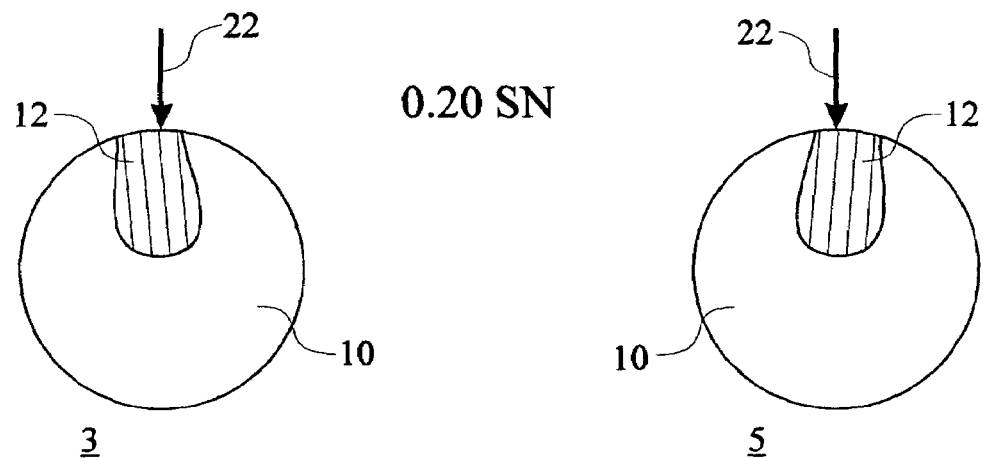
FIG. 25A  FIG. 25B

0.25 MTS 0.30 1+TS 0.35 1+TS 0.35 1+TS 0.40 1+TS 0.40 1+TS

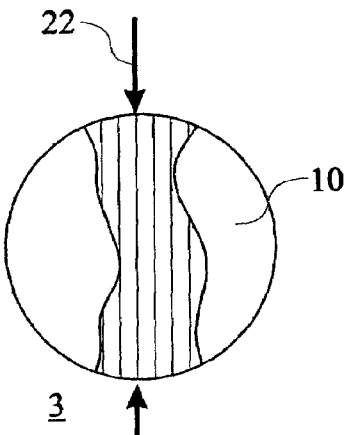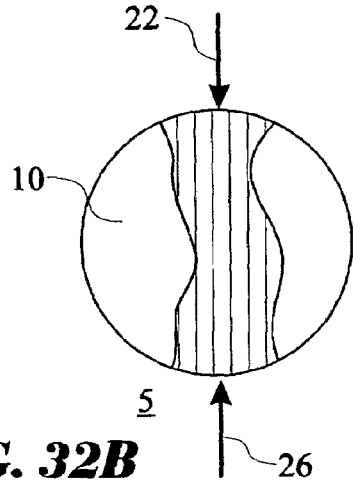
FIG. 32A  0.40 SN, IN  FIG. 32B
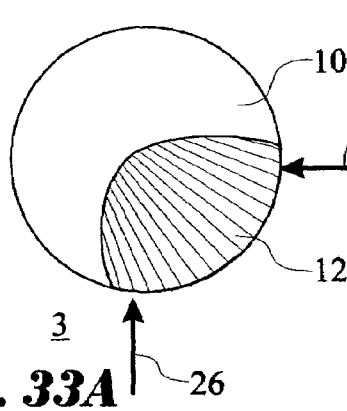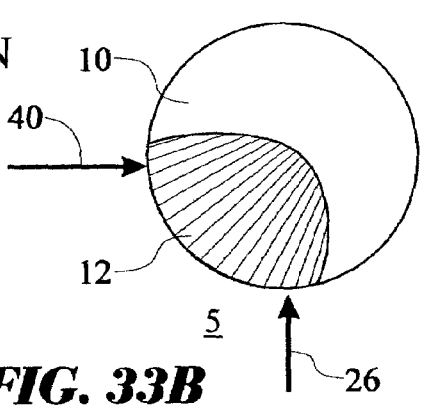
FIG. 33A  0.40 IN, NN  FIG. 33B
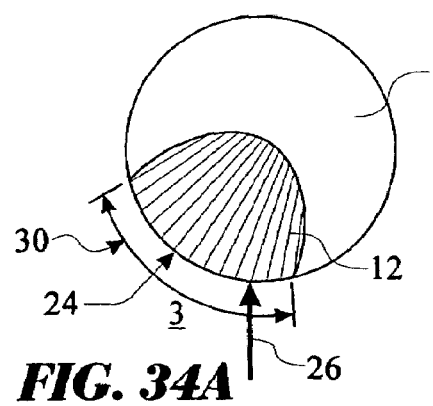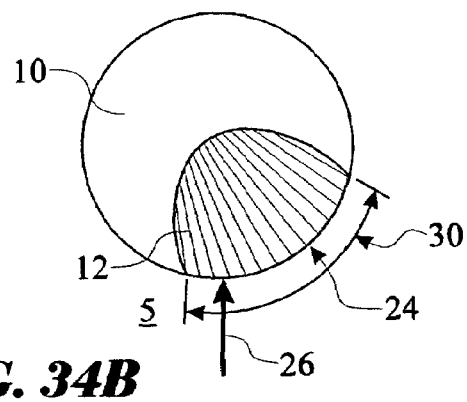
FIG. 34A  0.40 1+TS IN  FIG. 34B

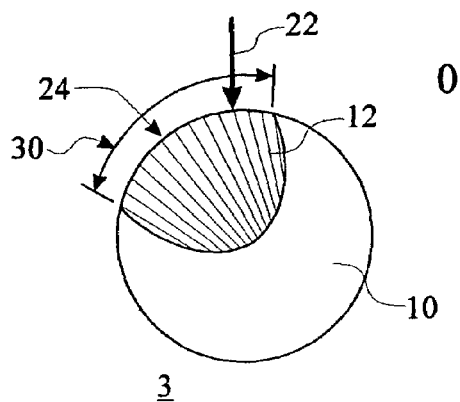
0.40 1+TS
SN
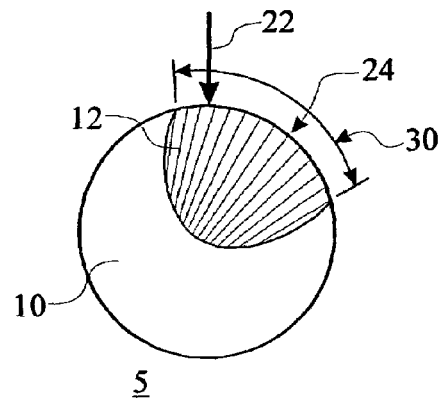
FIG. 35A  FIG. 35B
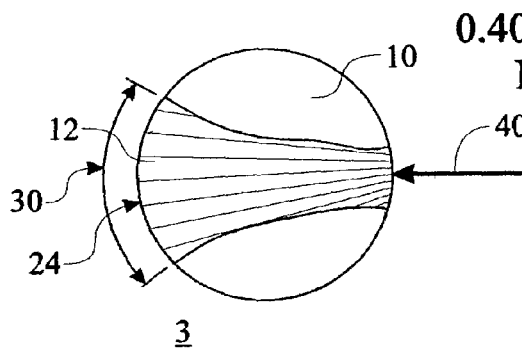
0.40 1+TS
NN
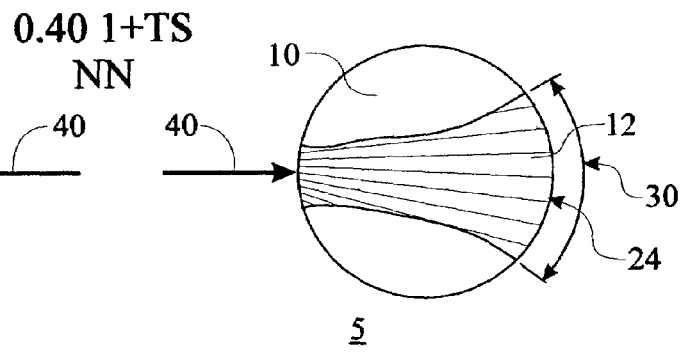
FIG. 36A  FIG. 36B
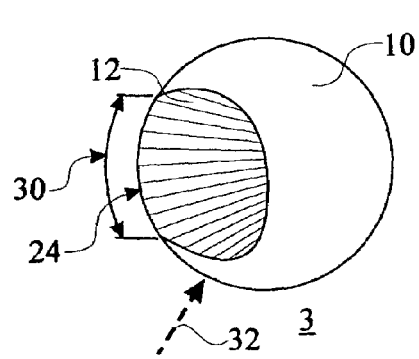
0.40 1+TS
IRT
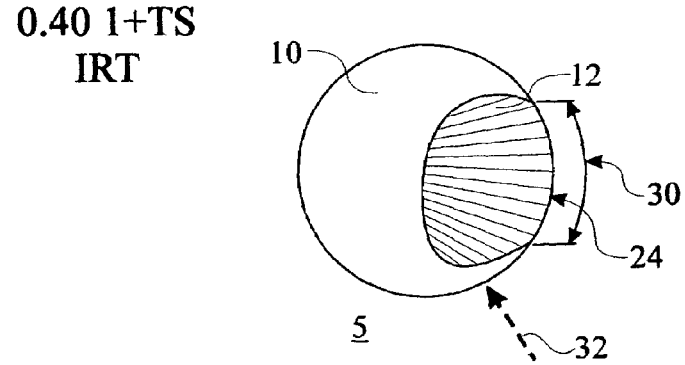
FIG. 37A  FIG. 37B

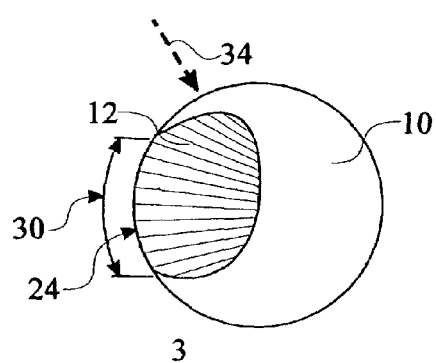
0.40 1+TS
SRT
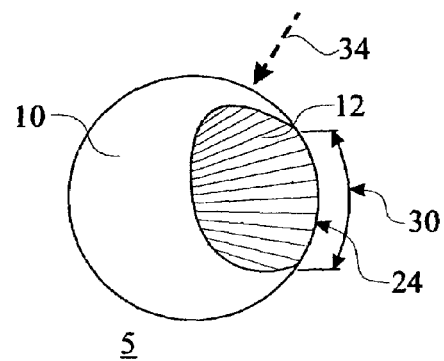
FIG. 38A     FIG. 38B
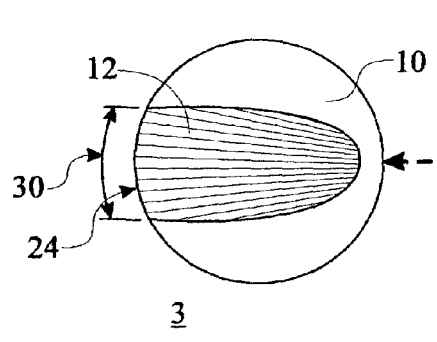
0.40 1+TS
NRT
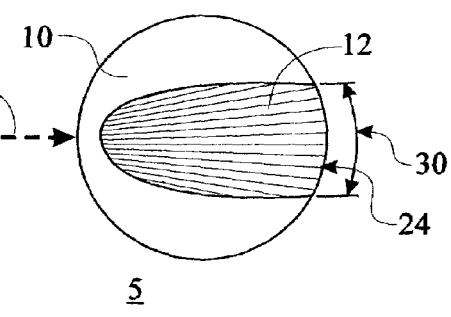
FIG. 39A     FIG. 39B

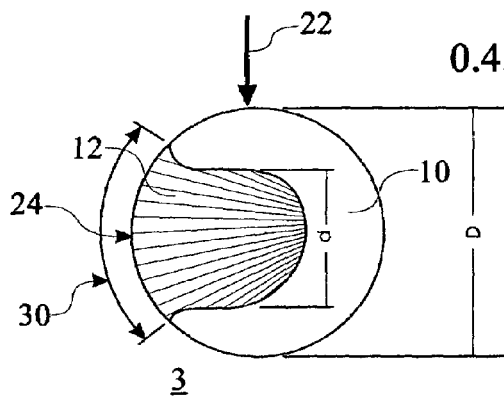
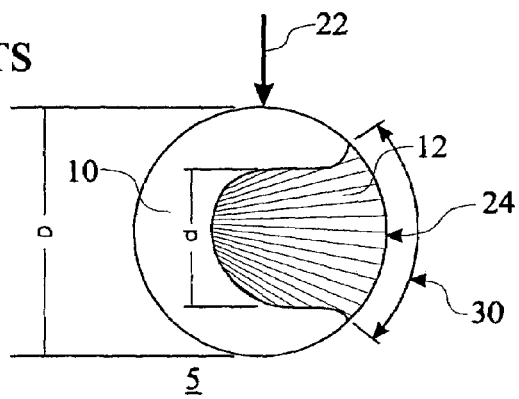
FIG. 40A     FIG. 40B
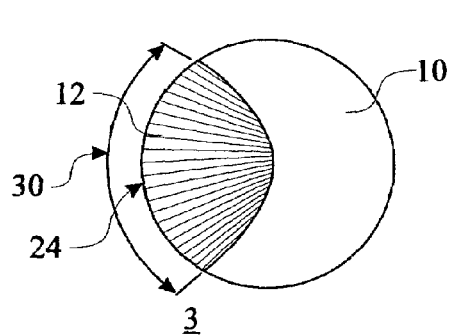
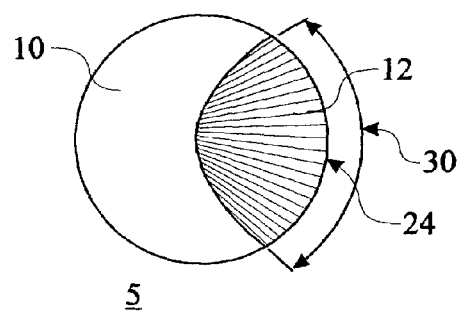
FIG. 41A     FIG. 41B
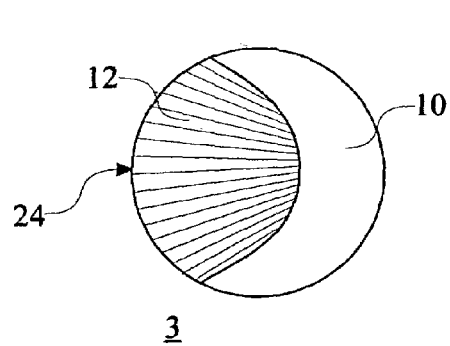
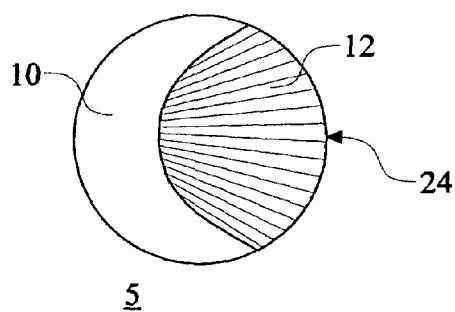
FIG. 42A     FIG. 42B

0.55 2+TS
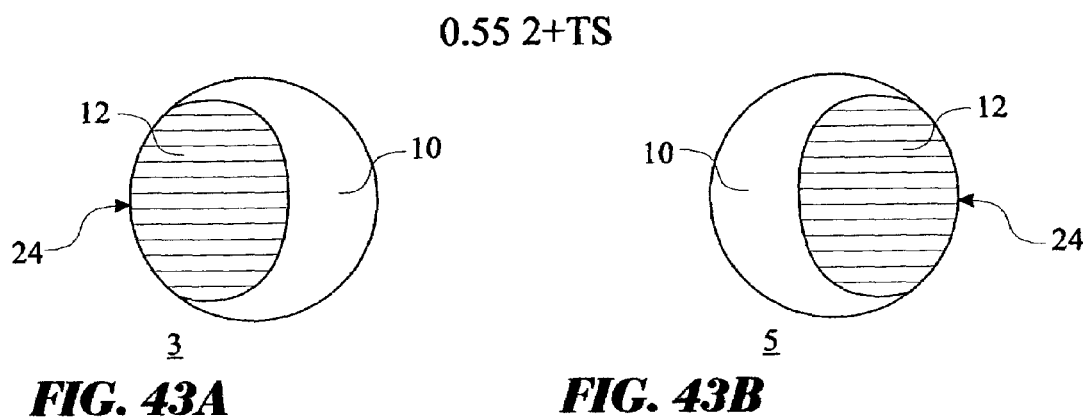
FIG. 43A  FIG. 43B
0.60 2+TS
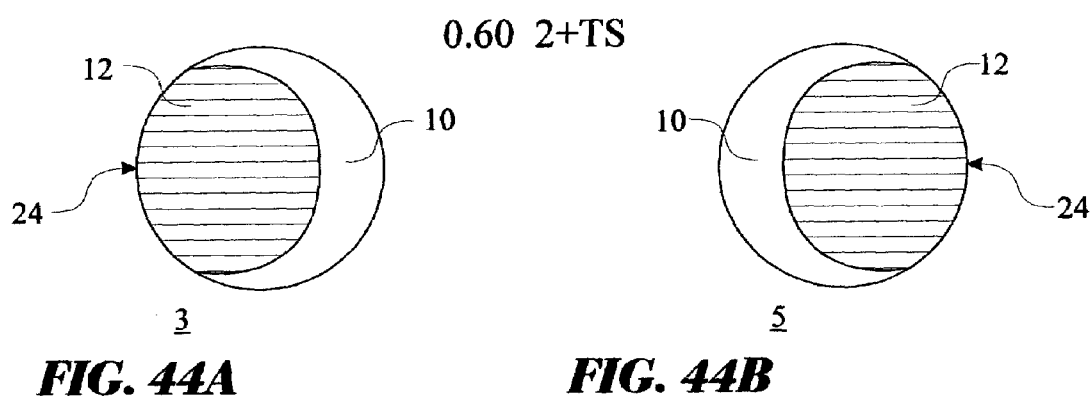
FIG. 44A  FIG. 44B
0.30 SN
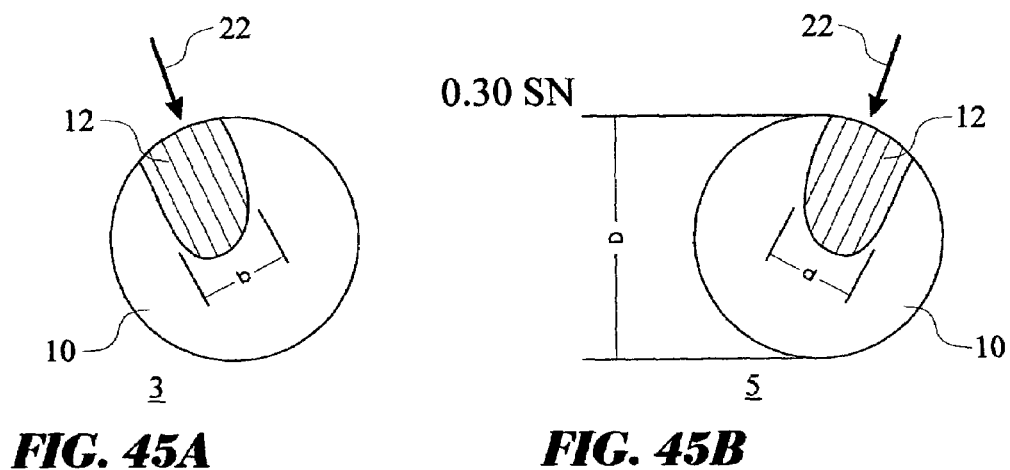
FIG. 45A  FIG. 45B

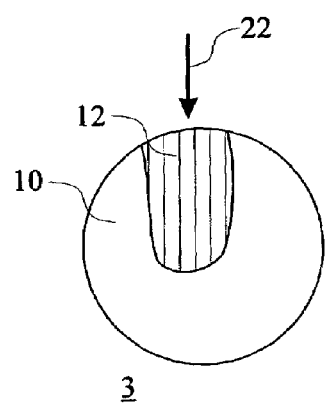
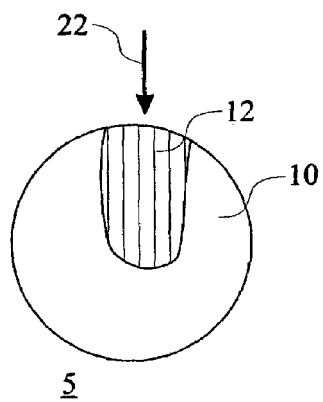
0.35 SN
FIG. 46A  FIG. 46B
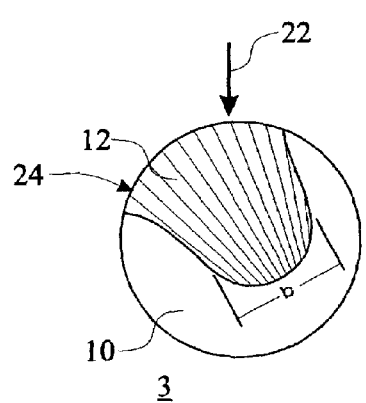
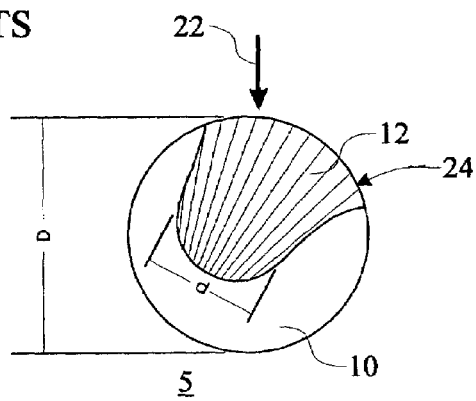
0.45 2+TS SN
FIG. 47A  FIG. 47B
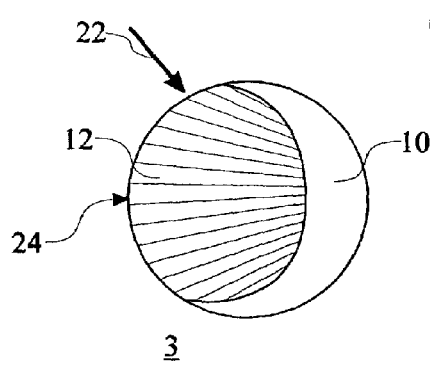
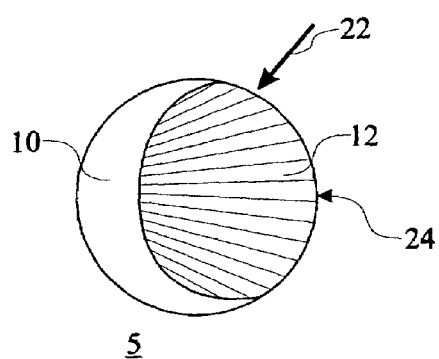
0.65 3+TS SN
FIG. 48A  FIG. 48B

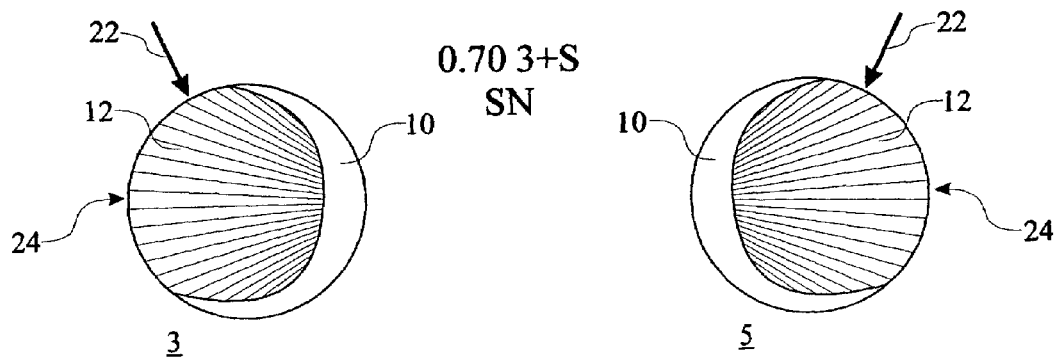
FIG. 49A     FIG. 49B
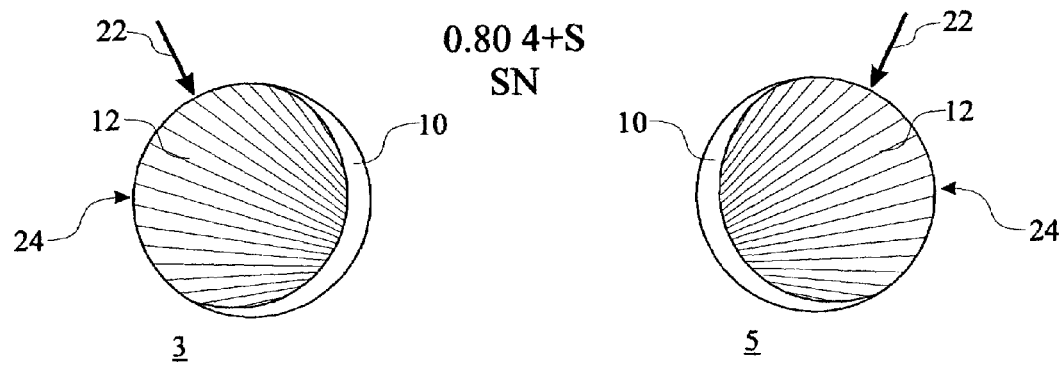
FIG. 50A     FIG. 50B
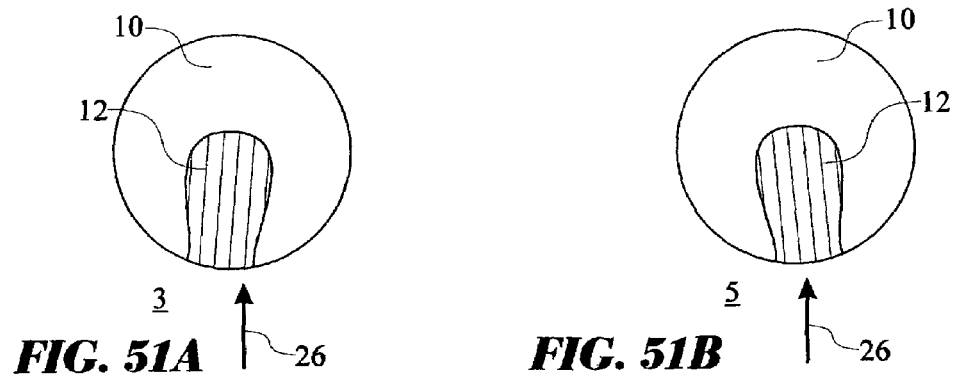
FIG. 51A     FIG. 51B

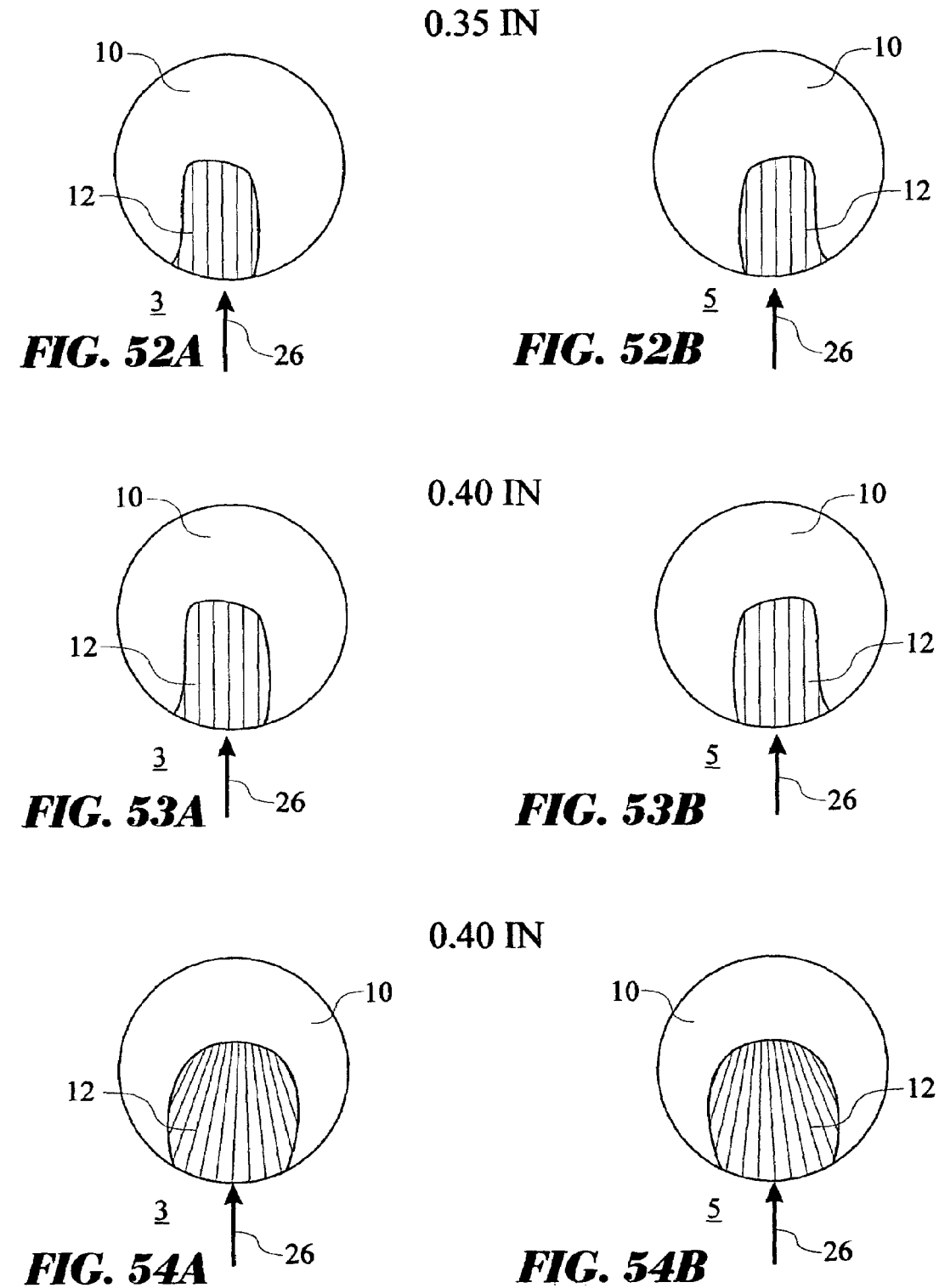

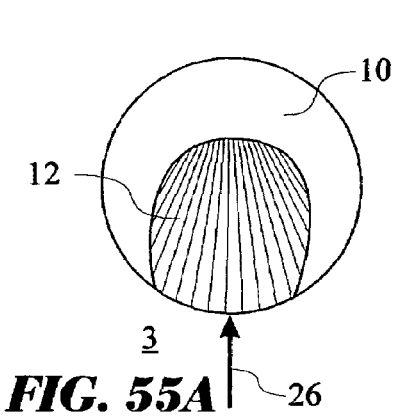
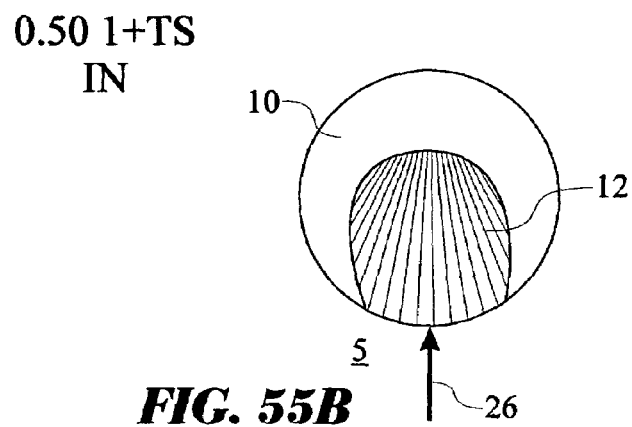
FIG. 55A  0.50 1+TS IN  FIG. 55B
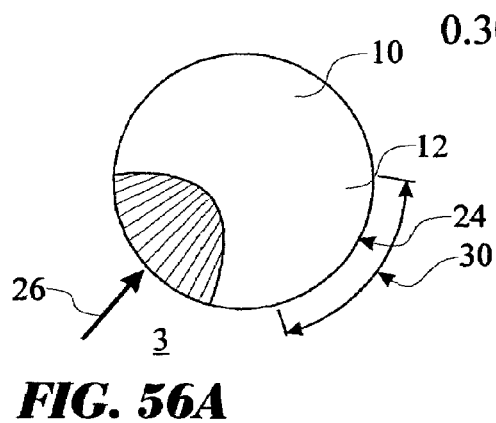
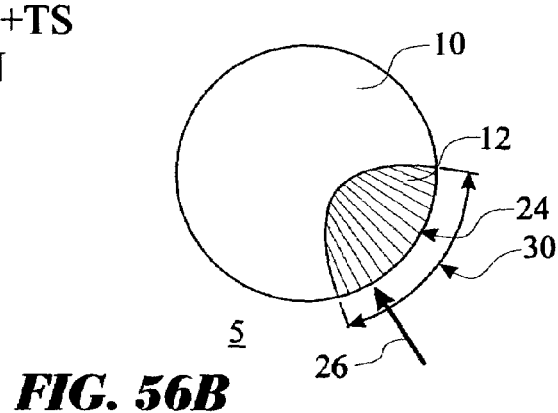
FIG. 56A  0.30 1+TS IN  FIG. 56B
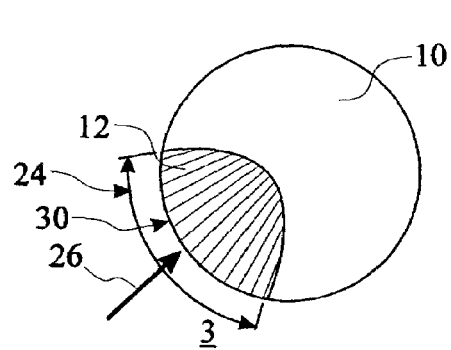
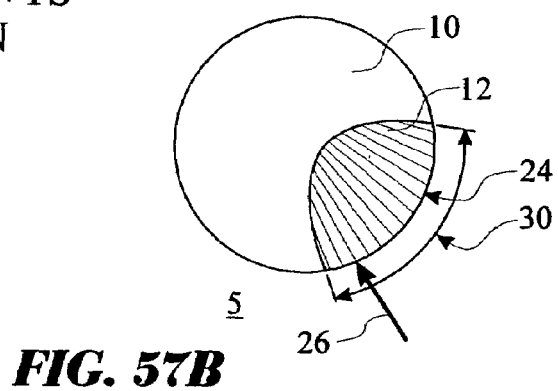
FIG. 57A  0.40 1+TS IN  FIG. 57B

0.55 2+TS
IN 0.60 2+TS
IN 0.65 2+TS
IN 0.55 2+TS
IN, SN 0.60 2+TS
IN, SN 0.65 2+TS
IN, SN 0.70 3+TS
IN, SN 0.75 3+TS
IN, SN 0.80 4+TS
IN, SN 0.65 2+TS
SRT 0.70 3+TS
SRT, IRT 0.70 3+TS
IN, SRT 0.75 3+TS
IN, SRT 0.80 3+TS
IN, SRT 0.65 2+TS
IRT 0.75 3+TS
IRT, SRT 0.80 4+TS
IRT, SRT 0.80 4+TS
SN, IRT

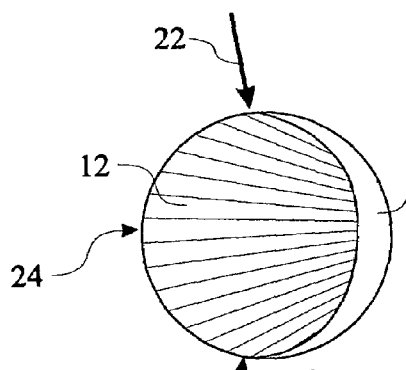
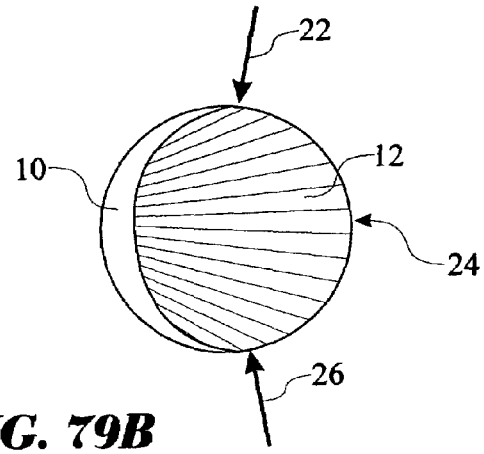
FIG. 79A  0.80 4+TS IN, SN  FIG. 79B
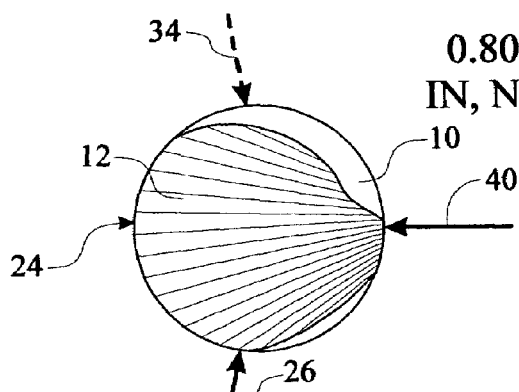
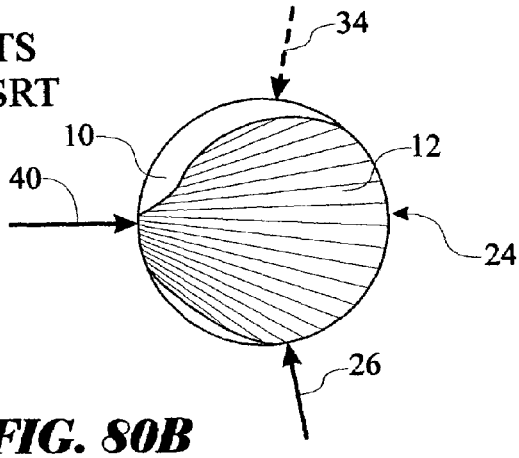
FIG. 80A  0.80 4+TS IN, NN, SRT  FIG. 80B
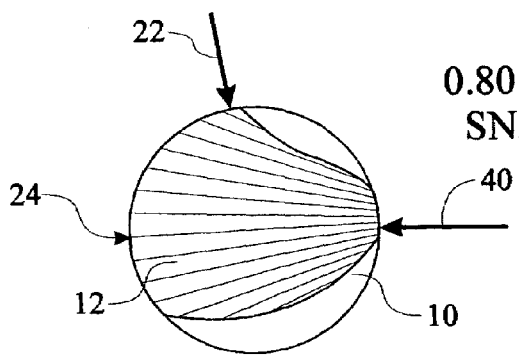
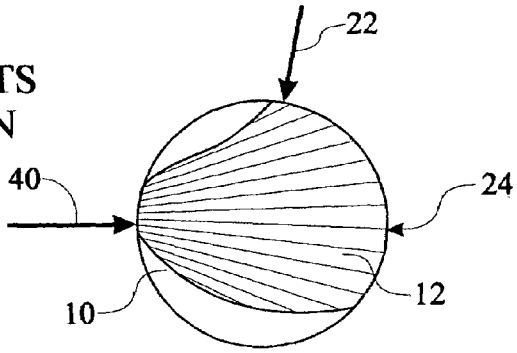
FIG. 81A  0.80 4+TS SN, NN  FIG. 81B

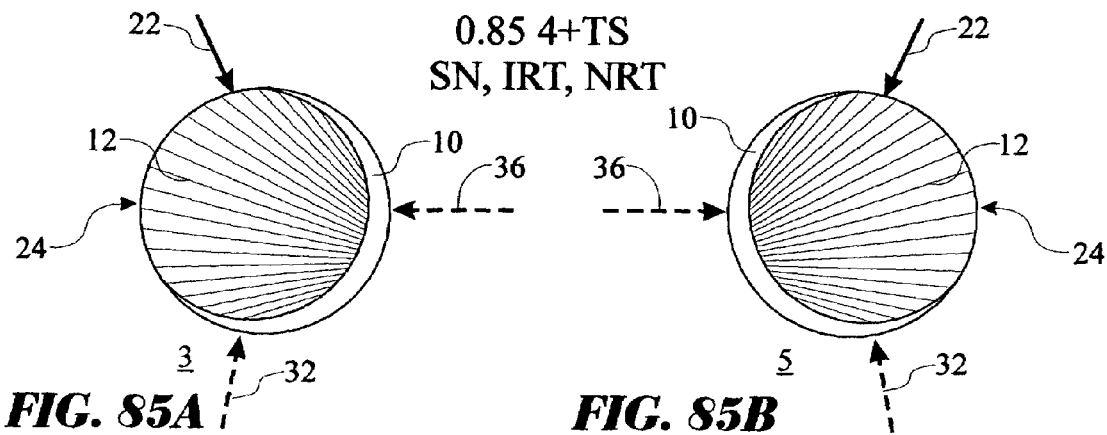
FIG. 85A  0.85 4+TS SN, IRT, NRT  FIG. 85B
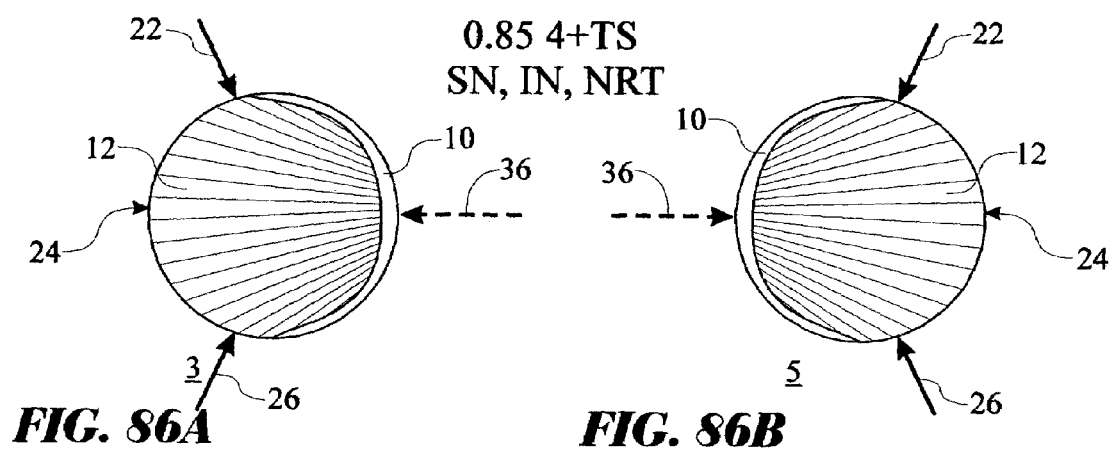
FIG. 86A  0.85 4+TS SN, IN, NRT  FIG. 86B
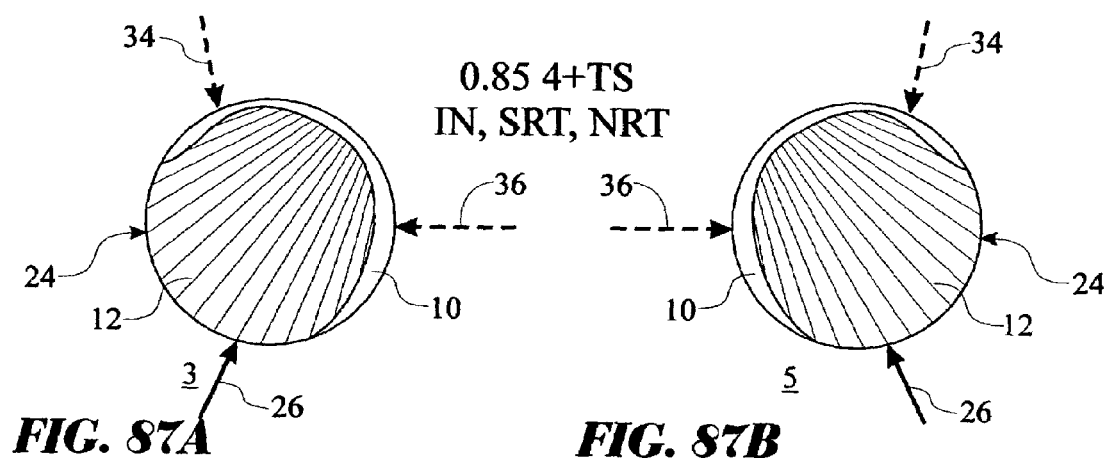
FIG. 87A  0.85 4+TS IN, SRT, NRT  FIG. 87B

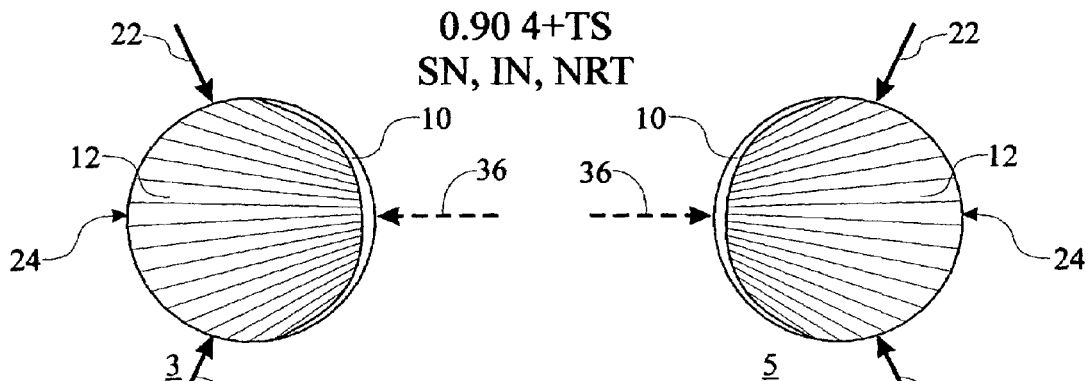
FIG. 88A   0.90 4+TS SN, IN, NRT   FIG. 88B
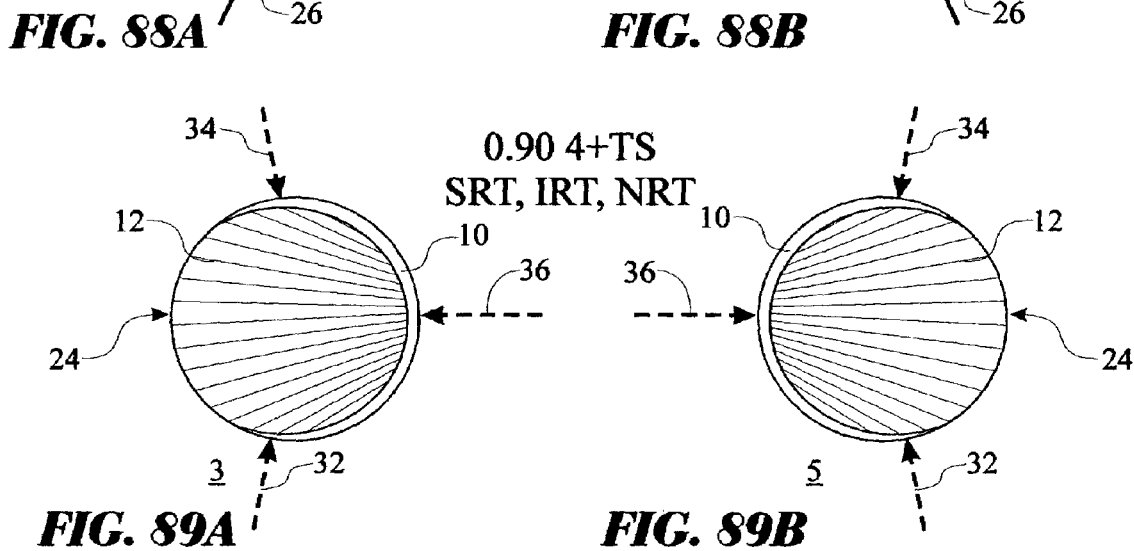
FIG. 89A   0.90 4+TS SRT, IRT, NRT   FIG. 89B
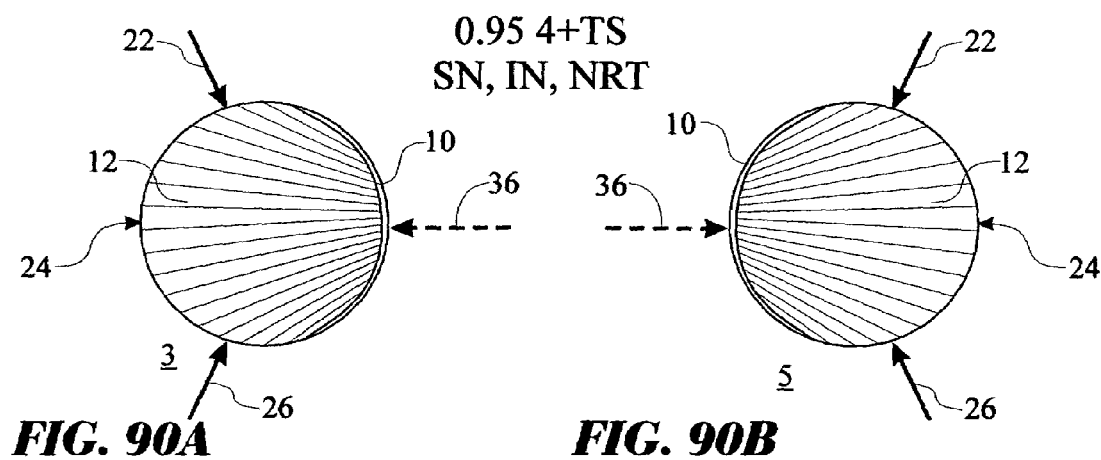
FIG. 90A   0.95 4+TS SN, IN, NRT   FIG. 90B

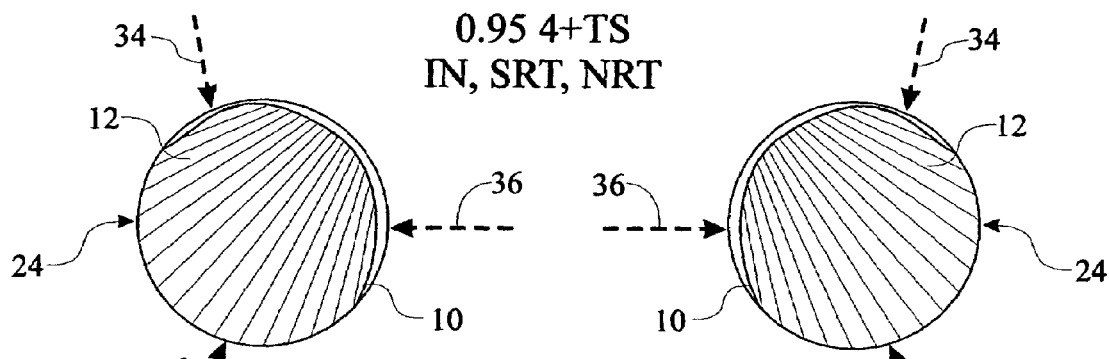
FIG. 91A  FIG. 91B
0.95 4+TS
IN, SRT, NRT
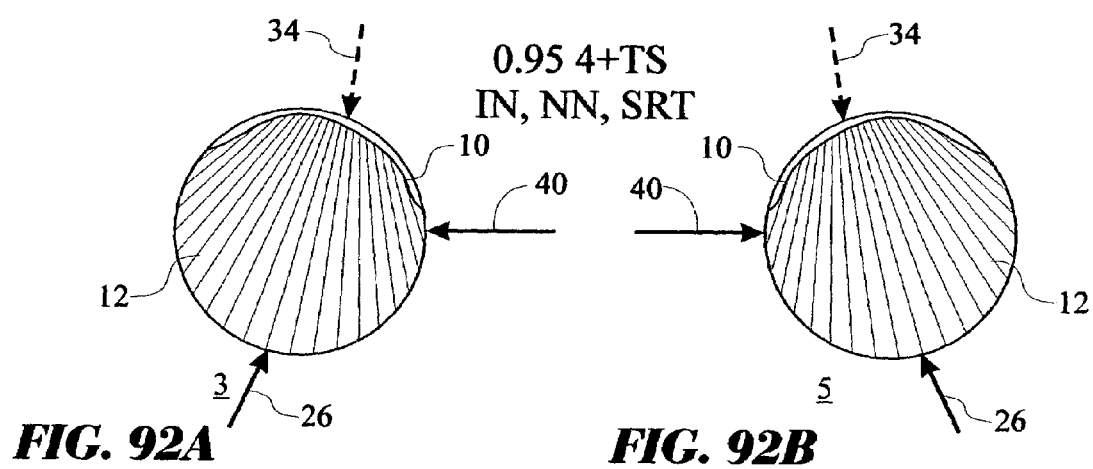
FIG. 92A  FIG. 92B
0.95 4+TS
IN, NN, SRT
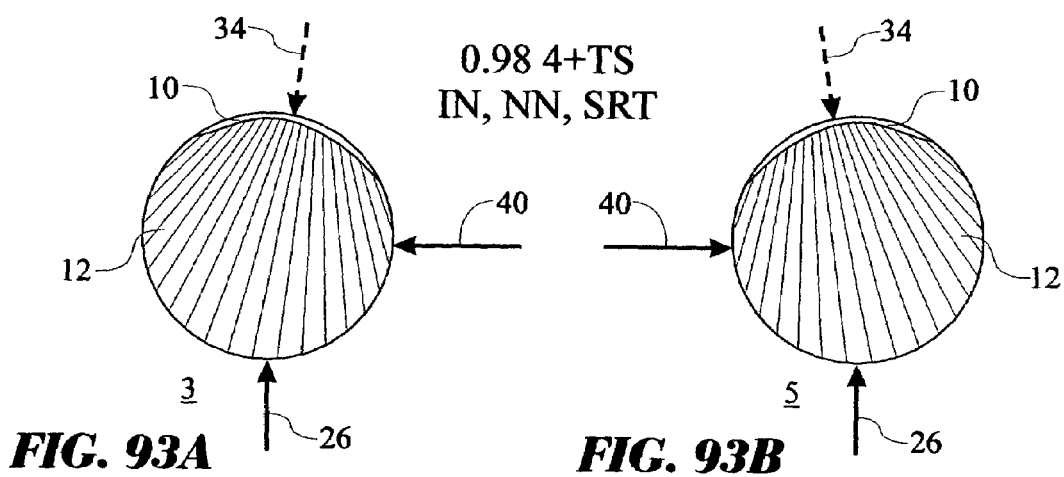
FIG. 93A  FIG. 93B
0.98 4+TS
IN, NN, SRT

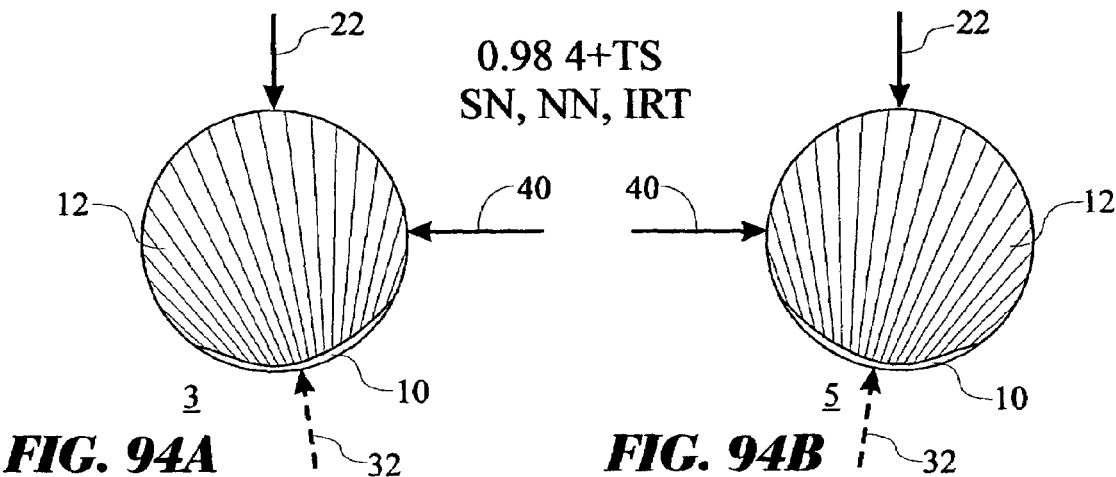
FIG. 94A FIG. 94B
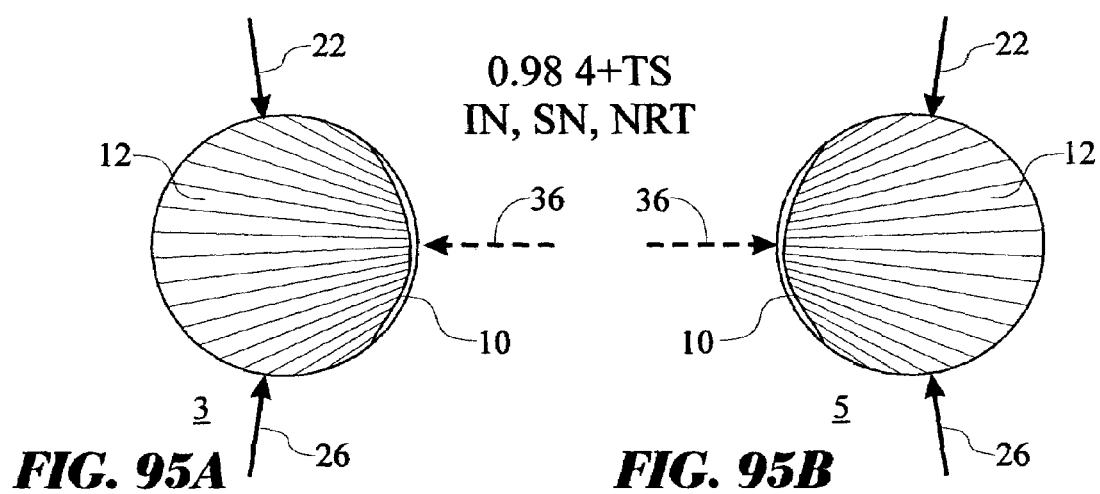
FIG. 95A FIG. 95B
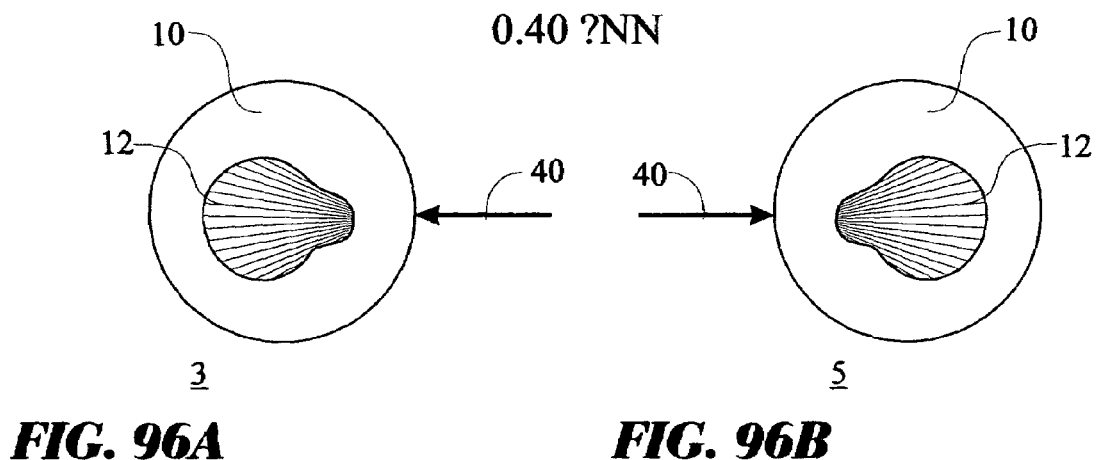
FIG. 96A FIG. 96B

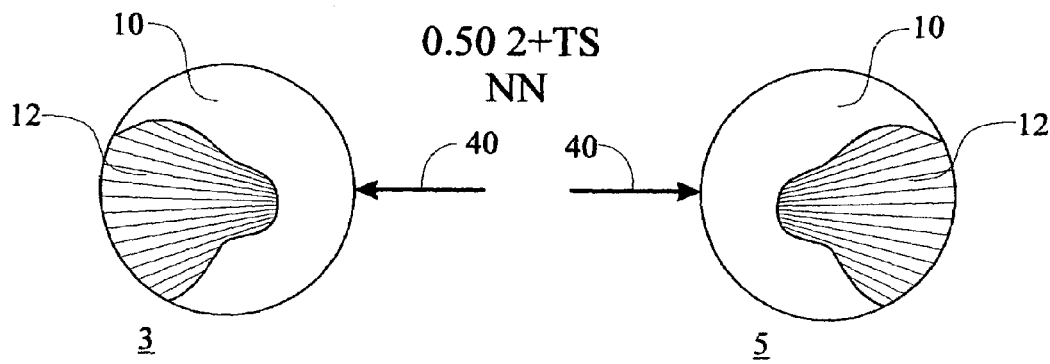
FIG. 97A  FIG. 97B
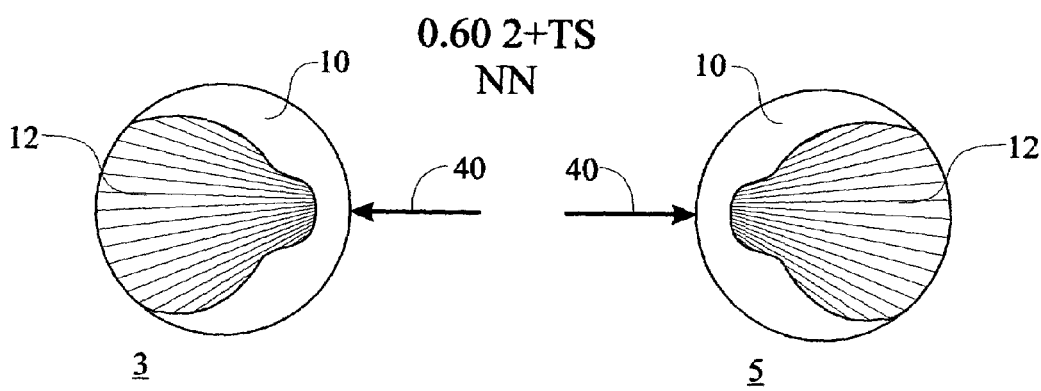
FIG. 98A  FIG. 98B
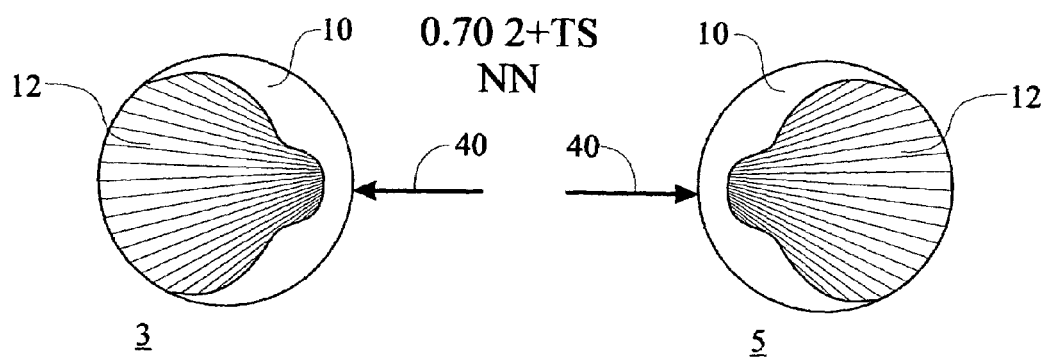
FIG. 99A  FIG. 99B

OPTIC NERVE DOCUMENTATION VIA ELECTRONIC MEDICAL RECORDS

FIELD OF THE INVENTION

The invention relates generally to electronic medical records, more specifically, a computer software process for documenting the appearance/change in appearance of a patient's optic nerve.

BACKGROUND OF THE INVENTION

The optic nerve is the part of the eye that carries visual information from the eye to the brain. The optic nerve is located at the very back of the eye just to the nose side of center. The optic nerve is the part of the eye that gets damaged when someone has glaucoma and many other ocular diseases.

The optic nerve comprising of approximately 1 million small individual thread-like nerve fibers which originates from the retina. The fibers bend about 90 degrees as they leave the retina and enter the front of the optic nerve (referred to as the optic nerve head). Normally, there is a small crater-like depression (referred to as the cup) seen at the front of the optic nerve head. In healthy eyes, the diameter of the cup is smaller than the diameter of the optic nerve. Many years ago, it was common practice for a doctor to look at the nerve using a monocular magnification device. The image of the nerve head would resemble a cup on a saucer (or disc), hence deriving a number of terms for describing the optic nerve. Such terms or descriptors include: cup to disc ratio (CDR); cupping; cupped; full rim; rim thinning; saucerization; notching, etc.).

It is critical to monitor the shape and health of the optic nerve. This is accomplished by maintaining records that describe the appearance and shape of the optic nerve. The normal cup to disc ratio (the diameter of the cup divided by the diameter of the whole nerve head or disc) is about ⅓ or 0.3. There is some normal variation here, with some patients having almost no cup (thus having ¹⁄₁₀ or 0.1), whereas others have as high as ⅗ths or 0.6 as a cup to disc ratio. If a patient has a cup/disc ratio larger than ⅓, then doctors get suspicious that the cup could be getting larger than it used to be, implying the progression of a disease process.

Glaucoma can cause the cup to enlarge (actually little nerve fibers are being wiped out along the rim of the optic nerve in glaucoma). Some doctors refer to an enlarged cup/disc ratio as cupping or a cupped nerve. Glaucoma typically causes the cup to get bigger in a vertical oval type pattern, initially. However, any change in the optic nerve can be an early sign of glaucoma.

To differentiate whether a large cup is normal or glaucomatous requires the doctor to pay close attention to the rim of the nerve. Photos and other analysis of the optic nerve are extremely valuable for documentation of the nerve shape and for future comparisons. If the temporal rim of the optic nerve is very thin sloped or notched, then glaucoma is more likely and may be diagnosed.

The doctor also pays close attention to the color of the optic nerve because some other diseases of the optic nerve can cause enlarged cups but also cause the nerve to look pale (multiple sclerosis, brain tumors, strokes, etc.).

One can take and record an image (i.e. photo) and store such image. Providing such image is limiting in that a photo does not clearly describe and identify information. A photo requires greater memory for storage.

What is desirable is a method that provides Doctors with the ability to maintain illustrated documentation and history of a patient's optic nerve.

SUMMARY OF THE INVENTION

Accordingly the present invention teaches a method and apparatus for providing, storing, and maintaining electronic medical records, wherein said electronic medical records are electronic images or representations of a patient's optic nerves.

A first aspect to the present invention is defining and presenting the terminology respective to the various features used when describing a specific optic nerve.

In accordance with a first aspect, the following terminology is used to define the features of the optic nerve:

Ocular Dexter (OD): The patient's right eye.

Ocular Sinister (OS): The patient's left eye.

Optic Nerve/Optic Disc/Disc: The entire nerve utilized for vision. The optic nerve is the outer circle that will be illustrated throughout the specification.

Cup: The cup is the internal portion that represents lost optic nerve fibers that will be illustrated throughout the specification.

Cup to Disc Ratio (CDR): The cup to disc ratio can be described by a number (or several numbers) that refers to the ratio of the area of the cup to the area of the disc. The CDR is an industry standard for documenting the health of a patient's optic nerve. Details will be presented within the specification.

Full Rim (FR): Full rim is defined wherein the perimeter of the cup is completely within the perimeter of the optic nerve, and typically having a CDR of 0.5-0.6.

Saucerization: Saucerization is defined as the sloping excavation of the optic nerve. Saucerization is presented in conjunction with a grading or amount of saucerization. Generally, the saucerization is graded between 1+ and 4+, respective to the level of severity. The grading scale is 1+ being the least or mild and 4+ being an advanced or severe condition. Details will be presented within the specification.

Temporal Saucerization (TS): Temporal saucerization is defined as the sloping excavation of the outer or temporal (towards the ear) side of the optic nerve.

Nasal Saucerization (NS): Nasal saucerization is defined as the sloping excavation of the inner or nasal (towards the nose) side of the optic nerve.

Mild Temporal Saucerization (MTS): Mild temporal saucerization is defined as saucerization that is very minor sloping excavation of the outer or temporal (towards the ear) side of the optic nerve.

Mild Nasal Saucerization (MNS): Mild nasal saucerization is defined as saucerization that is very minor sloping excavation of the inner or nasal (towards the nose) side of the optic nerve.

Superior Rim Thinning (SRT): Superior rim thinning is defined as thinning, an apparent or possible change in the optic nerve that indicates loss of optic nerve tissue on the superior (towards the eyebrow) aspect of the nerve.

Inferior Rim Thinning (IRT): Inferior rim thinning is defined as thinning, an apparent or possible change in the optic nerve that indicates loss of optic nerve tissue on the inferior (towards the chin) aspect of the nerve.

Temporal Rim Thinning (TRT): Temporal rim thinning is defined as thinning, an apparent or possible change in the optic nerve that indicates loss of optic nerve tissue on the temporal (towards the ear) aspect of the nerve.

Nasal Rim Thinning (NRT): Nasal rim thinning is defined as thinning, an apparent or possible change in the optic nerve that indicates loss of optic nerve tissue on the nasal (towards the nose) aspect of the nerve.

Diffuse Rim Thinning (DRT): Diffuse rim thinning is defined as thinning, an apparent or possible change in the optic nerve that indicates loss of optic nerve tissue 360 degrees about the optic nerve.

A second aspect of the present invention is to provide electronic medical record software.

A third aspect of the present invention is to provide an electronic medical record software, more specifically said electronic medical record software is to record illustrations representative of a patient's optic nerve.

A fourth aspect of the present invention is to provide an electronic medical record software, more specifically said electronic medical record software is to record illustrations representative of a patient's optic nerve for each of patient's two eyes.

A fifth aspect of the present invention is to provide a graphical user interface (GUI); wherein said GUI provides a simplistic means for entering information.

A sixth aspect of the present invention is to provide a graphical user interface (GUI); wherein said GUI provides entry to specific key features.

A seventh aspect of the present invention is to provide a graphical user interface (GUI); wherein said GUI provides entry to specific key features, wherein said features comprise those of an optic nerve.

An eighth aspect of the present invention provides a graphical user interface (GUI), wherein said GUI provides entry to specific key features, wherein said features comprise those of an optic nerve, including:
   a. Cup to Disc ratio (CDR)
   b. Cup Position relative to Disc
      i. Full Rim & Variations of Full Rim Conditions
         1. Cup Shape
            a. Inferior Rim Thinning
            b. Superior Rim Thinning
            c. Temporal Thinning
      ii. Saucerization (Enter grading)
         1. Temporal Saucerization
         2. Nasal Saucerization
         3. Superior Notch
         4. Inferior Notch A ninth aspect of the present invention provides a graphical user interface (GUI); wherein said GUI provides entry to specific key features, wherein said GUI entry is accomplished my entering data.

A tenth aspect of the present invention provides a graphical user interface (GUI); wherein said GUI provides entry to specific key features, wherein said GUI entry is accomplished by selecting from examples.

An eleventh aspect of the present invention provides a graphical user interface (GUI); wherein said GUI provides entry to specific key features, wherein said GUI entry is accomplished by selecting from examples respective to each feature.

A twelfth aspect of the present invention selects a graphical representation of the patient's optic nerve from an index of pre-established graphical images, wherein said pre-established graphical images are categorized by key feature types.

A thirteenth aspect of the present invention selects a graphical representation of the patient's optic nerve from an index of pre-established graphical images based upon the user's input(s).

A fourteenth aspect of the present invention selects a graphical representation of the patient's optic nerve from an index of pre-established graphical images based upon the users input(s), wherein the user selects from a presentation of a series of representative images, each series representative of a specific classification of key features, and ultimately narrowing down to a final, single representative image.

A fifteenth aspect of the present invention generates a graphical representation of the patients optic nerve based upon the user's input(s).

A sixteenth aspect of the present invention generates a graphical representation of the patient's optic nerve based upon the user's input(s), presenting said graphical representation (as it is generated) as the user proceeds through the various input steps.

A seventeenth aspect of the present invention generates a graphical representation of the patient's optic nerve based upon the user's input(s), wherein the user's inputs can comprise drawing a representation of the optic nerve.

An eighteenth aspect of the present invention provides the user the ability to view a history of graphical images respective to the patient.

A nineteenth aspect of the present invention provides the user the ability to view a history of graphical images respective to the patient, wherein the user can further view the images in an animated manner further presenting the recorded changes to the patient's optic nerve over time.

A twentieth aspect of the present invention comprising a computer, a user interface, a storage media, and software respective to the present invention disclosed herein.

A twenty-first aspect of the present invention comprising uploading an actual image of said optic nerve into the patient's file.

A twenty-second aspect of the present invention comprising uploading an actual image of said optic nerve into the patient's file, wherein then utilizing the uploaded image to create an illustration of said optic nerve.

A twenty-third aspect of the present invention comprising a presentation that is representative of the optic nerve and further comprising specific respective information.

A twenty-fourth aspect of the present invention comprising the ability to utilize an uploaded image of a patient's optic nerve to generate a graphical representation of the patient's optic nerve.

A twenty-fifth aspect of the present invention comprising the ability to generate a graphical representation of the patient's optic nerve using an animated illustration and allowing the user to make adjustments using a user interface. Such user interfaces can comprise a mouse, a tablet, a pointer, a touch screen, and the like.

A twenty-sixth aspect of the present invention comprising the ability to aid in determining the health of a patient's optic nerve.

A twenty-seventh aspect of the present invention comprising the ability to aid in determining the health of a patient's optic nerve, wherein such means comprising recognition of changing trends of the patient's optic nerve.

A twenty-eighth aspect of the present invention comprising the ability to aid in determining the health of a patient's optic nerve, wherein such means comprising recognition of distinguishing features of the patient's optic nerve, said distinguishing features are known concerns for degeneration of said optic nerve.

A twenty-ninth aspect of the present invention comprising the ability to animate the history of a patient's optic nerve and optionally anticipate the potential progression of degeneration of the optic nerve based upon recorded history and time.

A thirtieth aspect of the present invention comprising the ability to generate a graphical representation of the patient's optic nerve via entry of respective feature information.

A thirty-first aspect of the present invention comprising the ability to generate a graphical representation of the patients optic nerve via viewing and selection from an index of various features of an optic nerve.

A thirty-second aspect of the present invention comprising the ability to store back up data files at a remote location to avoid catastrophic loss of vital patient information.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention/ where like designations denote like elements, and in which.

Figure 3A:
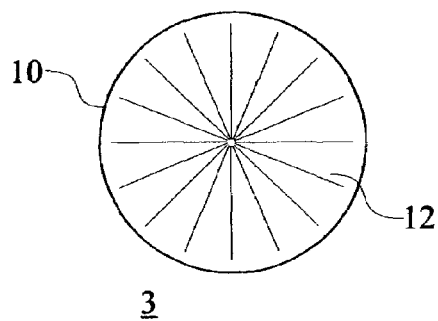
Figure 3B:
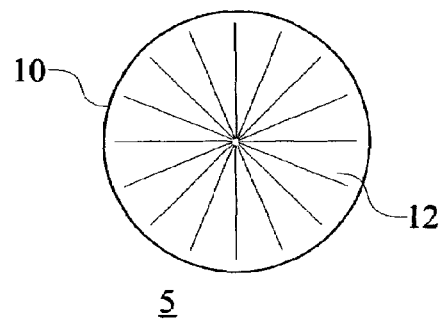
Figure 4A:
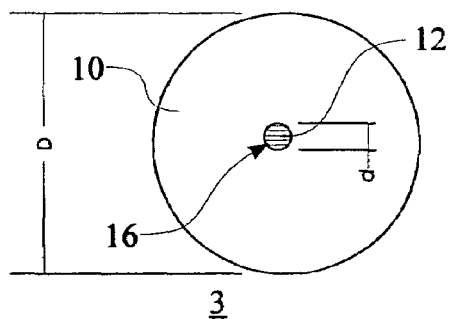
Figure 4B:
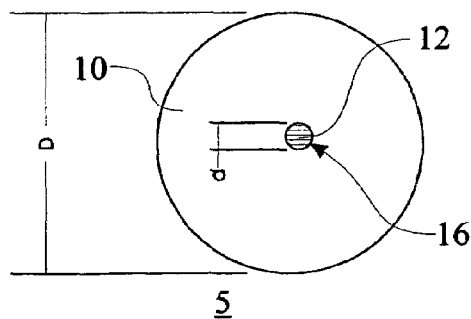
Figure 5A:
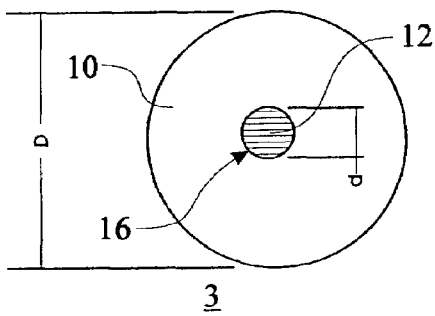
Figure 5B:
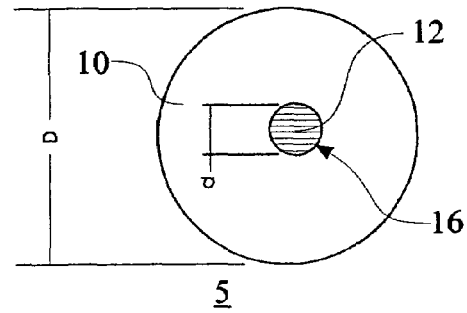
Figure 6A:
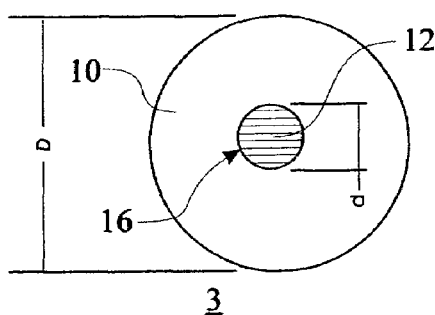
Figure 6B:
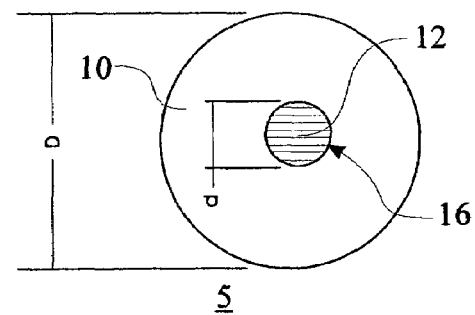
Figure 7A:
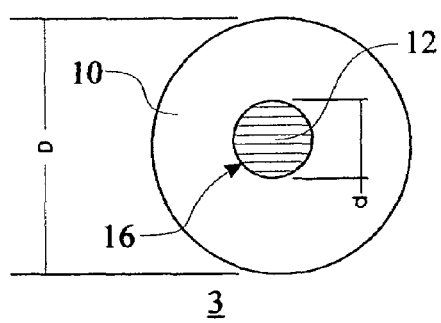
Figure 7B:
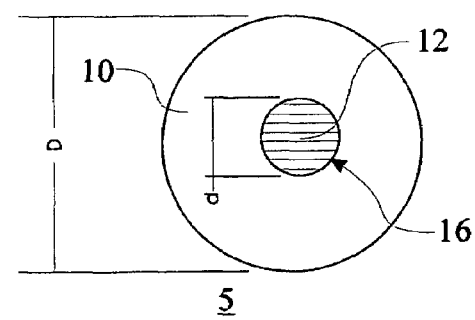

The following FIGS. (3-100) comprise an A and a B version for clarity and distinction, wherein said A is representative of a patient's Ocular Dexter (OD) (Right eye) and said B is representative of a patient's Ocular Sinister (OS) (Left eye). The orientation is shown as would be charted; as the Doctor is looking into a Patient's eyes;

FIG. 3 is an illustration representing an optic nerve described as having total rim loss (TRL);

FIG. 4 is an illustration representing an optic nerve described as 0.10 cup to disc ratio (CDR) and introducing a full rim;

FIG. 5 is an illustration representing an optic nerve described as 0.20 cup to disc ratio (CDR) and introducing a full rim;

FIG. 6 is an illustration representing an optic nerve described as 0.25 cup to disc ratio (CDR) and introducing a full rim;

FIG. 7 is an illustration representing an optic nerve described as 0.30 cup to disc ratio (CDR) and introducing a full rim;

FIG. 8 is an illustration representing an optic nerve described as 0.35 cup to disc ratio (CDR) and said full rim;

FIG. 9 is an illustration representing an optic nerve described as 0.40 cup to disc ratio (CDR) and said full rim;

FIG. 10 is an illustration representing an optic nerve described as 0.45 cup to disc ratio (CDR) with said full rim;

FIG. 11 is an illustration representing an optic nerve described as 0.50 cup to disc ratio (CDR) with said full rim;

FIG. 12 is an illustration representing an optic nerve described as 0.55 cup to disc ratio (CDR) introducing temporal rim thinning (TRT). Having a CDR of 0.55 to 0.60 places the optic nerve into a condition between having a full rim and a condition with at least some rim thinning. This illustration introduces temporal rim thinning, whereby other rim thinning could alternately be diagnosed in other conditions where the optic nerve disc is ofuset in another quadrant of the optic nerve disc;

FIG. 13 is an illustration representing an optic nerve described as 0.60 cup to disc ratio (CDR) with said temporal rim thinning (TR. It is noted that any optic nerve comprising a CDR greater than 0.60 would further comprise some form of thinning, and should be documented as such.

Figure 14A:
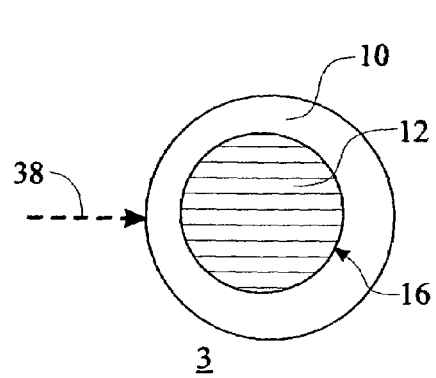
Figure 14B:
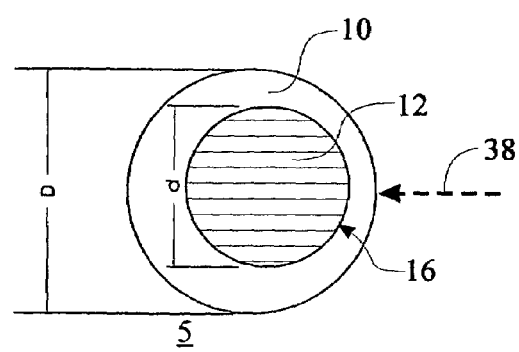
Figure 15A:
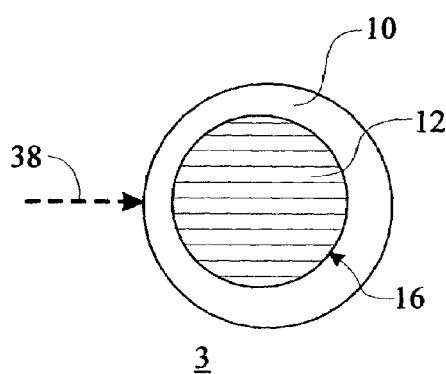
Figure 15B:
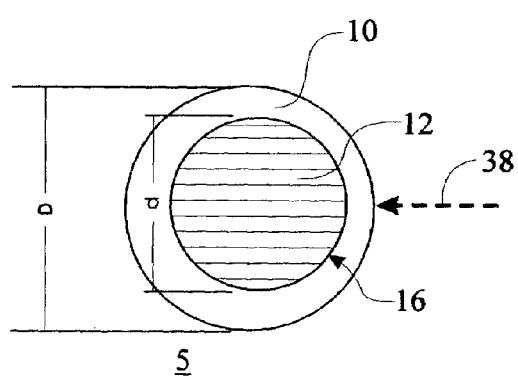
Figure 16A:
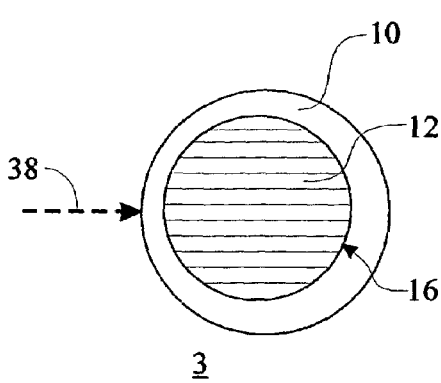
Figure 16B:
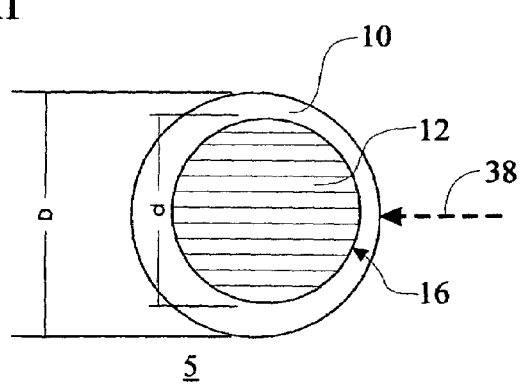
Figure 17A:
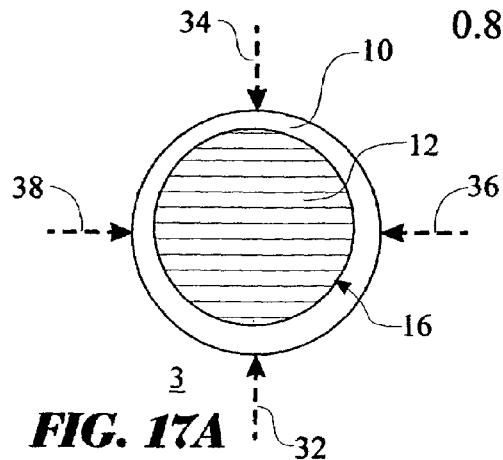
Figure 17B:
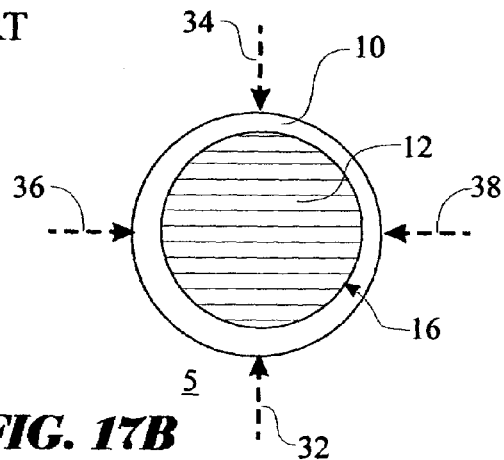
Figure 18A:
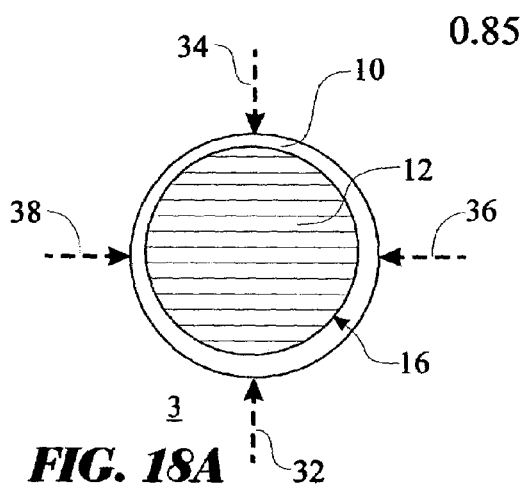
Figure 18B:
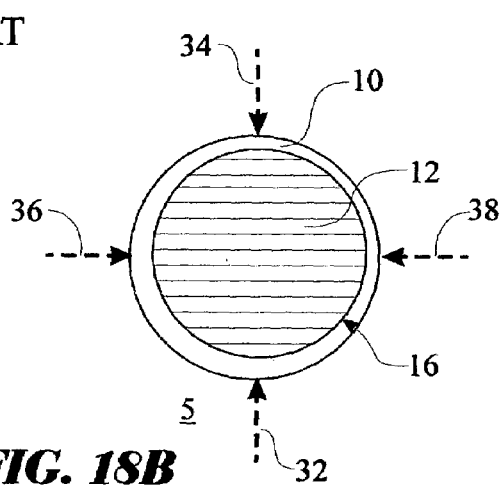
Figure 19A:
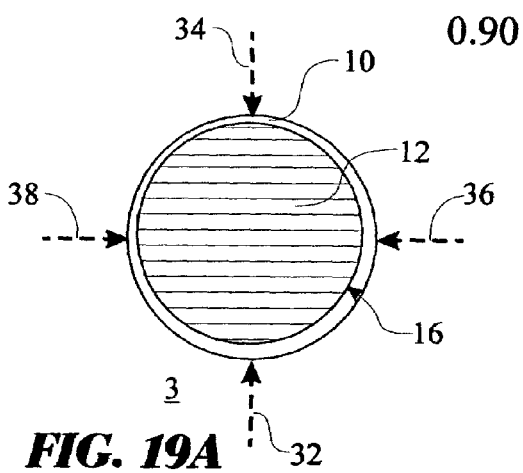
Figure 19B:
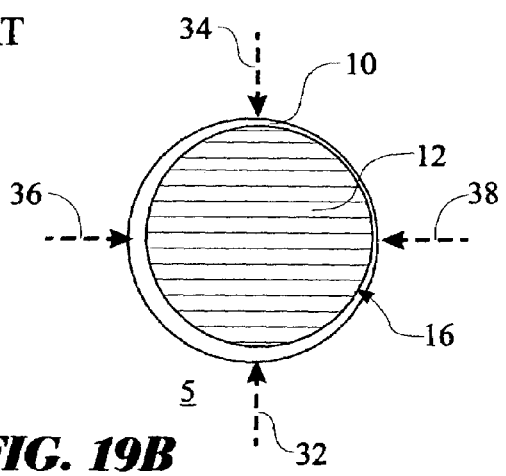
Figure 26A:
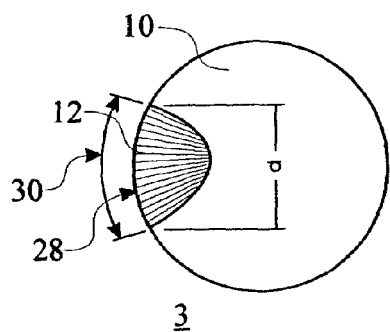
Figure 26B:
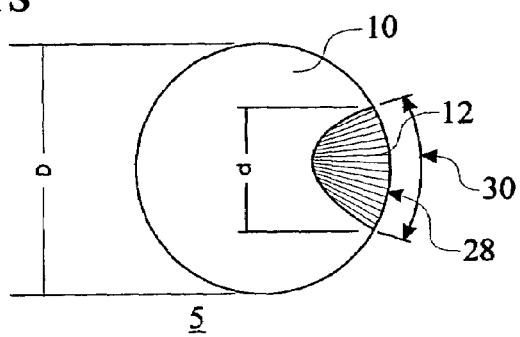
Figure 27A:
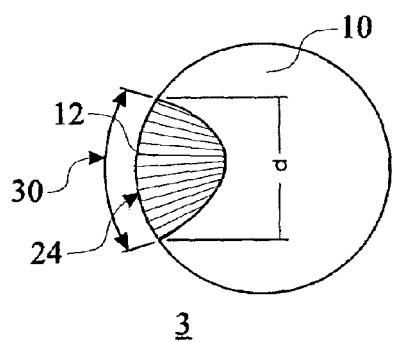
Figure 27B:
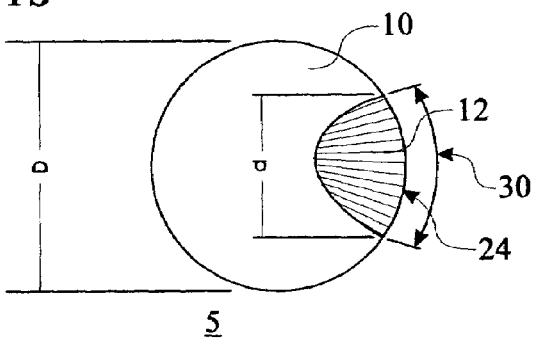
Figure 28A:
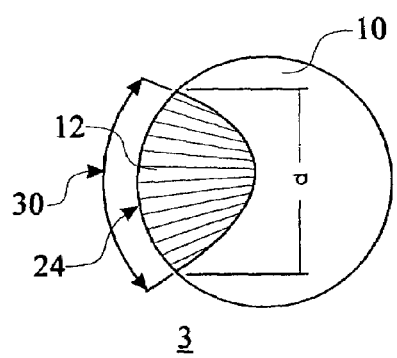
Figure 28B:
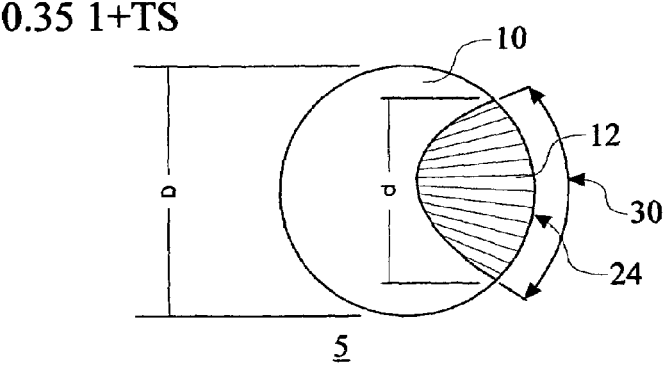
Figure 29A:
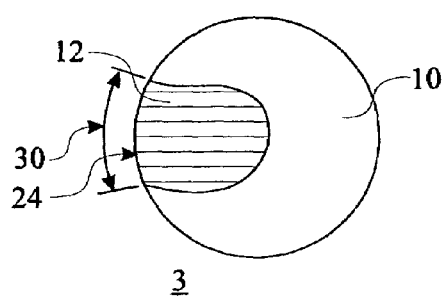
Figure 29B:
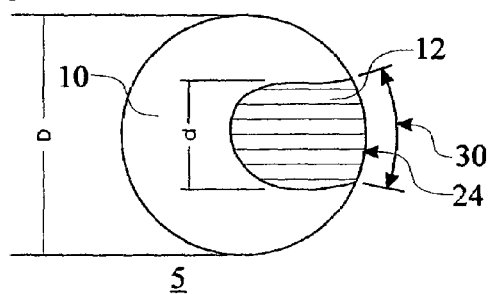
Figure 30A:
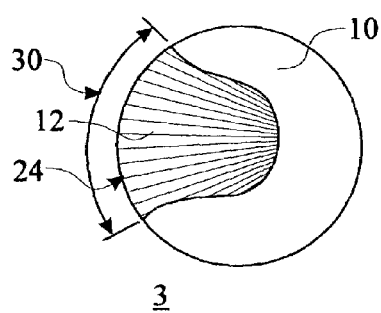
Figure 30B:
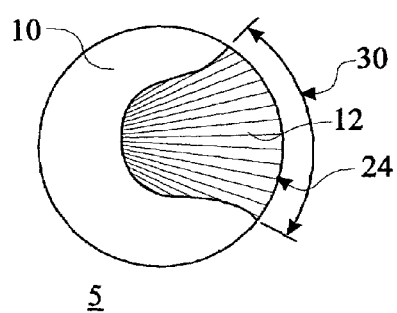
Figure 31A:
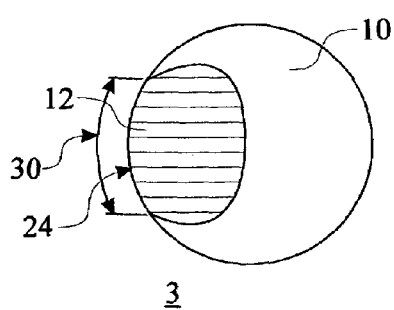
Figure 31B:
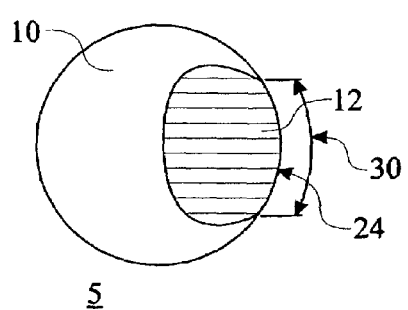
Figure 58A:
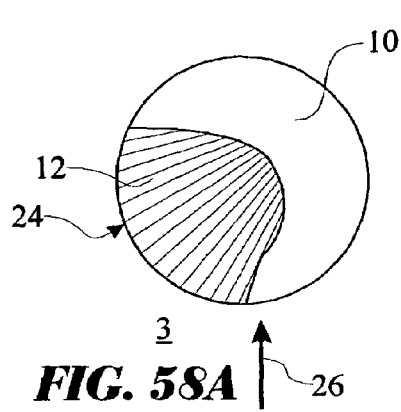
Figure 58B:
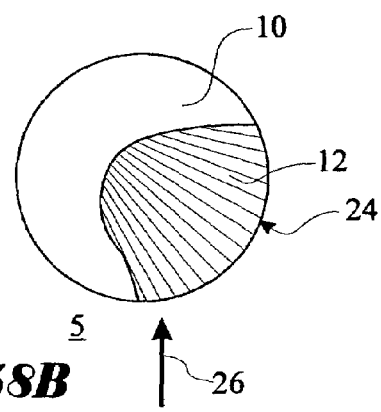
Figure 59A:
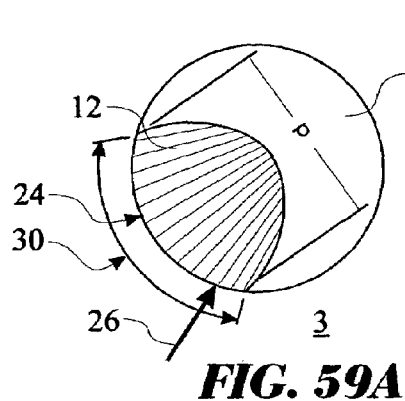
Figure 59B:
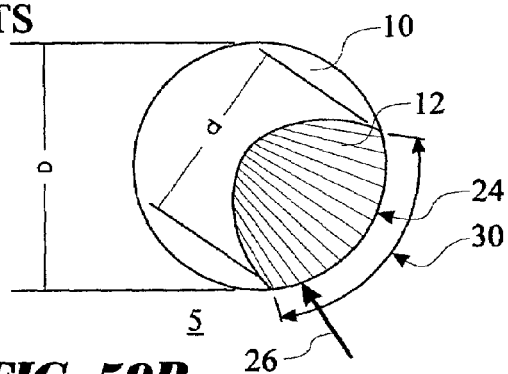
Figure 60A:
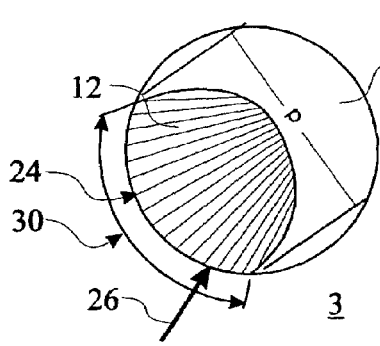
Figure 60B:
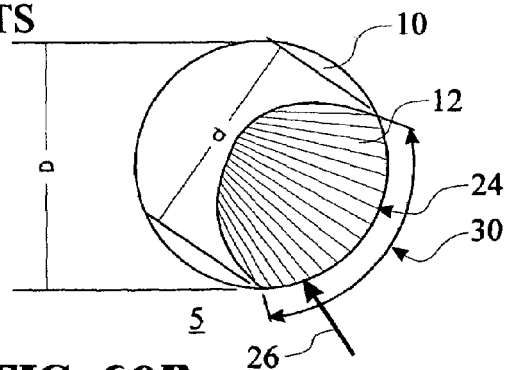
Figure 61A:
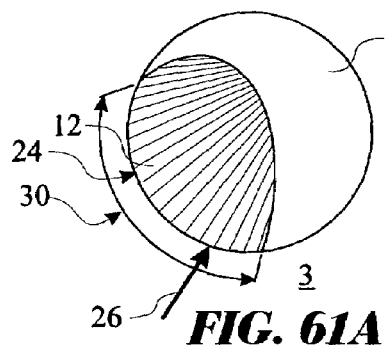
Figure 61B:
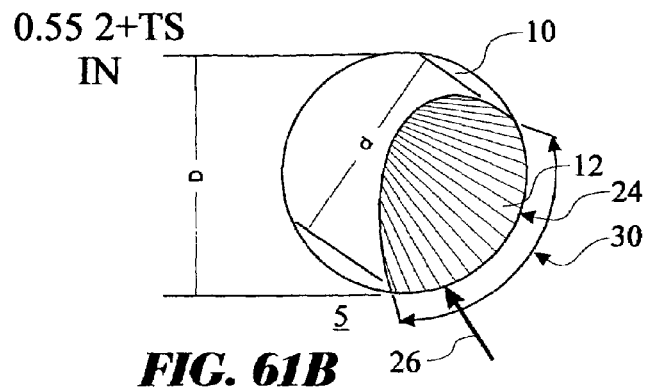
Figure 62A:
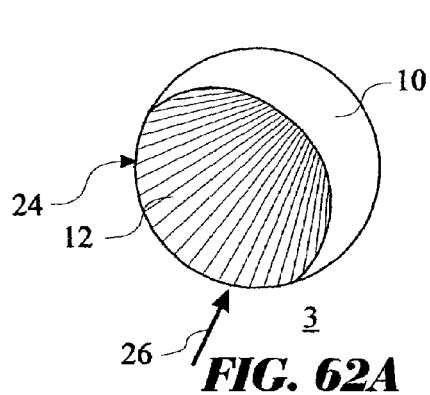
Figure 62B:
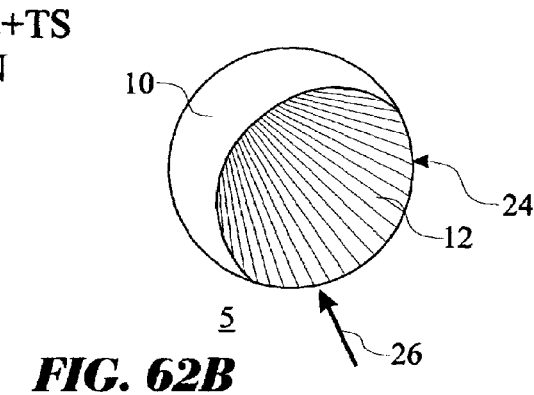
Figure 63A:
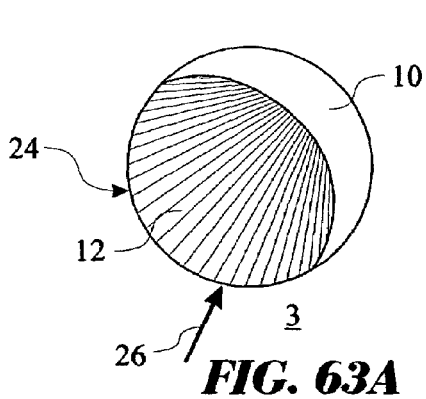
Figure 63B:
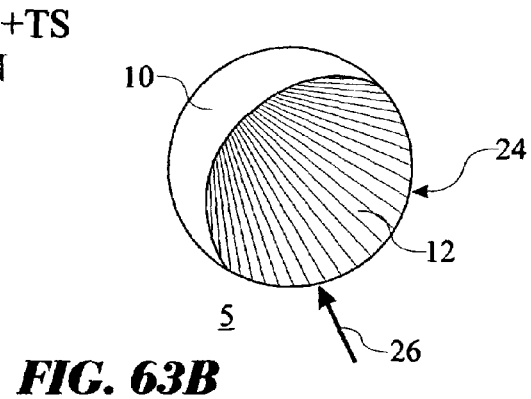
Figure 64A:
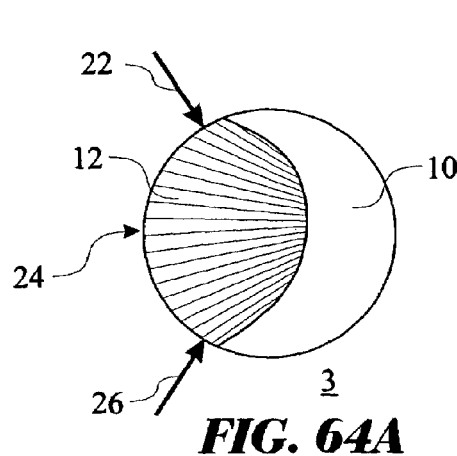
Figure 64B:
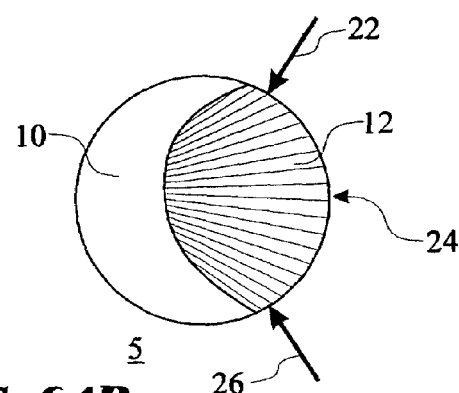
Figure 65A:
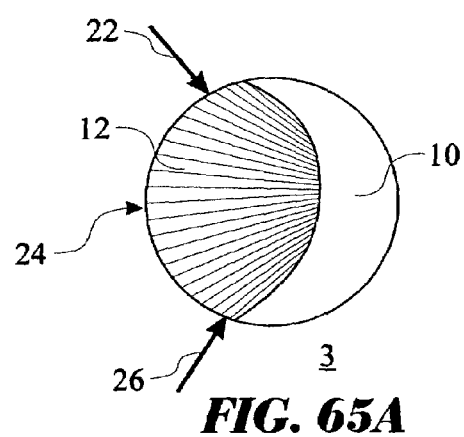
Figure 65B:
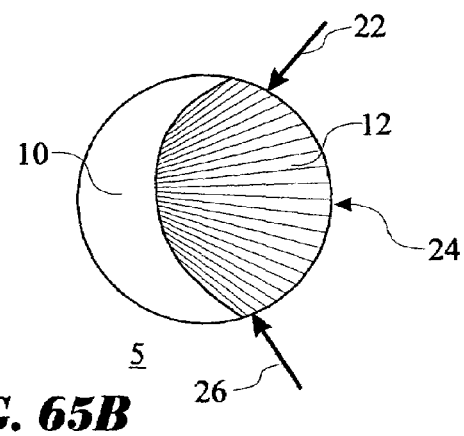
Figure 66A:
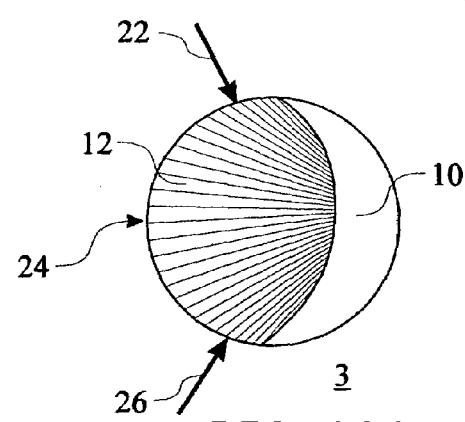
Figure 66B:
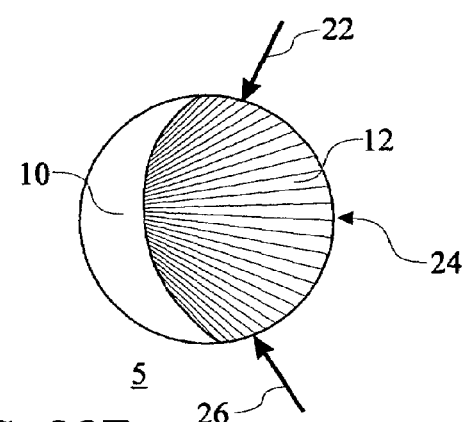
Figure 67A:
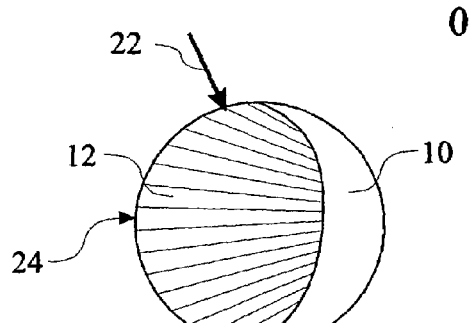
Figure 67B:
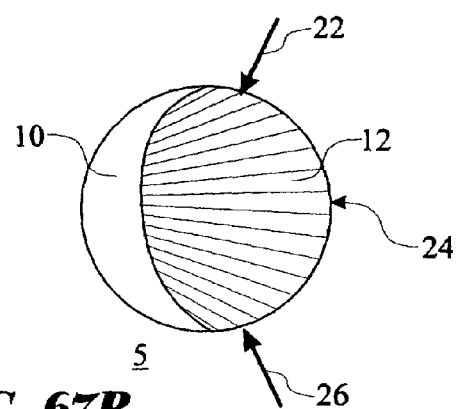
Figure 68A:
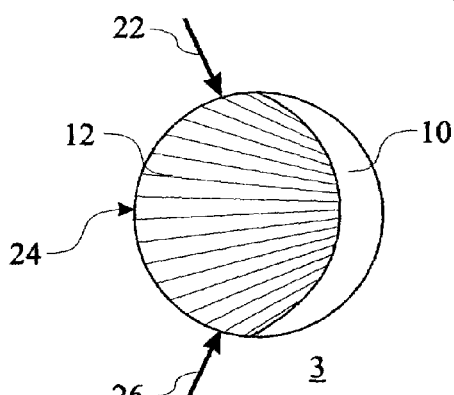
Figure 68B:
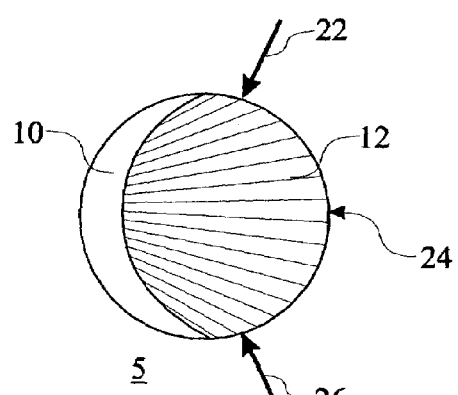
Figure 69A:
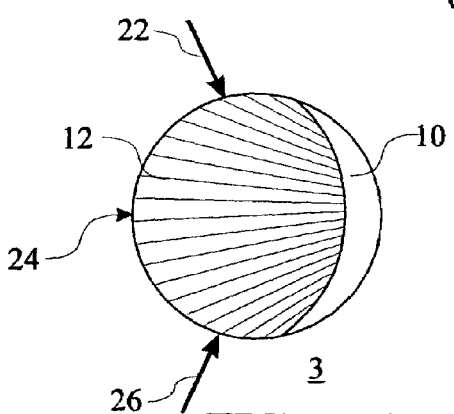
Figure 69B:
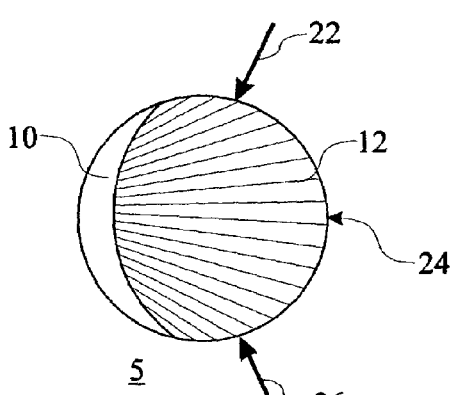
Figure 70A:
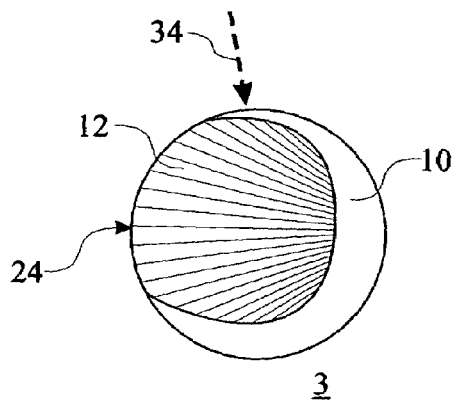
Figure 70B:
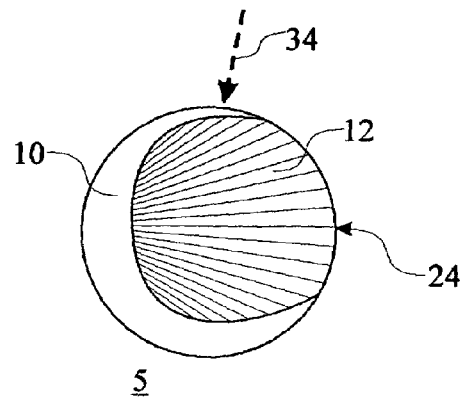
Figure 71A:
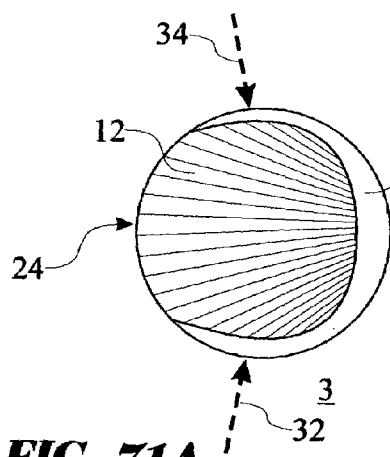
Figure 71B:
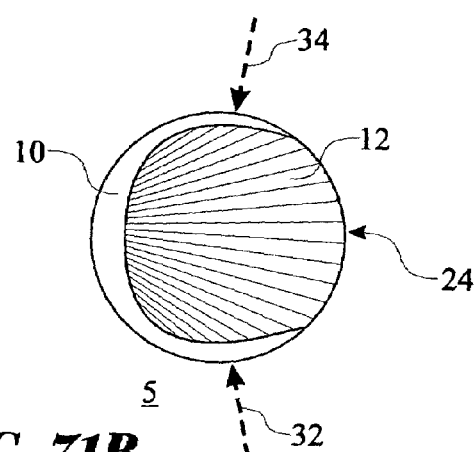
Figure 72A:
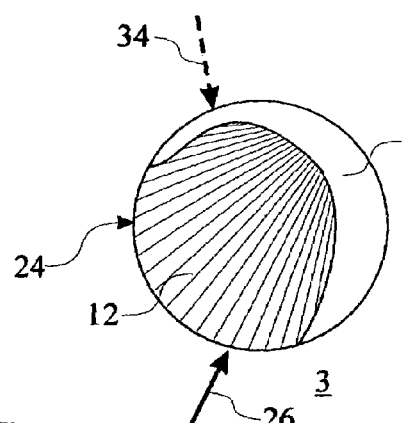
Figure 72B:
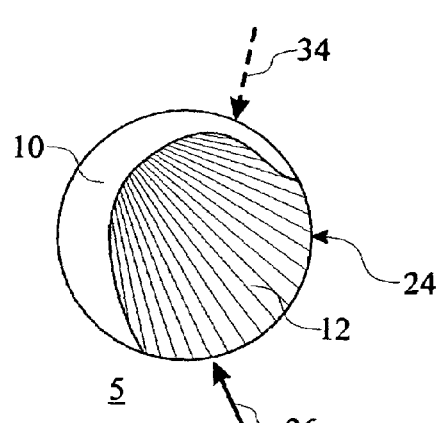
Figure 73A:
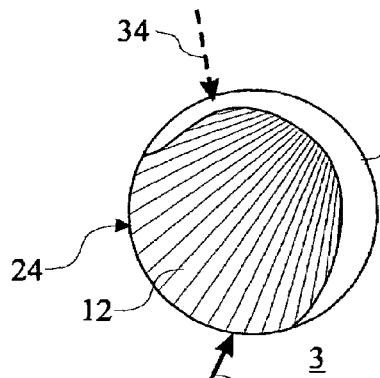
Figure 73B:
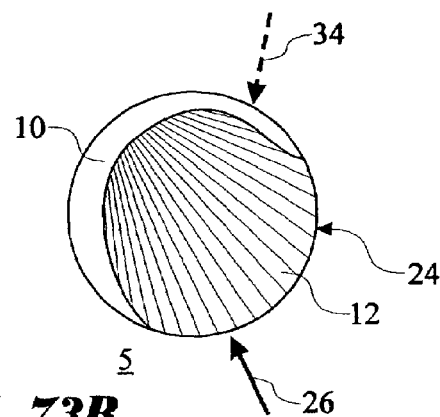
Figure 74A:
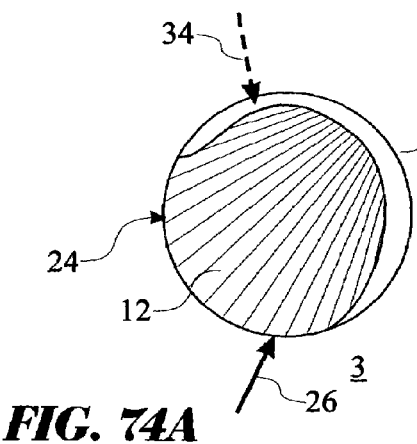
Figure 74B:
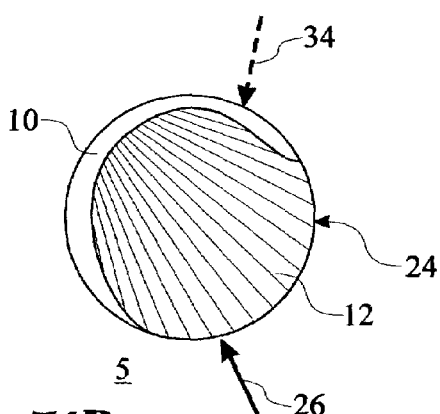
Figure 75A:
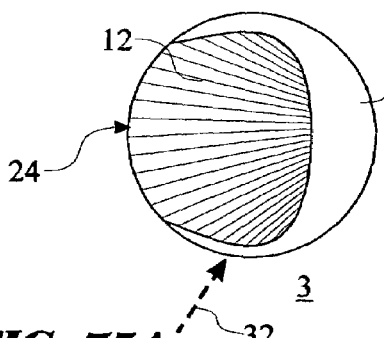
Figure 75B:
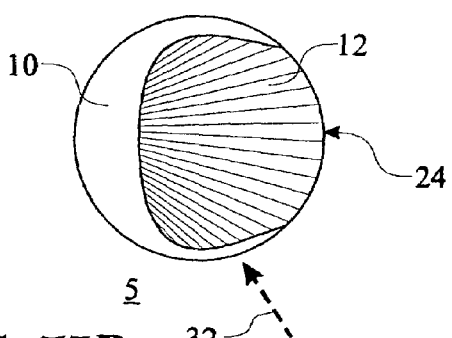
Figure 76A:
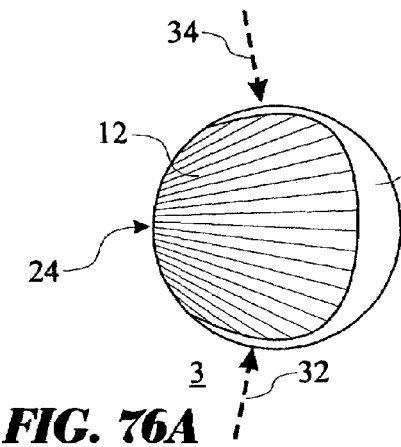
Figure 76B:
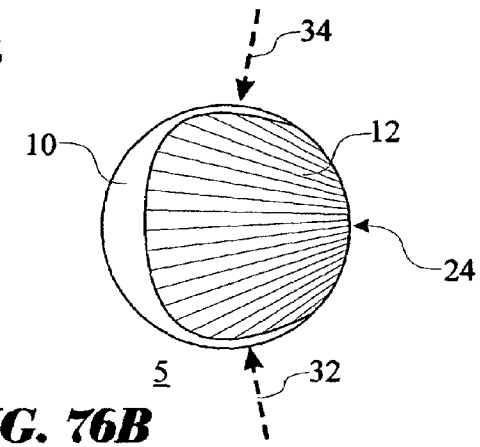
Figure 77A:
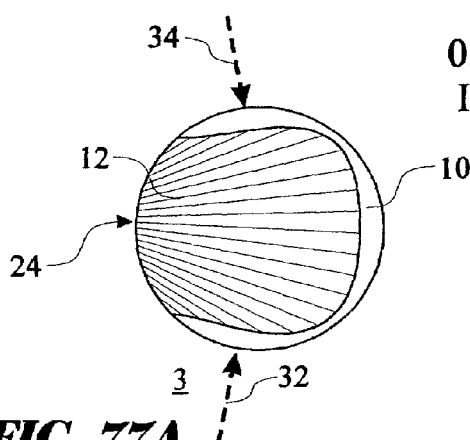
Figure 77B:
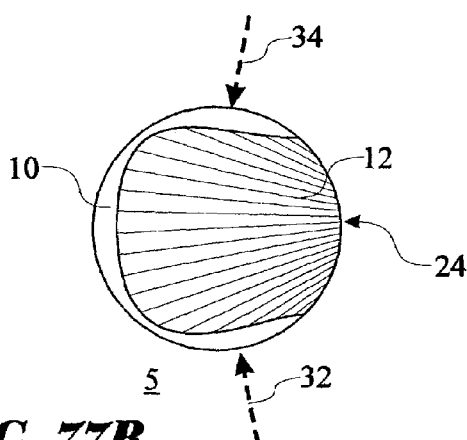
Figure 78A:
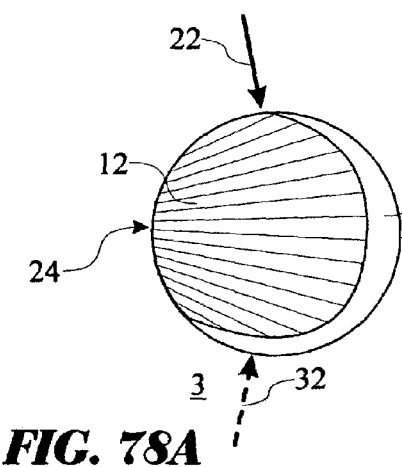
Figure 78B:
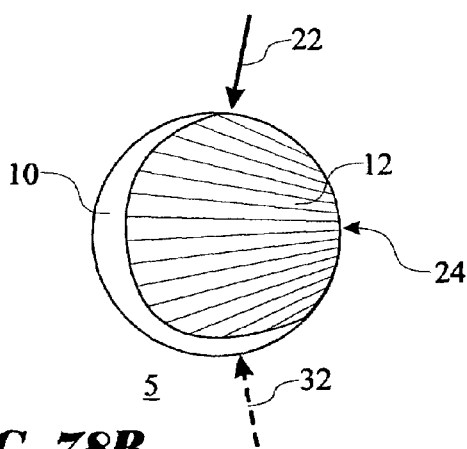
Figures 82A, 82B:
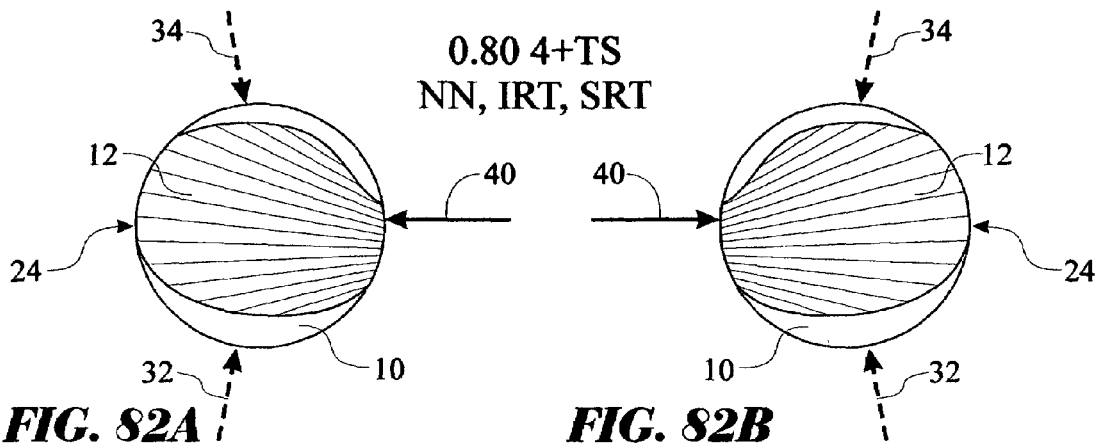
Figures 83A, 83B:
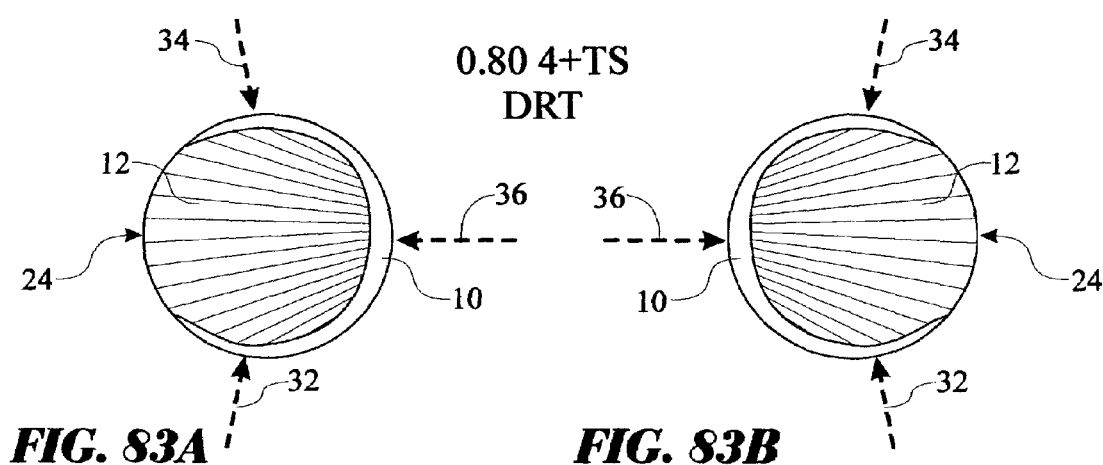
Figures 84A, 84B:
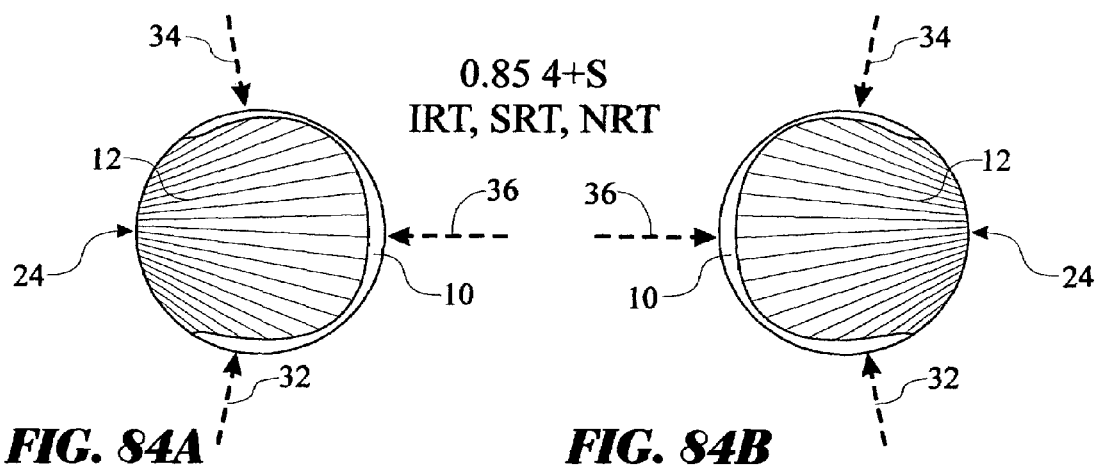
Figure 100:
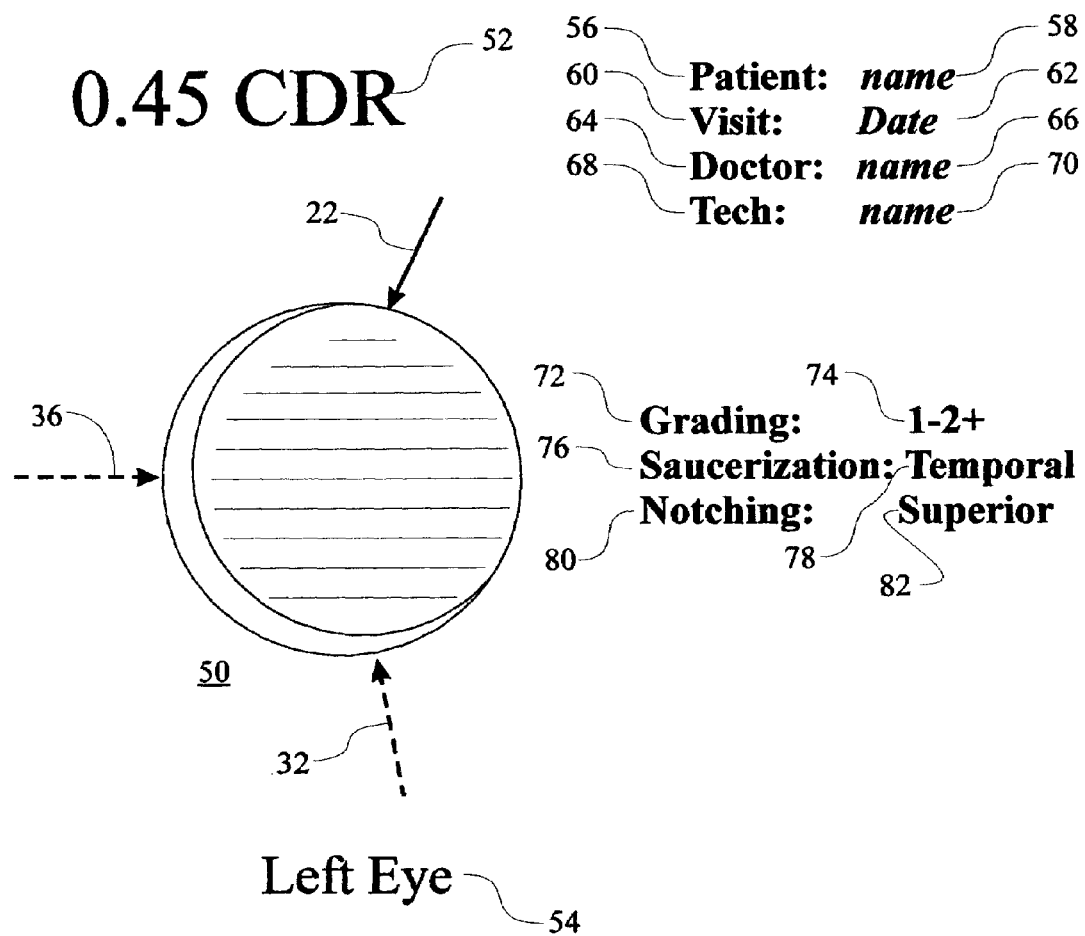
Figure 101:
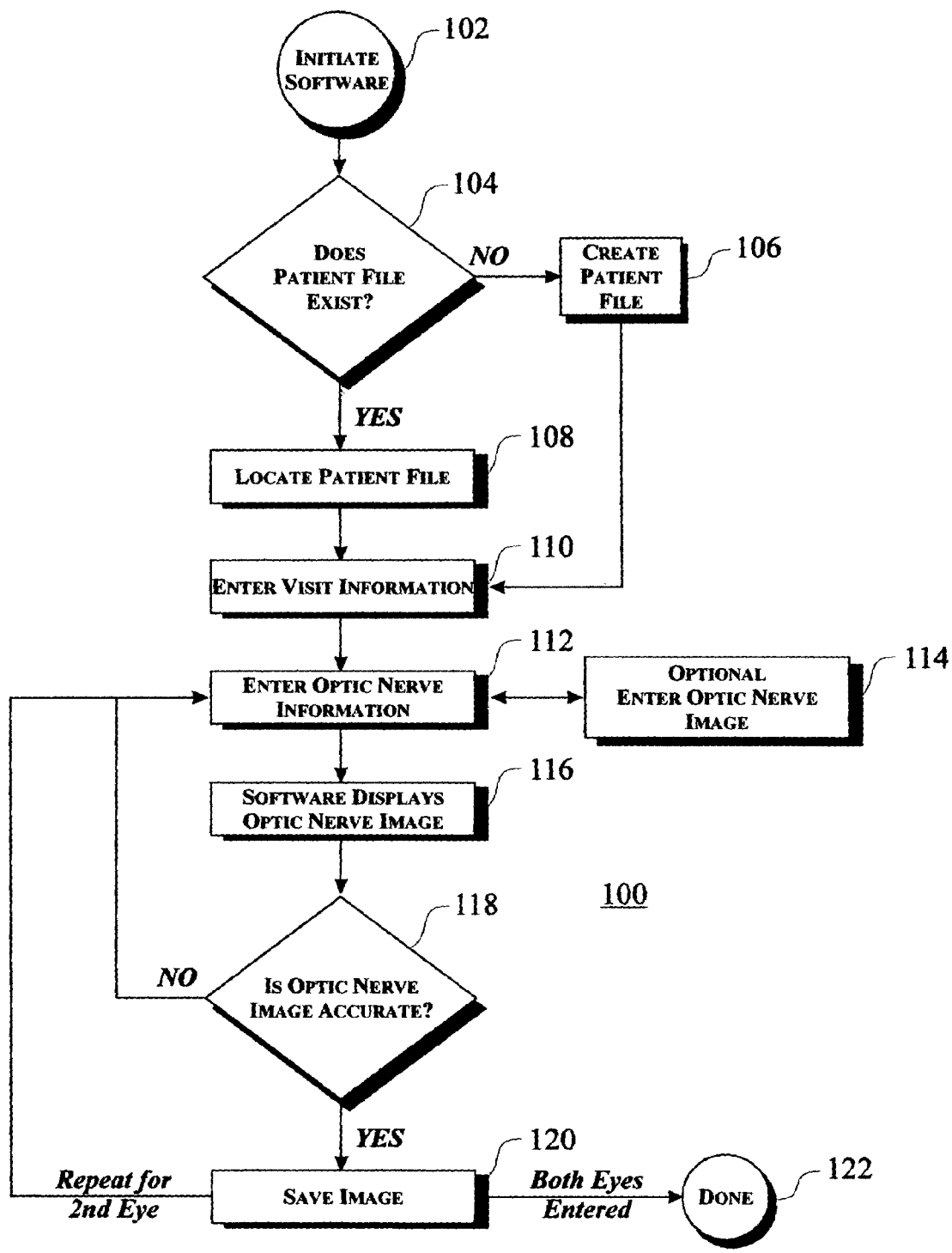
Figure 102:
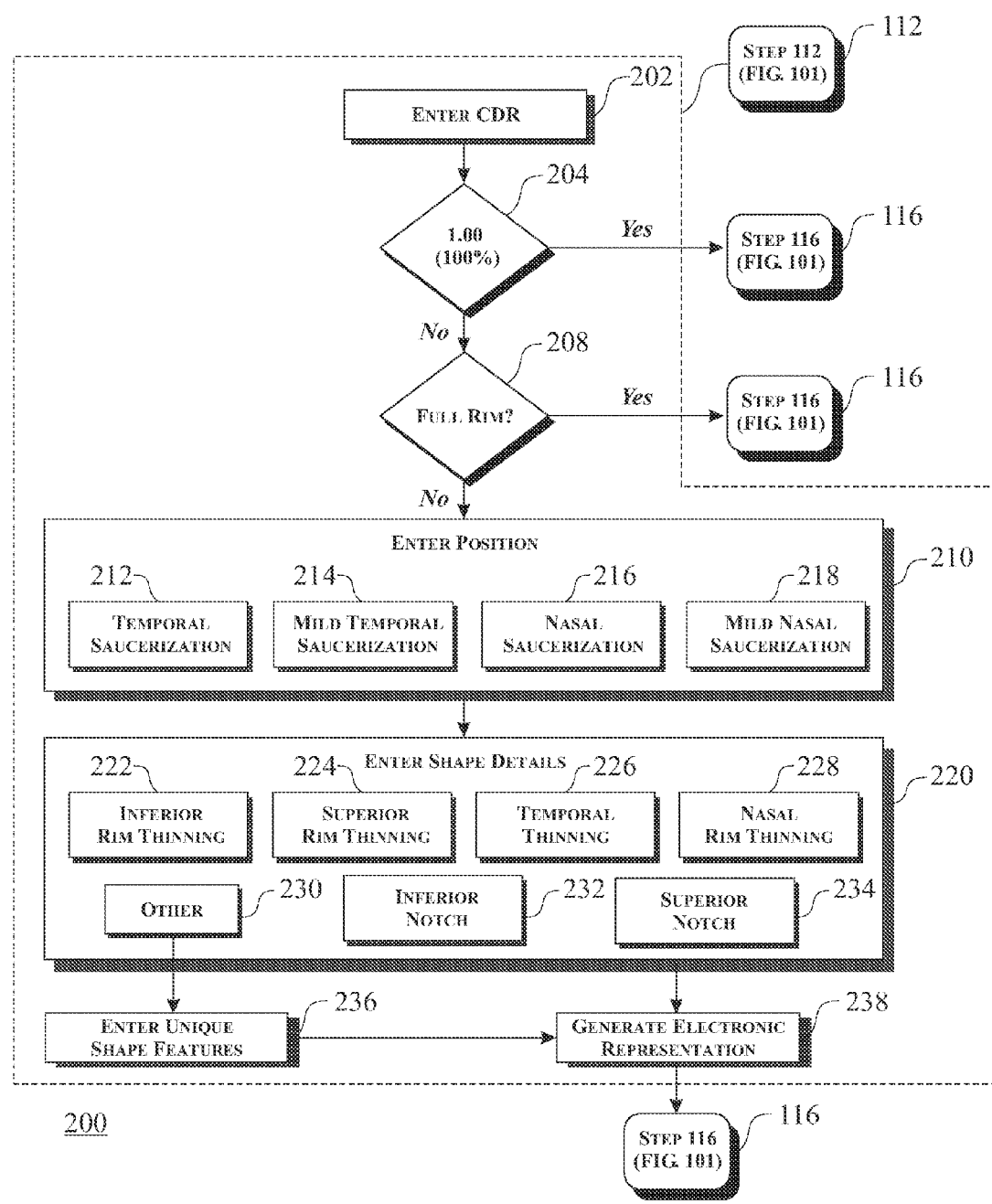
Figure 103:
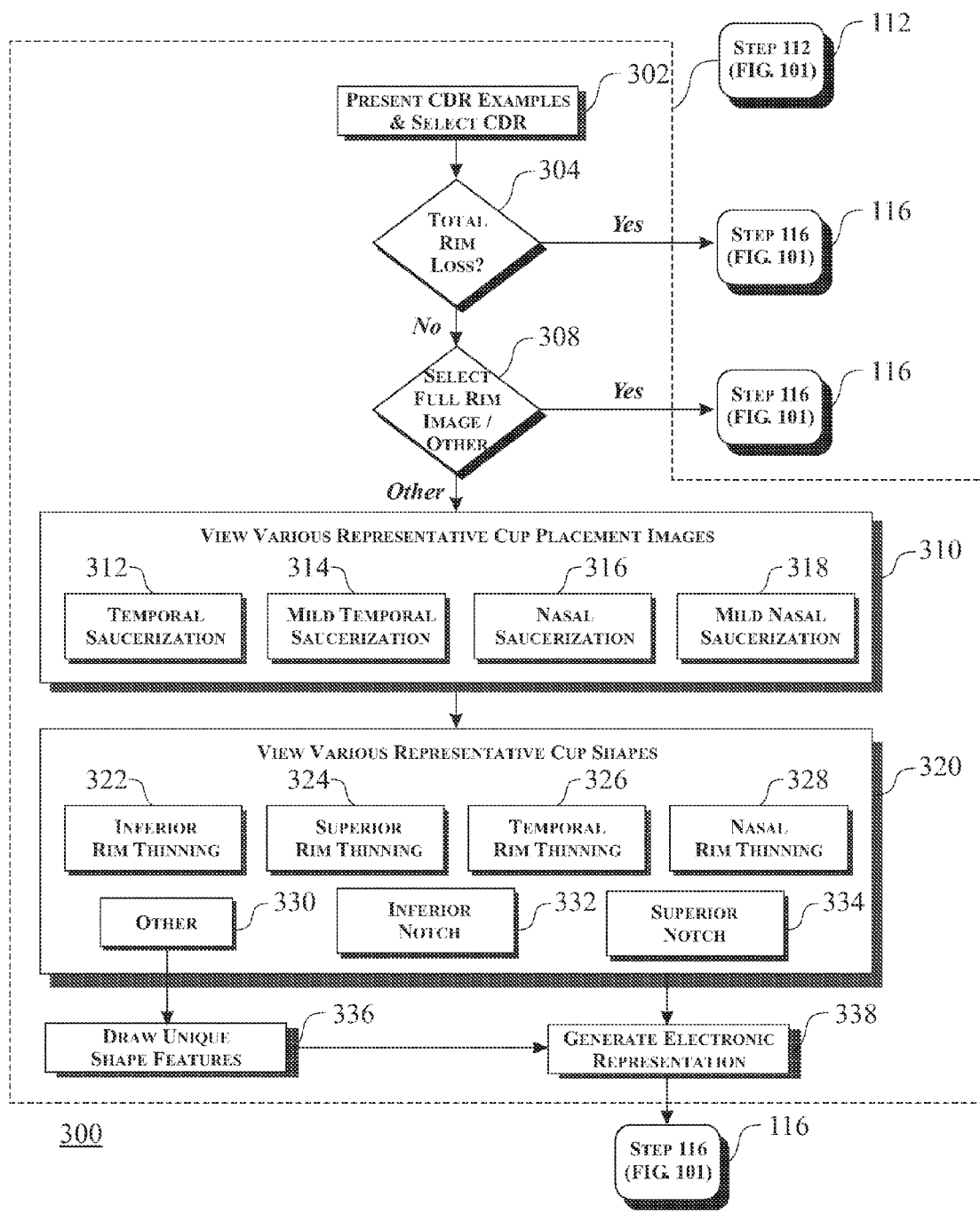
Figure 104:
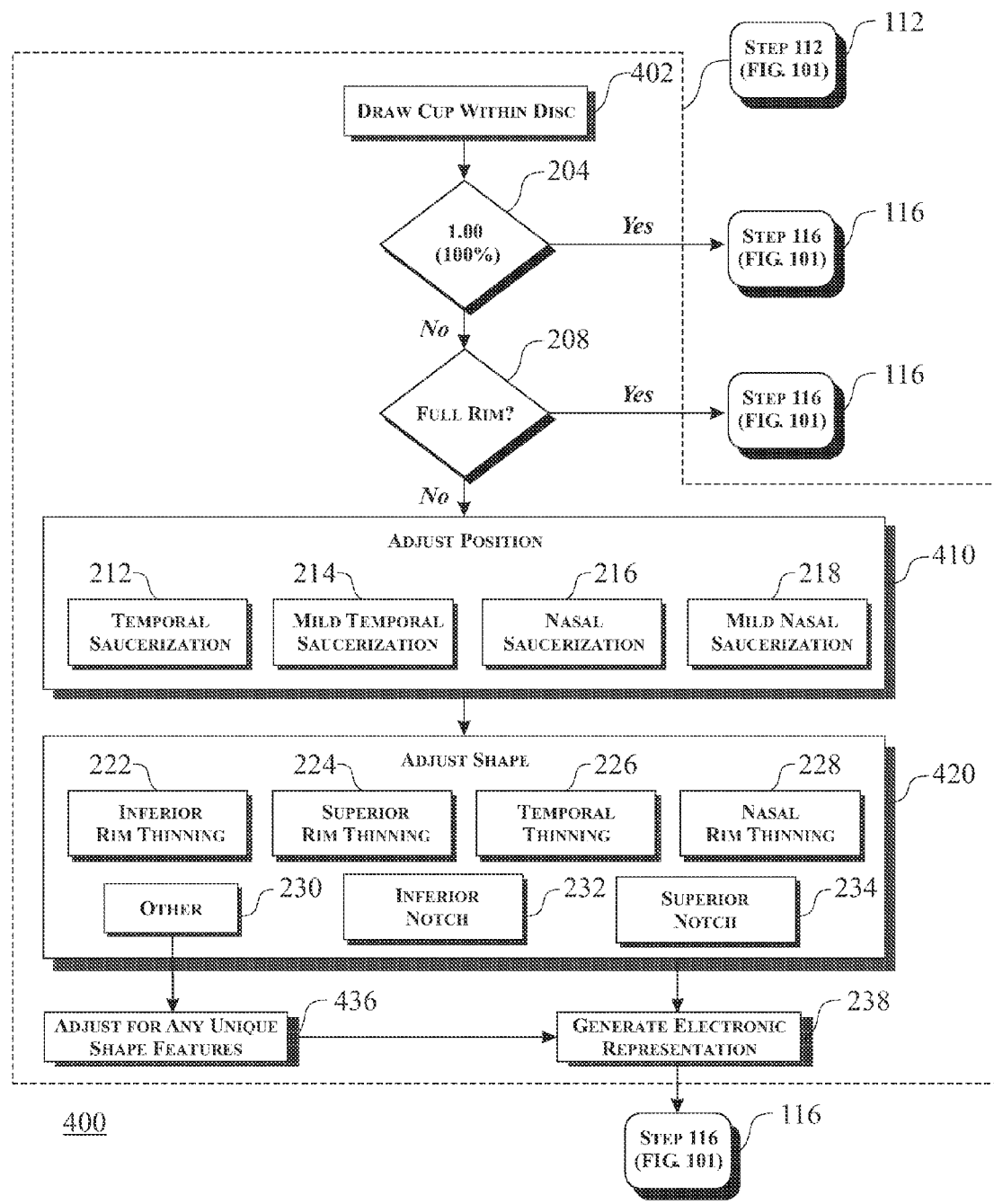

FIG. 14 is an illustration representing an optic nerve described as 0.65 cup to disc ratio (CDR) with said temporal rim thinning (TRT);

FIG. 15 is an illustration representing an optic nerve described as 0.70 cup to disc ratio (CDR) with said temporal rim thinning (TRT);

FIG. 16 is an illustration representing an optic nerve described as 0.75 cup to disc ratio (CDR) with said temporal rim thinning (TRT);

FIG. 17 is an illustration representing an optic nerve described as 0.80 cup to disc ratio (CDR) with said diffuse rim thinning (DRT);

FIG. 18 is an illustration representing an optic nerve described as 0.85 cup to disc ratio (CDR) with said diffuse rim thinning (DRT);

FIG. 19 is an illustration representing an optic nerve described as 0.90 cup to disc ratio (CDR) with said diffuse rim thinning (DRT);

FIG. 20 is an illustration representing an optic nerve described as 0.95 cup to disc ratio (CDR) with said diffuse rim thinning (DRT);

FIG. 21 is an illustration representing an optic nerve described as 0.98 cup to disc ratio (CDR) with said diffuse rim thinning (DRT);

FIG. 22 is an illustration representing an optic nerve described as 0.20 cup to disc ratio (CDR) and introducing mild temporal saucerization (MTS);

FIG. 23 is an illustration representing an optic nerve described as 0.20 cup to disc ratio (CDR) and introducing mild nasal saucerization (MNS);

FIG. 24 is an illustration representing an optic nerve described as 0.20 cup to disc ratio (CDR) and introducing inferior notching (IN);

FIG. 25 is an illustration representing an optic nerve described as 0.20 cup to disc ratio (CDR) and introducing superior notching (SN);

FIG. 26 is an illustration representing an optic nerve described as 0.25 cup to disc ratio (CDR) with said mild temporal saucerization (MTS);

FIG. 27 is an illustration representing an optic nerve described as 0.30 cup to disc ratio (CDR) and introducing temporal saucerization (TS), further introducing a method of grading saucerization, presenting a grade of 1+;

FIG. 28 is an illustration representing an optic nerve described as 0.35 cup to disc ratio (CDR) with said temporal saucerization (TS), further illustrating the grading saucerization, presenting a grade of 1+;

FIG. 29 is an illustration representing an alternate optic nerve described as 0.35 cup to disc ratio (CDR) with said temporal saucerization (TS), presenting a grade of 1+;

FIG. 30 is an illustration representing an optic nerve described as 0.40 cup to disc ratio (CDR) with temporal saucerization (TS), presenting a grade of 1+;

FIG. 31 is an illustration representing an alternate optic nerve described as 0.40 cup to disc ratio (CDR) with temporal saucerization (TS), further illustrating the grading saucerization, presenting a grade of 1+;

FIG. 32 is an illustration representing an alternate optic nerve described as 0.40 cup to disc ratio (CDR) with said superior notch (SN) and said inferior notch (IN);

FIG. 33 is an illustration representing an alternate optic nerve described as 0.40 cup to disc ratio (CDR) with said inferior notch (IN) and introducing a nasal notch (NN);

FIG. 34 is an illustration representing an optic nerve described as 0.40 cup to disc ratio (CDR) with said inferior notch (IN) and said temporal saucerization (TS), presenting a grade of 1+;

FIG. 35 is an illustration representing an optic nerve described as 0.40 cup to disc ratio (CDR) with said superior notch (SN) and said temporal saucerization (TS), presenting a grade of 1+;

FIG. 36 is an illustration representing an optic nerve described as 0.40 cup to disc ratio (CDR) with said nasal notch (NN) and said temporal saucerization (TS), presenting a grade of 1+;

FIG. 37 is an illustration representing an optic nerve described as 0.40 cup to disc ratio (CDR) with said inferior rim thinning (IRT) and said temporal saucerization (TS), presenting a grade of 1+;

FIG. 38 is an illustration representing an optic nerve described as 0.40 cup to disc ratio (CDR) introducing superior rim thinning (SRT) and said temporal saucerization (TS), presenting a grade of 1+;

FIG. 39 is an illustration representing an optic nerve described as 0.40 cup to disc ratio (CDR) introducing nasal rim thinning (NRT) and said temporal saucerization (TS), presenting a grade of 1+;

FIG. 40 is an illustration representing an optic nerve described as 0.45 cup to disc ratio (CDR) said temporal saucerization (TS), and Superior Notch (SN), presenting a grade of 2+;

FIG. 41 is an illustration representing an optic nerve described as 0.45 cup to disc ratio (CDR) with temporal saucerization (TS), further illustrating the grading saucerization, presenting a grade of 2+;

FIG. 42 is an illustration representing an optic nerve described as 0.50 cup to disc ratio (CDR) with temporal saucerization (TS) comprising said saucerization grade of 2+;

FIG. 43 is an illustration representing an optic nerve described as 0.55 cup to disc ratio (CDR) with temporal saucerization (TS) comprising said saucerization grade of 2+;

FIG. 44 is an illustration representing an optic nerve described as 0.60 cup to disc ratio (CDR) with temporal saucerization (TS) comprising said saucerization grade of 2+;

FIG. 45 is an illustration representing an optic nerve described as 0.30 cup to disc ratio (CDR) and said superior notch (SN);

FIG. 46 is an illustration representing an optic nerve described as 0.35 up to disc ratio (CDR) and said superior notch (SN);

FIG. 47 is an illustration representing an optic nerve described as 0.45 cup to disc ratio (CDR), said superior notch (SN), and said temporal saucerization (TS), comprising said saucerization grade of 2+;

FIG. 48 is an illustration representing an optic nerve described as 0.65 cup to disc ratio (CDR) with temporal saucerization (TS), and superior notch (SN), further comprising said saucerization grade of 3+;

FIG. 49 is an illustration representing an optic nerve described as 0.70 cup to disc ratio (CDR) with temporal saucerization (TS) and said superior notch (SN), further comprising said saucerization grade of 3+;

FIG. 50 is an illustration representing an optic nerve described as 0.80 cup to disc ratio (CDR) with temporal saucerization (TS) and said superior notch (SN), further comprising said saucerization grade of 4+;

FIG. 51 is an illustration representing an optic nerve described as 0.30 cup to disc ratio (CDR) with said inferior notch (IN);

FIG. 52 is an illustration representing an optic nerve described as 0.35 cup to disc ratio (CDR) with said inferior notch (IN);

FIG. 53 is an illustration representing an optic nerve described as 0.40 cup to disc ratio (CDR) with said inferior notch (IN);

FIG. 54 is an illustration representing an alternate optic nerve described as 0.40 cup to disc ratio (CDR) with said inferior notch (IN);

FIG. 55 is an illustration representing an optic nerve described as 0.50 cup to disc ratio (CDR) with said inferior notch (IN), further comprising said saucerization grade of 4+;

FIG. 56 is an illustration representing an optic nerve described as 0.30 cup to disc ratio (CDR) with temporal saucerization (TS) and said inferior notch (IN), further illustrating the grading saucerization, presenting a grade of 1+;

FIG. 57 is an illustration representing an optic nerve described as 0.40 cup to disc ratio (CDR) with temporal saucerization (TS) and said inferior notch (IN), further illustrating the grading saucerization, presenting a grade of 1+;

FIG. 58 is an illustration representing an optic nerve described as 0.40 cup to disc ratio (CDR) with temporal saucerization (TS) and said inferior notch (IN), further illustrating the grading saucerization, presenting a grade of 2+;

FIG. 59 is an illustration representing an optic nerve described as 0.45 cup to disc ratio (CDR) with temporal saucerization (TS) and said inferior notch (IN), further illustrating the grading saucerization, presenting a grade of 2+;

FIG. 60 is an illustration representing an optic nerve described as 0.50 cup to disc ratio (CDR) with temporal saucerization (TS) and said inferior notch (IN), further illustrating the grading saucerization, presenting a grade of 2+;

FIG. 61 is an illustration representing an optic nerve described as 0.55 cup to disc ratio (CDR) with temporal saucerization (TS) and said inferior notch (IN), further illustrating the grading saucerization, presenting a grade of 2+;

FIG. 62 is an illustration representing an optic nerve described as 0.60 cup to disc ratio (CDR) with temporal saucerization (TS) and said inferior notch (IN), further comprising said saucerization grade of 2+;

FIG. 63 is an illustration representing an optic nerve described as 0.65 cup to disc ratio (CDR) with temporal saucerization (TS) and said inferior notch (IN), further comprising said saucerization grade of 2+;

FIG. 64 is an illustration representing an optic nerve described as 0.55 cup to disc ratio (CDR) with temporal saucerization (TS), inferior notch (IN), and superior notch (SN), further comprising said saucerization grade of 2+;

FIG. 65 is an illustration representing an optic nerve described as 0.60 cup to disc ratio (CDR) with temporal saucerization (TS), said inferior notch (IN), and said superior notch (SN), further comprising said saucerization grade of 2+;

FIG. 66 is an illustration representing an optic nerve described as 0.65 cup to disc ratio (CDR) with temporal saucerization (TS), said inferior notch (IN), and said superior notch (SN), further comprising said saucerization grade of 2+;

FIG. 67 is an illustration representing an optic nerve described as 0.70 cup to disc ratio (CDR) with temporal saucerization (TS), said inferior notch (IN), and said superior notch (SN), further comprising said saucerization grade of 3+;

FIG. 68 is an illustration representing an optic nerve described as 0.75 cup to disc ratio (CDR) with temporal saucerization (TS), said inferior notch (IN), and said superior notch (SN), further comprising said saucerization grade of 3+;

FIG. 69 is an illustration representing an optic nerve described as 0.80 cup to disc ratio (CDR) with temporal saucerization (TS), said inferior notch (IN), and said superior notch (SN), further comprising said saucerization grade of 4+;

FIG. 70 is an illustration representing an optic nerve described as 0.65 cup to disc ratio (CDR) with temporal saucerization (TS) and said superior rim thinning (SRT), further comprising said saucerization grade of 2-3+;

FIG. 71 is an illustration representing an optic nerve described as 0.70 cup to disc ratio (CDR) with temporal saucerization (TS), said superior rim thinning (SRT), said inferior rim thinning (IRT), further comprising said saucerization grade of 3+;

FIG. 72 is an illustration representing an optic nerve described as 0.70 cup to disc ratio (CDR) with temporal saucerization (TS), said inferior notch (IN), and said superior rim thinning (SRT), further comprising said saucerization grade of 3+;

FIG. 73 is an illustration representing an optic nerve described as 0.75 cup to disc ratio (CDR) with temporal saucerization (TS), said inferior notch (IN), and said superior rim thinning (SRT), further comprising said saucerization grade of 3+;

FIG. 74 is an illustration representing an optic nerve described as 0.80 cup to disc ratio (CDR) with temporal saucerization (TS), said inferior notch (IN), and said superior rim thinning (SRT), further comprising said saucerization grade of 3+;

FIG. 75 is an illustration representing an optic nerve described as 0.65 cup to disc ratio (CDR) with temporal saucerization (TS) and said inferior rim thinning (IRT), further comprising said saucerization grade of 2-3+;

FIG. 76 is an illustration representing an optic nerve described as 0.75 cup to disc ratio (CDR) with temporal saucerization (TS), said inferior rim thinning (IRT), and said superior rim thinning (SRT), further comprising said saucerization grade of 3+;

FIG. 77 is an illustration representing an optic nerve described as 0.80 cup to disc ratio (CDR) with temporal saucerization (TS), said inferior rim thinning (IRT), and said superior rim thinning (SRT), further comprising said saucerization grade of 4+;

FIG. 78 is an illustration representing an optic nerve described as 0.80 cup to disc ratio (CDR) with temporal saucerization (TS), said superior notch (SN), and said inferior rim thinning (IRT), further comprising said saucerization grade of 4+;

FIG. 79 is an illustration representing an optic nerve described as 0.80 cup to disc ratio (CDR) with temporal saucerization (TS), said inferior notch (IN), and said superior notch (SN), further comprising said saucerization grade of 4+;

FIG. 80 is an illustration representing an optic nerve described as 0.80 cup to disc ratio (CDR) with temporal saucerization (TS), said inferior notch (IN), said nasal notch (NN), and said superior rim thinning (SRT), further comprising said saucerization grade of 4+;

FIG. 81 is an illustration representing an optic nerve described as 0.80 cup to disc ratio (CDR) with temporal saucerization (TS), said superior notch (SN), and said nasal notch (NN), further comprising said saucerization grade of 4+;

FIG. 82 is an illustration representing an optic nerve described as 0.80 cup to disc ratio (CDR) with temporal saucerization (TS), said nasal notch (NN), said inferior rim thinning (IRT), and said superior rim thinning (SRT), further comprising said saucerization grade of 4+;

FIG. 83 is an illustration representing an optic nerve described as 0.80 cup to disc ratio (CDR) with temporal saucerization (TS), and said diffuse rim thinning DRT), further comprising said saucerization grade of 4+;

FIG. 84 is an illustration representing an optic nerve described as 0.85 cup to disc ratio (CDR) with temporal saucerization (TS), said inferior rim thinning (IRT), said superior rim thinning (SRT), and said nasal rim thinning (NRT), further comprising said saucerization grade of 4+;

FIG. 85 is an illustration representing an optic nerve described as 0.85 cup to disc ratio (CDR) with temporal saucerization (TS), said superior notch (SN), inferior rim thinning (IRT), and said nasal rim thinning (NRT), further comprising said saucerization grade of 4+;

FIG. 86 is an illustration representing an optic nerve described as 0.85 cup to disc ratio (CDR) with temporal saucerization (TS), said inferior notch (IN), said superior notch (SN), and said nasal rim thinning (NRT), further comprising said saucerization grade of 4+;

FIG. 87 is an illustration representing an optic nerve described as 0.85 cup to disc ratio (CDR) with temporal saucerization (TS), said inferior notch (IN), said superior rim thinning (SRT), and nasal rim thinning (NRT), further comprising said saucerization grade of 4+;

FIG. 88 is an illustration representing an optic nerve described as 0.90 cup to disc ratio (CDR) with temporal saucerization (TS), said inferior notch (IN), said superior notch (SN), and said nasal rim thinning (NRT), further comprising said saucerization grade of 4+;

FIG. 89 is an illustration representing an optic nerve described as 0.90 cup to disc ratio (CDR) with temporal saucerization (TS), said inferior rim thinning (IRT), said superior rim thinning (SRT), and said nasal rim thinning (NRT), further comprising said saucerization grade of 4+;

FIG. 90 is an illustration representing an optic nerve described as 0.95 cup to disc ratio (CDR) with temporal saucerization (TS), said inferior notch (IN), said superior notch (SN), and said nasal rim thinning (NRT), further comprising said saucerization grade of 4+;

FIG. 91 is an illustration representing an optic nerve described as 0.95 cup to disc ratio (CDR) with temporal saucerization (TS), said inferior notch (IN), said superior rim thinning (SRT), and said nasal rim thinning (NRT), further comprising said saucerization grade of 4+;

FIG. 92 is an illustration representing an optic nerve described as 0.95 cup to disc ratio (CDR) with temporal saucerization (TS), said inferior notch (IN), nasal notch (NN), and said superior rim thinning (SRT), further comprising said saucerization grade of 4+;

FIG. 93 is an illustration representing an optic nerve described as 0.95 cup to disc ratio (CDR) with temporal saucerization (TS), said inferior notch (IN), said nasal notch (NN), said superior rim thinning (SRT), and, further comprising said saucerization grade of 4+;

FIG. 94 is an illustration representing an optic nerve described as 0.98 cup to disc ratio (CDR) with temporal saucerization (TS), said superior notch (SN), said nasal notch (NN), and said inferior rim thinning (IRT), further comprising said saucerization grade of 4+;

FIG. 95 is an illustration representing an optic nerve described as 0.98 cup to disc ratio (CDR) with temporal saucerization (TS), said inferior notch (IN), said superior notch (SN), and said nasal rim thinning (NRT), further comprising said saucerization grade of 4+;

FIG. 96 is an illustration representing an optic nerve described as 0.40 cup to disc ratio (CDR) with said nasal notch (NN), further comprising said saucerization grade of 2+;

FIG. 97 is an illustration representing an optic nerve described as 0.50 cup to disc ratio (CDR) with said nasal notch (NN), further comprising said temporal saucerization grade of 2+;

FIG. 98 is an illustration representing an optic nerve described as 0.60 cup to disc ratio (CDR) with said nasal notch (NN), further comprising said temporal saucerization grade of 2+;

FIG. 99 is an illustration representing an optic nerve described as 0.70 cup to disc ratio (CDR) with said nasal notch (NN), further comprising said saucerization grade of 2+;

FIG. 100 is an illustration representing a graphical representation and respective features of how the software would present said image in accordance with the present invention;

FIG. 101 is a flow diagram representing the overall method respective to the present invention;

FIG. 102 is a flow diagram representing details of a first method for obtaining an illustrative representation of a patient's optic nerve;

FIG. 103 is a flow diagram representing details of a second method for obtaining an illustrative representation of a patient's optic nerve; and FIG. 104 is a flow diagram representing details of a third method for obtaining an illustrative representation of a patient's optic nerve Like reference numerals refer to like parts throughout the various illustrations.

DETAILED DESCRIPTION OF THE PREFERRED EMBODIMENTS

Shown throughout the figures/the present invention is directed towards an electronic medical record method, more specifically, one that generates and stores illustrations representative of a patient's optic nerve. To simplify a potentially complex and repetitive disclosure, like elements are described in detail upon the first introduction and further presented where appropriate. The disclosed terminology is commonly known in the industry and by those skilled in the art. The features presented are respective to which eye is being diagnosed.

Figure 1:
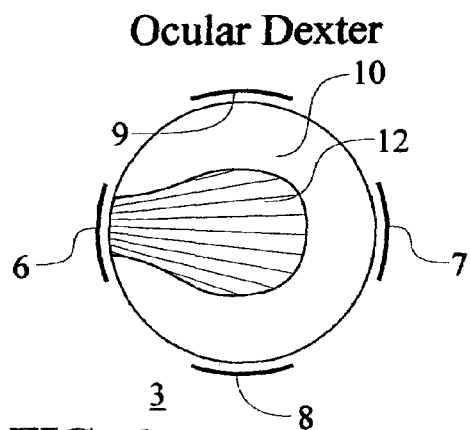
FIG. 1 is an illustration representing an optic nerve introducing Ocular Dexter (OD) (Right eye)

FIG. 1 is an illustration representing a right optic nerve representation 3 introducing Ocular Dexter (OD) (Right eye). Said left optic nerve representation 5 introduces an optic nerve disc 10 and a respective optic nerve cup 12. Said optic nerve cup 12 is illustrated as a shaded area throughout the figures and specification. The present invention focuses on the shape, size, and positioning of said optic nerve cup 12 within said optic nerve disc 10. The orientation of the eye is referenced in accordance with the respective eye. There are four (4) referenced sections used for describing features of the optic nerve:

a. Temporal 6: Oriented horizontally, towards the patient's ear
b. Nasal 7: Oriented horizontally, towards the patients nose
c. Inferior 8: Oriented vertically, towards the patient's chin
Superior 9: Oriented vertically, towards the patient's eyebrow.

Figure 2:
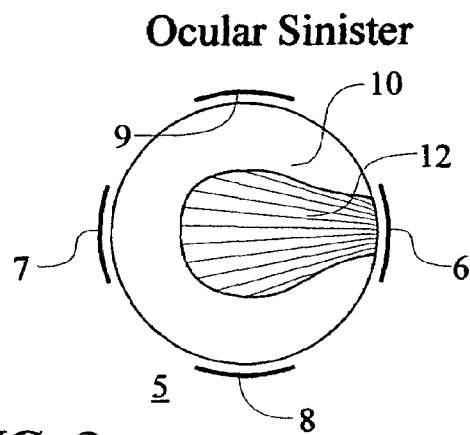
FIG. 2 is an illustration representing an optic nerve introducing Ocular Sinister (OS) (Left eye)

FIG. 2 is an illustration representing a left optic nerve representation 5 introducing Ocular Sinister (OS) (left eye). The illustration presents the difference in the location of each of the four (4) referenced sections between said Ocular Sinister (OS) (left eye) 5 and Ocular Dexter (OD) (right eye) 3. The primary difference places the temporal 6 and nasal 7 on opposing sides. The chart should be recorded as shown wherein the patient's Ocular Sinister (OS) (left eye) 5 is illustrated on the right, and the patients Ocular Dexter (OD) (right eye) 3 is illustrated on the left; as if one were looking directly at the patient. In the figures below, illustration A is representative of said Ocular Dexter (OD) (right eye) 3 and illustration B is representative if said Ocular Sinister (OS) (left eye) 5. Although the drawings illustrate both said Ocular Dexter (OD) (right eye) 3 and said Ocular Sinister (OS) (left eye) 5 being equal, it is more common that each one is diagnosed and recorded individually.

FIG. 3 illustrates a representation of a patient's optic nerve. FIG. 3 is an illustration representing an optic nerve introducing a condition of total rim loss (TRL). A primary feature when describing a patient's optic nerve is the ratio between the area of said optic nerve cup 12 and the area of said optic nerve disc 10. This ratio of areas is referred to as a "cup to disc ratio" or CDR. Said CDR is recorded in decimal format. Said CDR can vary between 0.10 and 1.00; wherein 1.00 is better referred to as total rim loss (TRL) as illustrated herein. Said area of said optic nerve disc 10 is determined using the respective diameter "D" and determining said area of said optic nerve cup 12 represented in the illustration by dimension "d", or as the shaded area. The resulting CDR is then said area of said optic nerve cup 12 divided by said area of said optic nerve disc 10. Different CDR's will be presented throughout the detailed descriptions of the drawings. Although the diameter "D" and dimension "d" are removed from a portion of the figures for clarity, they should be understood throughout all drawings.

FIGS. 4 through 21 illustrate a second representation of a patient's optic nerve. The illustrations present optic nerves comprising various CDR's. The illustrations further illustrate said optic nerve cup 12 introducing a placement referred to as a full rim 16. Said full rim 16 is a condition where said optic nerve cup 12 is positioned such that said optic nerve cup 12 is contained entirely within a perimeter of said optic nerve disc 10. Said optic nerve cup 12 can be presented either centered or off-center when referenced to the center of said optic nerve disc 10. The present invention can further comprise a step allowing the user to direct for an offset from center. One skilled in the art can provide respective steps for accommodating such an offset. It is recognized that conditions represented as said full rim 16 are the least complicated for creating an electronic representation, thus requiring less steps, as will be presented later herein.

A full rim condition is commonly understood with a CDR between 0.10 and 0.55. A CDR of between 0.55 and 0.80, said optic nerve cup 12 would encroach towards at least one quadrant edge of said optic nerve disc 10. FIGS. 12-16 introduce a condition referred to as temporal rim thinning (TRT). Said optic nerve cup 12 can be offset in varying positions respective to said optic nerve disc 10, thus presenting conditions referred to as "x" rim thinning, wherein "x" will be taught later herein. Said temporal rim thinning (TRT) has been described in the background section above. A CDR above 0.80 is generally referred to as diffuse rim thinning (DRT), as illustrated by FIGS. 17-21. Said diffuse rim thinning (DRT) has been described in the background section above.

FIGS. 4 through 21 illustrate additional full rim (FR) 16 conditions, each with a different CDR or orientation. The various figures illustrating a full rim (FR) 16 condition or similar are defined in Table 1.

TABLE 1

Figures illustrating a Full Rim or similar condition

| FIGURE | Cup to Disc Ratio | Full Rim | Temporal Rim Thinning | Diffuse Rim Thinning | Total Rim Loss |
|---|---|---|---|---|---|
| 4 | 0.10 | FR | | | |
| 5 | 0.20 | FR | | | |
| 6 | 0.25 | FR | | | |
| 7 | 0.30 | FR | | | |
| 8 | 0.35 | FR | | | |
| 9 | 0.40 | FR | | | |
| 10 | 0.45 | FR | | | |
| 11 | 0.50 | FR | | | |
| 12 | 0.55 | | TRT | | |
| 13 | 0.60 | | TRT | | |
| 14 | 0.65 | | TRT | | |
| 15 | 0.70 | | TRT | | |
| 16 | 0.75 | | TRT | | |
| 17 | 0.80 | | | DRT | |
| 18 | 0.85 | | | DRT | |
| 19 | 0.90 | | | DRT | |
| 20 | 0.95 | | | DRT | |
| 21 | 0.98 | | | DRT | |
| 3 | 1.00 | | | | TRL |

FIGS. 22 and 26 illustrate yet another representation of a patient's optic nerve. The illustrations present optic nerves comprising various CDR's and introducing a mild temporal saucerization (MTS) 28 condition. Mild temporal saucerization (MTS) 28 is defined as saucerization that is very minor sloping excavation of the outer or temporal (towards the ear) side of the optic nerve.

FIG. 23 illustrates yet another representation of a patient's optic nerve. The illustrations present optic nerves comprising a representative CDR and introducing a mild nasal saucerization (MNS) 29 condition. Mild nasal saucerization (MNS) 29 is defined as saucerization that is very minor sloping excavation of the inner or nasal (towards the nose) side of the optic nerve.

The following table presents examples of said mild temporal saucerization 28 and mild nasal saucerization (MNS) 29 conditions:

TABLE 2

Figures illustrating Optic Nerves exhibiting mild saucerization

| FIGURE | Cup to Disc Ratio | Mild Temporal Saucerization | Mild Nasal Saucerization |
|---|---|---|---|
| 22 | 0.20 | MTS | |
| 23 | 0.10 | | MNS |
| 26 | 0.25 | MTS | |

FIG. 24 illustrates yet another representation of a patient's optic nerve. The figure introduces a condition referred to as inferior notch (IN) 26. Notching is indicated by a solid lined arrow. Said inferior notch (IN) 26 is characterized wherein said optic nerve cup 12 contacts said optic nerve disc 10 along said inferior 8 section (shown in FIGS. 1 and 2) of said optic nerve disc 10.

The following table presents examples of said inferior notch (IN) 26:

TABLE 3

Figures illustrating examples of Inferior Notch

| FIG. | CDR | IN | TS | SN | NN | SRT | NRT |
|---|---|---|---|---|---|---|---|
| 24 | 0.20 | IN | | | | | |
| 32 | 0.40 | IN | | SN | | | |
| 33 | 0.40 | IN | | | NN | | |
| 34 | 0.40 | IN | 1 + TS | | | | |
| 51 | 0.30 | IN | | | | | |
| 52 | 0.35 | IN | | | | | |
| 53 & 54 | 0.40 | IN | | | | | |
| 55 | 0.50 | IN | 1 + TS | | | | |
| 56 | 0.30 | IN | 1 + TS | | | | |
| 57 | 0.40 | IN | 1 + TS | | | | |
| 58 | 0.40 | IN | 2 + TS | | | | |
| 59 | 0.45 | IN | 2 + TS | | | | |
| 60 | 0.50 | IN | 2 + TS | | | | |
| 61 | 0.55 | IN | 2 + TS | | | | |
| 62 | 0.60 | IN | 2 + TS | | | | |
| 63 | 0.65 | IN | 2 + TS | | | | |
| 64 | 0.55 | IN | 2 + TS | SN | | | |
| 65 | 0.60 | IN | 2 + TS | SN | | | |
| 66 | 0.65 | IN | 2 + TS | SN | | | |
| 67 | 0.70 | IN | 3 + TS | SN | | | |
| 68 | 0.75 | IN | 3 + TS | SN | | | |
| 69 | 0.80 | IN | 4 + TS | SN | | | |
| 72 | 0.70 | IN | 3 + TS | | | SRT | |
| 73 | 0.75 | IN | 3 + TS | | | SRT | |
| 74 | 0.80 | IN | 3 + TS | | | SRT | |
| 79 | 0.80 | IN | 4 + TS | SN | | | |
| 80 | 0.80 | IN | 4 + TS | | NN | SRT | |
| 86 | 0.85 | IN | 4 + TS | SN | | | NRT |
| 87 | 0.85 | IN | 4 + TS | | | SRT | NRT |
| 88 | 0.90 | IN | 4 + TS | SN | | | NRT |
| 90 | 0.95 | IN | 4 + TS | SN | | | NRT |
| 91 | 0.95 | IN | 4 + TS | | | SRT | NRT |
| 92 | 0.95 | IN | 4 + TS | | NN | SRT | |
| 93 | 0.98 | IN | 4 + TS | | NN | SRT | |
| 95 | 0.98 | IN | 4 + TS | SN | | | NRT |

FIGS. 25, 32, 45, and 46 illustrate yet another representation of a patients optic nerve. The illustrations present optic nerves comprising varying CDR's. The illustration further introduces said optic nerve cup 12 with an orientation referred to as having a superior notch (SN) 22. Said superior notch (SN) 22 is a condition wherein said optic nerve cup 12 encompasses at least a portion of an upper edge of said optic nerve disc 10 or said superior section 9 of the optic disc 10. In a preferred embodiment, notch conditions such as said superior notch (SN) 22 would be identified by a solid lined arrow as shown. Said saucerization grading 30 normally does not apply to instances exhibiting only said superior notch (SN) 22; alternatively said saucerization grading 30 does normally apply when other features are present. In addition to said superior notch (SN) 22 being illustrated as described, said superior notch (SN) 22 is also presented in combination with additional features in other figures presented herein.

The following table presents examples of various said superior notch (SN) 22, both individually and combined with other features:

TABLE 4

Figures illustrating examples of Superior Notch

| FIG. | CDR | SN | TS | IN | NN | IRT | NRT |
|---|---|---|---|---|---|---|---|
| 25 | 0.20 | SN | | | | | |
| 32 | 0.40 | SN | | IN | | | |
| 35 | 0.40 | SN | 1 + TS | | | | |
| 40 | 0.45 | SN | 2 + TS | | | | |
| 45 | 0.30 | SN | | | | | |
| 46 | 0.35 | SN | | | | | |
| 47 | 0.45 | SN | 2 + TS | | | | |
| 48 | 0.65 | SN | 3 + TS | | | | |
| 49 | 0.70 | SN | 3 + TS | | | | |
| 50 | 0.80 | SN | 4 + TS | | | | |
| 64 | 0.55 | SN | 2 + TS | IN | | | |
| 65 | 0.60 | SN | 2 + TS | IN | | | |
| 66 | 0.65 | SN | 2 + TS | IN | | | |
| 67 | 0.70 | SN | 3 + TS | IN | | | |
| 68 | 0.75 | SN | 3 + TS | | | | |
| 69 | 0.80 | SN | 4 + TS | IN | | | |
| 78 | 0.80 | SN | 4 + TS | | | IRT | |
| 79 | 0.80 | SN | 4 + TS | IN | | | |
| 81 | 0.80 | SN | 4 + TS | | NN | | |
| 85 | 0.85 | SN | 4 + TS | | | IRT | NRT |
| 86 | 0.85 | SN | 4 + TS | IN | | | NRT |
| 88 | 0.90 | SN | 4 + TS | IN | | | NRT |
| 90 | 0.95 | SN | 4 + TS | IN | | | NRT |
| 94 | 0.98 | SN | 4 + TS | | NN | IRT | |
| 95 | 0.98 | SN | 4 + TS | IN | | | NRT |

FIGS. 27 through 31 and 41 through 44 illustrate yet another representation of a patients optic nerve. The illustrations present an optic nerve comprising various CDR's and introduce a temporal saucerization (TS) 24 condition. Additional figures further illustrate said temporal saucerization (TS) 24, while including additional features; such will be described later herein. Said temporal side 6 is defined as the side of said optic nerve disc 10 closest to the patient's ear as illustrated in FIGS. 1 and 2 herein. As the descriptions are respective to each of the right eyes 3 and left eye 5 and independent of actual right and left as illustrated, it is critical to correctly identify and record which eye is being recorded. It should be recognized where the opposing geometry is identified, that opposing geometry is described as nasal saucerization (mild nasal saucerization (MNS) is illustrated in FIG. 23).

Temporal saucerization (TS) 24 can be characterized by a saucerization grading 30. Said saucerization grading 30 is a quantitative definition of said temporal saucerization (TS) 24 is the numeric representation between 1 and 4. Various grades are illustrated throughout the illustrations presented as better defined by table 5 herein. The following provides a guideline for saucerization and the respective grading process:

Saucerization in general, can be defined as the thinning, or loss of thickness of these optic nerve fibers in tan anterior-posterior dimension.

a. 1+ equals ¼ thickness loss
b. 2+ equals ½ thickness loss
c. 3+ equals ¾ thickness loss
d. 4+ equals full or complete thickness loss The following table presents examples of various said temporal and nasal saucerization (TS) grading 30:

TABLE 5

Figures illustrating various grades of Saucerization

| FIG. | CDR | MTS, MNS, TS | IN | SN | NN | IRT | SRT | NRT |
|---|---|---|---|---|---|---|---|---|
| 22 | 0.20 | MTS | | | | | | |
| 23 | 0.20 | MNS | | | | | | |
| 26 | 0.26 | MTS | | | | | | |
| 27 | 0.30 | 1 + TS | | | | | | |
| 28 & 29 | 0.35 | 1 + TS | | | | | | |
| 30 & 31 | 0.40 | 1 + TS | | | | | | |
| 34 | 0.40 | 1 + TS | IN | | | | | |
| 35 | 0.40 | 1 + TS | | SN | | | | |
| 36 | 0.40 | 1 + TS | | | NN | | | |
| 37 | 0.40 | 1 + TS | | | | IRT | | |
| 38 | 0.40 | 1 + TS | | | | | SRT | |
| 39 | 0.40 | 1 + TS | | | | | | NRT |
| 55 | 0.50 | 1 + TS | IN | | | | | |
| 56 | 0.30 | 1 + TS | IN | | | | | |
| 57 | 0.40 | 1 + TS | IN | | | | | |
| 96 | 0.40 | 1 + TS | | | NN | | | |
| 40 | 0.45 | 2 + TS | | SN | | | | |
| 41 | 0.45 | 2 + TS | | | | | | |
| 42 | 0.50 | 2 + TS | | | | | | |
| 43 | 0.55 | 2 + TS | | | | | | |
| 44 | 0.60 | 2 + TS | | | | | | |
| 47 | 0.45 | 2 + TS | | SN | | | | |
| 58 | 0.40 | 2 + TS | IN | | | | | |
| 59 | 0.45 | 2 + TS | IN | | | | | |
| 60 | 0.50 | 2 + TS | IN | | | | | |
| 61 | 0.55 | 2 + TS | IN | | | | | |
| 62 | 0.60 | 2 + TS | IN | | | | | |
| 63 | 0.65 | 2 + TS | IN | | | | | |
| 64 | 0.55 | 2 + TS | IN | SN | | | | |
| 65 | 0.60 | 2 + TS | IN | SN | | | | |
| 66 | 0.65 | 2 + TS | IN | SN | | | | |
| 70 | 0.65 | 2 + TS | | | | | SRT | |
| 75 | 0.65 | 2 + TS | | | | IRT | | |
| 97 | 0.50 | 2 + TS | | | NN | | | |
| 98 | 0.60 | 2 + TS | | | NN | | | |
| 48 | 0.65 | 3 + TS | | SN | | | | |
| 49 | 0.70 | 3 + TS | | SN | | | | |
| 67 | 0.70 | 3 + TS | IN | SN | | | | |
| 68 | 0.75 | 3 + TS | IN | SN | | | | |
| 71 | 0.70 | 3 + TS | | | | IRT | SRT | |
| 72 | 0.70 | 3 + TS | IN | | | | SRT | |
| 73 | 0.75 | 3 + TS | IN | | | | SRT | |
| 74 | 0.80 | 3 + TS | IN | | | | SRT | |
| 76 | 0.75 | 3 + TS | | | | IRT | SRT | |
| 99 | 0.70 | 3 + TS | | | NN | | | |
| 50 | 0.80 | 4 + TS | | SN | | | | |
| 69 | 0.80 | 4 + TS | IN | SN | | | | |
| 77 | 0.80 | 4 + TS | | | | IRT | SRT | |
| 78 | 0.80 | 4 + TS | | SN | | IRT | | |
| 79 | 0.80 | 4 + TS | IN | SN | | | | |
| 80 | 0.80 | 4 + TS | IN | | NN | | SRT | |
| 81 | 0.80 | 4 + TS | | SN | NN | | | |
| 82 | 0.80 | 4 + TS | | | NN | IRT | SRT | |
| 83 | 0.80 | 4 + TS | | | | | | |
| 84 | 0.85 | 4 + TS | | | | IRT | SRT | NRT |
| 85 | 0.85 | 4 + TS | | SN | | IRT | | NRT |
| 86 | 0.85 | 4 + TS | IN | SN | | | | NRT |
| 87 | 0.85 | 4 + TS | IN | | | | SRT | NRT |
| 88 | 0.90 | 4 + TS | IN | SN | | | | NRT |
| 89 | 0.90 | 4 + TS | | | | IRT | SRT | NRT |
| 90 | 0.95 | 4 + TS | IN | SN | | | | NRT |
| 91 | 0.95 | 4 + TS | IN | | | | SRT | NRT |
| 92 | 0.95 | 4 + TS | IN | | NN | | SRT | |
| 93 | 0.98 | 4 + TS | IN | | NN | | SRT | |
| 94 | 0.98 | 4 + TS | | SN | NN | IRT | | |
| 95 | 0.98 | 4 + TS | IN | SN | | | | NRT |

FIGS. 45 through 50 illustrate yet another representation of a patient's optic nerve. The illustrations present optic nerves comprising a variety of CDR's. The illustrations present said optic nerve cup 12 with an orientation combining features described as superior notch (SN) 22 and temporal saucerization (TS) 24. Such combined conditions are also presented in Table 4 above.

FIGS. 51 through 63 illustrate yet another representation of a patient's optic nerve. The illustrations present optic nerves comprising a variety of CDR's and said temporal saucerization (TS) grading 30. The illustrations present said optic nerve cup 12 with an orientation combining features described as temporal saucerization (TS) 24 and inferior notch (IN) 26. Such combined conditions are also presented in Table 5 above.

FIGS. 64 through 69 illustrate yet another representation of a patient's optic nerve. The illustrations present optic nerves comprising a variety of CDR's and said temporal saucerization (TS) grading 30. The illustrations present said optic nerve cup 12 with an orientation combining features described as said superior notch (SN) 22, said temporal saucerization (TS) 24 and said inferior notch (IN) 26. Such combined conditions are also presented in Tables 4 and 5 above.

FIGS. 70 through 74, and others as indicated in the table below, illustrate yet another representation of a patient's optic nerve. The illustrations present optic nerves comprising a variety of CDR's and said saucerization grading 30. The illustration further introduces said optic nerve cup 12 with said temporal saucerization (TS) 24 having a geometry referred to as having superior rim thinning (SRT) 34. Said superior rim thinning (SRT) 34 is a condition wherein said optic nerve cup 12 encroaches upon, but does not contact at least a portion of an upper edge of said optic nerve disc 10 or said superior section 7 of said optic disc 10. In a preferred embodiment, rim thinning conditions such as said superior rim thinning (SRT) 34 would be identified by a broken lined arrow as shown. A portion of the figures additionally comprises other features as identified in the table below.

The following table presents examples of various said superior rim thinning (SRT) 34, both individually and combined with other features:

TABLE 6

Figures illustrating a Superior Rim Thinning (SRT) condition

| FIG. | CDR | TS | SRT | IN | NN | IRT | NRT |
|---|---|---|---|---|---|---|---|
| 38 | 0.40 | 1 + TS | SRT | | | | |
| 70 | 0.65 | 2 + TS | SRT | | | | |
| 71 | 0.70 | 3 + TS | SRT | | | IRT | |
| 72 | 0.70 | 3 + TS | SRT | IN | | | |
| 73 | 0.75 | 3 + TS | SRT | IN | | | |
| 74 | 0.80 | 3 + TS | SRT | IN | | | |
| 76 | 0.75 | 3 + TS | SRT | | | IRT | |
| 77 | 0.80 | 4 + TS | SRT | | | IRT | |
| 80 | 0.80 | 4 + TS | SRT | IN | NN | | |
| 82 | 0.80 | 4 + TS | SRT | | NN | IRT | |
| 84 | 0.85 | 4 + TS | SRT | | | IRT | NRT |
| 87 | 0.85 | 4 + TS | SRT | IN | | | NRT |
| 89 | 0.90 | 4 + TS | SRT | | | IRT | NRT |
| 91 | 0.95 | 4 + TS | SRT | IN | | | NRT |
| 92 | 0.95 | 4 + TS | SRT | IN | NN | | |
| 93 | 0.98 | 4 + TS | SRT | IN | NN | | |

FIGS. 71, 75 through 78, and others as indicated in the table below, illustrate yet another representation of a patient's optic nerve. The illustrations present optic nerves comprising a variety of CDR's and said saucerization grading 30. The illustration further introduces said optic nerve cup 12 with said temporal saucerization (TS) 24 having a geometry referred to as having inferior rim thinning (IRT) 32. Said inferior rim thinning (IRT) 32 is a condition wherein said optic nerve cup 12 encroaches upon, but does not contact at least a portion of an lower edge of said optic nerve disc 10 or said inferior section 8 of said optic disc 10. In a preferred embodiment, rim thinning conditions such as said inferior rim thinning (IRT) 32 would be identified by a broken lined arrow as shown. A portion of the figures additionally comprises other features such as inferior notch (IN) 26 and superior rim thinning (SRT) 34.

The following table presents examples of various said inferior rim thinning (IRT) 32, both individually and combined with other features:

TABLE 7

Figures illustrating a Inferior Rim Thinning (IRT) condition

| FIG. | CDR | IN | TS | SN | NN | SRT | NRT |
|---|---|---|---|---|---|---|---|
| 24 | 0.20 | IN | | | | | |
| 32 | 0.40 | IN | | SN | | | |
| 33 | 0.40 | IN | | | NN | | |
| 34 | 0.40 | IN | 1 + TS | | | | |
| 51 | 0.30 | IN | | | | | |
| 52 | 0.35 | IN | | | | | |
| 53 & 54 | 0.40 | IN | | | | | |
| 55 | 0.50 | IN | 1 + TS | | | | |
| 56 | 0.30 | IN | 1 + TS | | | | |
| 57 | 0.40 | IN | 1 + TS | | | | |
| 58 | 0.40 | IN | 2 + TS | | | | |
| 59 | 0.45 | IN | 2 + TS | | | | |
| 60 | 0.50 | IN | 2 + TS | | | | |
| 61 | 0.55 | IN | 2 + TS | | | | |
| 62 | 0.60 | IN | 2 + TS | | | | |
| 63 | 0.65 | IN | 2 + TS | | | | |
| 64 | 0.55 | IN | 2 + TS | SN | | | |
| 65 | 0.60 | IN | 2 + TS | SN | | | |
| 66 | 0.65 | IN | 2 + TS | SN | | | |
| 67 | 0.70 | IN | 3 + TS | SN | | | |
| 68 | 0.75 | IN | 3 + TS | SN | | | |
| 69 | 0.80 | IN | 4 + TS | SN | | | |
| 72 | 0.70 | IN | 3 + TS | | | SRT | |
| 73 | 0.75 | IN | 3 + TS | | | SRT | |
| 74 | 0.80 | IN | 3 + TS | | | SRT | |
| 79 | 0.80 | IN | 4 + TS | SN | | | |
| 80 | 0.80 | IN | 4 + TS | | NN | SRT | |
| 86 | 0.85 | IN | 4 + TS | SN | | | NRT |
| 87 | 0.85 | IN | 4 + TS | | | SRT | NRT |
| 88 | 0.90 | IN | 4 + TS | SN | | | NRT |
| 90 | 0.95 | IN | 4 + TS | SN | | | NRT |
| 91 | 0.95 | IN | 4 + TS | | | SRT | NRT |
| 92 | 0.95 | IN | 4 + TS | | NN | SRT | |
| 93 | 0.98 | IN | 4 + TS | | NN | SRT | |
| 95 | 0.98 | IN | 4 + TS | SN | | | NRT |

FIGS. 77 through 83 illustrate yet additional representations of a patient's optic nerve. Each of these illustrations present a CDR of 0.80. Conditions with a CDR of 0.80 can be considered a transition range for said optic nerve. The various conditions presented with these illustrations have been previously introduced and are defined within other sections herein, further illustrating unique combinations of conditions herein.

FIGS. 84 through 91 illustrate yet another representation of a patient's optic nerve. The illustrations present optic nerves comprising a variety of CDR's and said saucerization grading 30. The illustration further introduces said optic nerve cup 12 with said temporal saucerization (TS) 24 having a geometry referred to as having nasal rim thinning (NRT) 36. Said nasal rim thinning (NRT) 36 is a condition wherein said optic nerve cup 12 encroaches upon, but does not contact at least a portion of said nasal edge of said optic nerve disc 10 or said nasal section 7 of said optic disc 10. In a preferred embodiment, rim thinning conditions such as said nasal rim thinning (NRT) 36 would be identified by a broken lined arrow as shown. A portion of the figures additionally comprise other features such as said superior notch (SN) 22, said inferior notch (IN) 26, said inferior rim thinning (IRT) 32, and said superior rim thinning (SRT) 34.

The following table presents examples of various said nasal rim thinning (NRT) 36, both individually and combined with other features:

TABLE 8

Figures illustrating a Nasal Rim Thinning (NRT) condition

| FIG. | CDR | TS | NRT | IN | SN | IRT | SRT |
|------|------|--------|-----|----|----|-----|-----|
| 39 | 0.40 | 1 + TS | NRT | | | | |
| 84 | 0.85 | 4 + TS | NRT | | | IRT | SRT |
| 85 | 0.85 | 4 + TS | NRT | | SN | IRT | |
| 88 | 0.85 | 4 + TS | NRT | IN | SN | | |
| 87 | 0.85 | 4 + TS | NRT | IN | | | SRT |
| 88 | 0.90 | 4 + TS | NRT | IN | SN | | |
| 89 | 0.90 | 4 + TS | NRT | | | IRT | SRT |
| 90 | 0.95 | 4 + TS | NRT | IN | SN | | |
| 91 | 0.95 | 4 + TS | NRT | IN | | | SRT |
| 95 | 0.98 | 4 + TS | NRT | IN | SN | | |

FIGS. 84 through 95 illustrate yet additional representations of a patient's optic nerve. Each of these illustrations present a CDR of 0.85 through 0.98. Conditions with CDR's in this range generally impact at least three of the four quadrants of said optic nerve disc 10. The various conditions presented with these illustrations have been previously introduced and are defined within other sections herein, further illustrating unique combinations of conditions herein.

FIGS. 96 through 99 illustrate yet another representation of a patients optic nerve. The illustrations present optic nerves comprising a variety of CDR's and said saucerization grading 30. The illustration further introduces a geometry referred to as having nasal notch (NN) 40. Said nasal notch (NN) 40 is a condition wherein said optic nerve cup 12 encroaches upon, but does not contact at least a portion of said nasal edge of said optic nerve disc 10 or said nasal section 7 of said optic disc 10. In a preferred embodiment, notch conditions such as said nasal notch (NN) 40 would be identified by a solid lined arrow as shown. A portion of the figures additionally comprises other features such as said inferior notch (IN) 26 and said superior rim thinning (SRT) 34.

The following table presents examples of said nasal notch (NN) 40 conditions, both individually and combined with other features:

TABLE 9

Figures illustrating a Nasal Notch (NN) condition

| FIG. | CDR | TS | NN | IN | SN | IRT | SRT |
|------|------|--------|----|----|----|-----|-----|
| 33 | 0.40 | | NN | IN | | | |
| 36 | 0.40 | 1 + TS | NN | | | | |
| 80 | 0.80 | 4 + TS | NN | IN | | | SRT |
| 81 | 0.80 | 4 + TS | NN | | SN | | |
| 82 | 0.80 | 4 + TS | NN | | | IRT | SRT |
| 92 | 0.95 | 4 + TS | NN | IN | | | SRT |
| 93 | 0.98 | 4 + TS | NN | IN | | | SRT |
| 94 | 0.98 | 4 + TS | NN | | SN | IRT | |
| 98 | 0.40 | 1 + TS | NN | | | | |
| 97 | 0.50 | 2 + TS | NN | | | | |
| 98 | 0.60 | 2 + TS | NN | | | | |
| 99 | 0.70 | 3 + TS | NN | | | | |

FIG. 100 is an illustration representing features of a display from the present invention. It is understood that the actual presentation would comprise at least a portion of the elements presented, wherein the actual appearance and manner may differ while maintaining the spirit and intent of the present invention. Said display would comprise a graphical optic nerve representation 50. Said graphical optic nerve representation 50 would be supported with two key elements presented, said key elements being a CDR record 52 and a eye reference 54. Said graphical optic nerve representation 50 comprises said optic nerve disc 10, said optic nerve cup 12 in any geometry and location respective to the patients evaluation. Additionally, said graphical optic nerve representation 50 can further comprise solid and broken arrows to quickly identify specific features. The preferred embodiment utilizes solid arrows to identify notch locations and broken arrows to identify rim thinning areas. Patient visit information is recorded in patient visit log, said patient visit log comprising:

TABLE 10

Patient Visit Log Elements

| Reference | Actual |
|-----------|--------|
| patient identifier 56 | actual patient name 58 |
| visit identifier 60 | actual visit date 62 |
| doctor identifier 64 | actual doctor name 66 |
| technician identifier 68 | actual technician name 70 |

Optionally, optic nerve features can be presented in a text format as well as via said graphical optic nerve representation 50. Said optional information can comprise, but not limited to the following:

TABLE 11

Optic Nerve Supporting Text

| Reference | Actual |
|-----------|--------|
| grading identifier 72 | actual grade 72 |
| saucerization location identifier 76 | actual saucerization location 78 |
| notch location identifier 80 | actual notch location 82 |

FIG. 101 is a representative flow diagram presenting the steps respective to an optic nerve electronic method flow diagram 100. Said optic nerve electronic method flow diagram 100 initiates with a software initiation step 102, wherein said software initiation step 102 starts the respective software program. A first step would comprise a patient file decision step 104, wherein said patient file decision step 104 determines if the subject patient file already exists within a database utilized by the software. One such means would be wherein the user enters at least a portion of the Patients name or other patient identifier. Said patient file decision step 104 would search said database for records related to the subject patient. Should the patient file decision step 104 present a result of nothing found (NO), said optic nerve electronic method flow diagram 100 would then direct the user to a patient file creation step 106. Said patient file creation step 106 would guide the user through the steps for entering the required and optional patient information. Should the patient file decision step 104 present a result of subject patient file found (YES), said optic nerve electronic method flow diagram 100 would present the identified subject patient file(s) in accordance with a patient file location step 108 for verification. The user would review the found patient file and verify that the found file is the respective to the subject patient. If the found file is not correct, the user can either: return to said patient file decision step 104 or proceed with said patient file creation step 106. Once the subject patient information is identified and the software has established such accordingly, said optic nerve electronic method flow diagram 100 continues with a patient visit information entry step 110. Said patient visit information entry step 110 guides the user through the method for entering the patient visit information. Such information can include: date of visit, time of visit, Doctor, technician, reason for visit, and any other respective visit information. The entered information can be presented for validation, and upon validation, said optic nerve electronic method flow diagram 100 would proceed to an optic nerve information entry step 112. Said optic nerve information entry step 112 comprising the method of entering information to create a graphical representation of the optic nerve. Options of said optic nerve information entry step 112 are expanded upon later herein. Optionally, one can complete an optic nerve image entry step 114, wherein said optic nerve image entry step 114 provides the user the ability to upload an actual electronic image of the optic nerve. It is desirable that said optic nerve electronic method flow diagram 100 comprise a means for validating the graphical representation prior to saving said graphical representation. The validation can be accomplished by incorporating a graphical representation display step 116 and a respective graphical image verification decision step 118. Said graphical representation display step 116 displays the computer generated graphical optic nerve representation 50 and requests the user to verify that said graphical optic nerve representation 50 is accurate in accordance with said graphical image verification decision step 118. Should the user select "NO" during said graphical image verification decision step 118, said optic nerve electronic method flow diagram 100 directs the user back to said optic nerve information entry step 112. Should the user select "YES" during said graphical image verification decision step 118, said optic nerve electronic method flow diagram 100 considers entry of the optic nerve for that respective eye complete. Said optic nerve electronic method flow diagram 100 determines if the information entered was the first or second eye. If the information was only respective to a first eye, said optic nerve electronic method flow diagram 100 directs the user to said optic nerve information entry step 112; repeating the process for a second eye. If the information was respective to said second eye, said optic nerve electronic method flow diagram 100 is considered as patent entry completed 122.

FIG. 102 is a representative flow diagram presenting the steps respective to an expanded optic nerve information data entry step 200, wherein said expanded optic nerve information data entry step 200 directs the user through a series of data entries to generate said graphical optic nerve representation 50. Said expanded optic nerve information data entry step 200 is a first expanded representation of said optic nerve information entry step 112. Said expanded optic nerve information data entry step 200 initiates via a CDR entry step 202, wherein said CDR entry step 202 directs the user to enter said cup to disc ratio (CDR). The software optionally comprising a presentation of a series of images of optic nerves with various CDR's to aid the user in determining the correct CDR. Upon entry of said CDR, the software proceeds to an optional total rim loss decision step 204, wherein said optional total rim loss decision step 204 determines if the user entered 1.00 or 100%. Should said optional total rim loss decision step 204 determine "YES" (most simplistic representation) said expanded optic nerve information data entry step 200 proceeds to said graphical representation display step 116, presenting an image representative of a total rim loss condition (see FIG. 3 herein). Should said optional total rim loss decision step 204 determine "NO" said expanded optic nerve information data entry step 200 proceeds to a full rim decision step 208. Said full rim decision step 208 questions the user if the image is considered a full rim or not. Should said full rim decision step 208 determine "YES" expanded optic nerve information data entry step 200 proceeds to said graphical representation display step 116, presenting an image representative of a full rim loss condition having a CDR of the value previously entered in accordance with said CDR entry step 202 (See table 1 herein). Optionally, said expanded optic nerve information data entry step 200 can proceed to an optic disc shaping entry step 220 to provide an off-center positioning of said optic disc 12. Should said full rim decision step 208 determine "NO" expanded optic nerve information data entry step 200 proceeds to said saucerization entry step 210, wherein said saucerization entry step 210 directs the user to enter the specific type(s) of saucerization. Said saucerization entry step 210 can comprise the elements of selecting a temporal saucerization selection 212, a mild temporal saucerization selection 214, a nasal saucerization selection 216, and a mild nasal saucerization selection 218. The user can enter one or more of the selections within said saucerization entry step 210.

Upon completion of said saucerization entry step 210, the user would be directed to an optic disc shaping entry step 220. Said optic disc shaping entry step 220 can comprise the elements of selecting an inferior rim thinning selection 222, a superior rim thinning selection 224, a temporal rim thinning selection 226, a nasal rim thinning selection 228, an other shapes selection 230, an inferior notch selection 232, and a superior notch selection 234. Each of said selections are presented in detail within the specification. Should the user select said other shapes selection 230, said expanded optic nerve information data entry step 200 proceeds to a unique shape entry step 236 allowing the user to enter any unique shapes, comments, and the like. Upon completion of the entry process, the software generates an electronic, graphical optic nerve representation 50 in accordance with an electronic representation generation step 238. Said graphical optic nerve representation 50 is then presented to the user in accordance with said graphical representation display step 116.

FIG. 103 is a representative flow diagram presenting the steps respective to an expanded optic nerve information image selection step 300, wherein said expanded optic nerve information image selection step 300 directs the user through a series of data entries to generate said graphical optic nerve representation 50. Said expanded optic nerve information image selection step 300 is a second expanded representation of said optic nerve information entry step 112. Said expanded optic nerve information image selection step 300 initiates via a CDR example presentation/selection step 302, wherein said CDR example presentation/selection step 302 directs the user to enter said cup to disc ratio (CDR). The software presents a series of images of optic nerves with various CDR's to aid the user in determining the correct CDR. One of the presented images is of total rim loss (See FIG. 3 herein). Upon selection of said CDR, the software proceeds to an optional total rim loss image decision step 304, wherein said optional total rim loss image decision step 304 determines if the user selected an image representative of total rim loss. Should said optional total rim loss image decision step 304 determine "YES" said expanded optic nerve information image selection step 300 proceeds to said graphical representation display step 116, presenting an image representative of a total rim loss condition (see FIG. 3 herein). Should said optional total rim loss image decision step 304 determine "NO" said expanded optic nerve information image selection step 300 proceeds to a full rim image selection step 308. Said full rim image selection step 308 presents the user with at least one image representative of a full rim 16 condition and directs the user to determine whether the presented full rim image is representative of the patients optic nerve or not. Should said full rim image selection step 308 select "YES" (match) said expanded optic nerve information image selection step 300 proceeds to said graphical representation display step 116, presenting an image representative of a full rim loss condition having a CDR of the value previously selected via the various images presented in accordance with said CDR example presentation/selection step 302 (See table 1 herein). Optionally, said expanded optic nerve information image selection step 300 can proceed to an optic disc shaping image selection step 320 to select an off-center positioning of said optic disc 12. Should said full rim image selection step 308 determine "NO" expanded optic nerve information image selection step 300 proceeds to a saucerization image selection step 310, wherein said saucerization image selection step 310 directs the user to enter the specific type(s) of saucerization. Said saucerization image selection step 310 can comprise presenting images, one or more images representing each of the following features: a temporal saucerization image selection 312, a mild temporal saucerization image selection 314, a nasal saucerization image selection 316, and a mild nasal saucerization image selection 318. The user can enter one or more of the selections within said saucerization image selection step 310.

Upon completion of said saucerization image selection step 310, the user would be directed to an optic disc shaping image selection step 320. Said optic disc shaping image selection step 320 is accomplished by presenting various images representative of the following features: an inferior rim thinning image 322, a superior rim thinning image 324, a temporal rim thinning image 326, a nasal rim thinning image 328, an other shapes image 330, an inferior notch image 332, and a superior notch image 334. Each of said selections are presented in detail within the specification. Should the user select said optic disc shaping image selection step 320, said expanded optic nerve information image selection step 300 proceeds to unique shape image adjustment step 336 allowing the user to adjust the image(s), enter comments, and the like. Upon completion of the entry process, the software generates an electronic, graphical optic nerve representation 50 in accordance with an electronic representation generation step 338. Said graphical optic nerve representation 50 is then presented to the user in accordance with said graphical representation display step 116.

FIG. 104 is a representative flow diagram presenting the steps respective to an expanded optic nerve information image drawing step 400, wherein said expanded optic nerve information image drawing step 400 directs the user through a series of drawing or image modification steps to generate said graphical optic nerve representation 50. Said expanded optic nerve information image drawing step 400 is a third expanded representation of said optic nerve information entry step 112. Said expanded optic nerve information image drawing step 400 initiates via a drawing cup within disc step 402, wherein said drawing cup within disc step 402 directs the user to draw or size a pre-drawn shape of said optic nerve cup 12 within said optic nerve disc 10 to create a cup to disc ratio (CDR). The software can present said optic nerve cup 12 within said optic nerve disc 10 and the user would expand or contract said optic nerve cup 12 using any entry manner to place said optic nerve cup 12 to the correct size. Should the entry user draw said CDR to 100% (Total Rim Loss), said expanded optic nerve information image drawing step 400 can optionally comprise a said optional total rim loss decision step 204. Should said optional total rim loss decision step 204 determine "YES" said expanded optic nerve information image drawing step 400 proceeds to said graphical representation display step 116, presenting an image representative of a total rim loss condition (see FIG. 3 herein). Should said optional total rim loss decision step 204 determine "NO" said expanded optic nerve information image drawing step 400 proceeds to an optional full rim decision step 208. Said optional full rim decision step 208 allows the user to enter whether said optic nerve disc 12 can be considered a full rim condition. Should said full rim decision step 208 select "YES" (match) said expanded optic nerve information image drawing step 400 proceeds to said graphical representation display step 116, presenting an image representative of a full rim loss condition having a CDR drawn in accordance with said drawing cup within disc step 402. Should said full rim decision step 208 determine "NO" expanded optic nerve information image drawing step 400 proceeds to a manually adjust cup position step 410, wherein said manually adjust cup position step 410 directs the user to adjust to position of said optic nerve cup 12 respective to said optic nerve disc 10. Said manually adjust cup position step 410 can be accomplished via many known user entry methods including selecting and dragging said optic nerve cup 12. Normally, this results in one or of the following conditions: a temporal saucerization image selection 212, a mild temporal saucerization image selection 214, a nasal saucerization image selection 216, and a mild nasal saucerization image selection 218.

Upon completion of said manually adjust cup position step 410, the user would be directed to an manually adjust cup shape step 420. Said manually adjust cup shape step 420 is accomplished by further adjusting the shape, position, and the like of said optic nerve cup 12 respective to any of the applicable following conditions: an inferior rim thinning 222, a superior rim thinning 224, a temporal rim thinning 226, a nasal rim thinning 228, an other shapes image 230, an inferior notch image 232, and a superior notch image 234. Each of said conditions are presented in detail within the specification. Additional notes, features, and the like can be entered via an optional manually adjust unique shape features step 436. Upon completion of the entry process, the software generates an electronic, graphical optic nerve representation 50 in accordance with an electronic representation generation step 238. Said graphical optic nerve representation 50 is then presented to the user in accordance with said graphical representation display step 116.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

We claim:

1. A method for documenting a patient's optic nerve, said optic nerve documentation method comprising:
   recording a reference to a patient;
   referencing an optic nerve in a manner understood to be at least one of ocular dexter (Right eye) and ocular sinister (Left eye);

providing a illustrative representation of an optic nerve cup;

recording a cup to disc ratio; and an optic nerves condition diagnosis represented by at least one of:
  a) the optic nerve cup illustration identifying a Full Rim condition via a optic nerve cup representation being an inner round object located completely within an optic nerve disc representation being an outer round object and a value indicating the percentage of the cup to disc ration (CRD),
  b) the optic nerve cup illustration identifying a Notch condition via a optic nerve cup representation being an inner round object located within and contacting an optic nerve disc representation being an outer round object, further including a first arrow style with the arrow directed towards the contacting area of the two round objects,
  c) the optic nerve cup illustration identifying a Rim Thinning via a optic nerve cup representation being an inner round object located within and encroaching upon an optic nerve disc representation being an outer round object, further including a second arrow style with the arrow directed towards the encroached area.

2. The method for documenting a patient's optic nerve of claim 1, wherein at least one of said first arrow style and said second arrow style comprising a solid lined arrow.

3. The method for documenting a patient's optic nerve of claim 1, wherein at least one of said first arrow style and said second arrow style comprising a dashed lined arrow.

4. The method for documenting a patient's optic nerve of claim 1, wherein:
  at least one of said first arrow style and said second arrow style comprising a solid lined arrow;
  at least one of said first arrow style and said second arrow style comprising a dashed lined arrow; and
  said first arrow line style differs from said second arrow line style.

5. The method for documenting a patient's optic nerve of claim 1, said optic nerve documentation method further comprising:
  recording a grading respective to saucerization.

6. The method for documenting a patient's optic nerve of claim 1, said optic nerve documentation method further comprising:
  shading of said optic nerve cup.

7. An electronic method for documenting a patient's optic nerve, said optic nerve electronic documentation method comprising:
  electronically recording a reference to a patient;
  entering a position of an optic nerve cup respective to an optic nerve disc;
  entering at least one optic nerve cup shape detail;
  creating an electronic graphical representation of said optic nerve cup based upon said entered position and entered at least one optic nerve cup shape detail;
  displaying said electronic graphical representation of said optic nerve cup created based upon said entered position and entered at least one optic nerve cup shape detail;
  verifying the accuracy of said displayed electronic graphical representation of said optic nerve cup; and
  electronically saving a record representative of information required to recreate said electronic graphical representation of said optic nerve cup.

8. The electronic method for documenting a patient's optic nerve of claim 7, said optic nerve electronic documentation method further comprising:
  an identification of an optic nerve in a manner understood to be at least one of ocular dexter (Right eye) and ocular sinister (Left eye).

9. The electronic method for documenting a patient's optic nerve of claim 7, said optic nerve electronic documentation method further comprising:
  a cup to disc ratio; and
  indicating at least one of:
  a) Full Rim,
  b) a Notch condition, and
  c) a Rim Thinning condition.

10. The method for documenting a patient's optic nerve of claim 9, wherein said Notch condition is identified via a first arrow style and said Rim Thinning condition is identified via a second arrow style.

11. The method for documenting a patient's optic nerve of claim 10, wherein at least one of said first arrow style and said second arrow style comprising a dashed lined arrow.

12. The method for documenting a patient's optic nerve of claim 10, wherein: at least one of said first arrow style and said second arrow style comprising a solid lined arrow;
  at least one of said first arrow style and said second arrow style comprising a dashed lined arrow; and
  said first arrow line style differs from said second arrow line style.

13. The method for documenting a patient's optic nerve of claim 7, said optic nerve documentation method further comprising:
  recording a grading respective to saucerization.

14. The method for documenting a patient's optic nerve of claim 7, said optic nerve documentation method further comprising the ability to enter any unique shape features that are not stored as a standard configuration.

15. An electronic method for documenting a patient's optic nerve, said optic nerve electronic documentation method comprising:
  recording a patient's first optic nerve representation file, said representation file comprising:
  A) electronically referencing a recording to a patient;
  B) electronically recording a date of the examination of the patient;
  C) entering a position of an optic nerve cup respective to an optic nerve disc;
  D) entering at least one optic nerve cup shape detail;
  E) creating an electronic graphical representation of said optic nerve cup based upon said entered position and entered at least one optic nerve cup shape detail;
  displaying said electronic graphical representation of said optic nerve cup created based upon said entered position and entered at least one optic nerve cup shape detail;
  F) electronically saving a record representative of information required to recreate said electronic graphical representation of said optic nerve cup; and
  repeating the steps respective to a patient's first optic nerve representation file to obtain a patient's second optic nerve representation file process during a subsequent patient's examination.

16. The electronic method for documenting a patient's optic nerve of claim 15, the method further comprising:
  repeating the steps respective to a patient's first optic nerve representation file to obtain at least three patient's optic nerve representation files process during a plurality of patient's examinations.

17. The electronic method for documenting a patient's optic nerve of claim 16, the method further comprising:

presenting the images generated by the electronic graphical representation of said optic nerve cup from the at least three patient's optic nerve representation files in accordance with a sequence respective to each examination.

18. The electronic method for documenting a patient's optic nerve of claim 15, said optic nerve electronic documentation method further comprising:

an identification of an optic nerve in a manner understood to be at least one of ocular dexter (Right eye) and ocular sinister (Left eye).

19. The electronic method for documenting a patient's optic nerve of claim 18, the method further comprising:

repeating the steps respective to a patient's first optic nerve representation file to obtain at least three patient's optic nerve representation files process during a plurality of patient's examinations.

20. The electronic method for documenting a patient's optic nerve of claim 19, the method further comprising:

presenting the images generated by the electronic graphical representation of said optic nerve cup from the at least three patient's optic nerve representation files in accordance with a sequence respective to each examination.

* * * * *